United States Patent
Steinman et al.

(10) Patent No.: US 6,475,483 B1
(45) Date of Patent: Nov. 5, 2002

(54) METHOD FOR IN VITRO PROLIFERATION OF DENDRITIC CELL PRECURSORS AND THEIR USE TO PRODUCE IMMUNOGENS FOR TREATING AUTOIMMUNE DISEASES

(75) Inventors: Ralph M. Steinman, Westport, CT (US); Kayo Inaba, Kyoto (JP); Gerold Schuler, Innsbruck (AT)

(73) Assignees: Merix Bioscience, Inc., Durham, NC (US); The Rockefeller University, New York, NY (US)

( * ) Notice: Subject to any disclaimer, the term of this patent is extended or adjusted under 35 U.S.C. 154(b) by 0 days.

(21) Appl. No.: 09/451,511

(22) Filed: Nov. 30, 1999

Related U.S. Application Data

(60) Division of application No. 08/291,537, filed on Jun. 17, 1994, which is a continuation-in-part of application No. 08/040,677, filed on Mar. 31, 1993, now abandoned, which is a continuation-in-part of application No. 07/981,357, filed on Nov. 25, 1992, now abandoned, which is a continuation-in-part of application No. 07/861,612, filed on Apr. 1, 1992, now abandoned.

(51) Int. Cl.$^7$ .............................................. A01N 63/00

(52) U.S. Cl. ..................................... 424/93.7; 435/372

(58) Field of Search ........................ 435/372; 424/93.7, 424/93.71

(56) References Cited

U.S. PATENT DOCUMENTS 5,994,126 A * 11/1999 Steinman et al.

OTHER PUBLICATIONS

Inaba, Kayo et al.; "Identification of Proliferating Dendritic Cell Precursors in Mouse Blood"; J. Exp. Med., May 1992, vol. 175, pp. 1157–1167.

Scheicher, Christoph et al.; "Dendritic Cells from Mouse Bone Marrow: In Vitro Differentiation Using Low Doses of Recombinant Granulocyte–Macrophage Colony–Stimulating Factor"; Journal of Immunological Methods, 1992, vol. 154, pp. 254–264.

Steinman, Ralph M.: "The Dendritic Cell System and Its Role in Immunogenicity"; Annual Review in Immunology, 1991, vol. 9, pp. 271–296.

Freudenthal, Peter S. et al.; "The Distinct Surface of Human Blood Dendritic Cells As Observed After An Improved Isolation Method"; Proc. Natl. Acad. Sci. USA, Oct. 1990, vol. 87, No. 19, pp. 7698–7702.

Inaba, Kay et al.; "Dendritic Cells Pulsed with Protein Antigens in Vitro Can Prime Antigen–Specific, MHC–restricted T Cells in Situ"; Journal of Experimental Medicine, Aug., 1990, vol. 172, No. 2, pp. 631–640.

Vakkila, J. et al.; "Human Peripheral Blood–Derived Dendritic Cells Do Not Produce Interleukin 1α, Interleukin 1β or Interleukin 6"; Scandinavian Journal of Immunology, 1990, vol. 31, pp 345–352.

Crowley, Mary et al.; "Dendritic Cells Are the Principal Cells in Mouse Spleen Bearing Immunogenic Fragments of Foreign Proteins"; Journal of Experimental Medicine; Jul. 1990, vol. 172, pp. 383–386.

Koch, Franz et al.; "Tumor Necrosis Factor α Maintains the Viability of Murine Epidermal Langerhans Cells in Culture, but in Contrast to Granulocyte/Macrophage Colony–Stimulating Factor, without Inducing their Functional Maturation"; J. Exp. Med.; Jan. 1, 1990, vol. 171, pp. 159–171.

MacPherson G.G.; "Lymphoid Dendritic Cells: Their Life History and Roles in Immune Responses"; Research I Immunology, 1989, vol. 140, pp. 877–926.

Barfoot, R. et al., "Some Properties of Dendritic Macrophages from Peripheral Lymph"; Immunology, Oct. 1989, vol. 68, pp. 233–239.

MacPherson, G.G. et al; "Properties of Lymph–Borne (Veiled) Dendritic Cells in Culture"; Immunology, Sep. 1989, vol. 68, pp. 108–113.

Witmer–Pack, Margit D., et al.; "Granulocyte/Macrophage Colony—Stimulating Factor is Essential for the Viability and Function of Cultured Murine Epidermal Langerhans Cells"; J. Exp. Med., Nov. 1987, vol. 166, No. 1, pp. 1484–1498.

Schuler, Gerold et al.; "Epidermal Langerhans Cells Represent Immature Dendritic Cells That Must Differentiate Prior to Expressing their Full Immunologic Potential"; Investigative Dermatology; Jul. 1986, vol. 87, No. 1, p. 166.

Bowers, William E. et al.; "Differentiation of Dendritic Cells in Cultures of Rat Bone Marrow Cells"; J. Exp. Med.; Apr. 1986, vol. 163, pp. 872–883.

Inaba, Kayo et al.; "Properties of Memory T Lymphocytes Isolated from the Mixed Leukocyte Reaction"; Proc. Natl. Acad. Sci. USA; Nov. 1985, vol. 82, pp. 7686–7690.

Francotte, M. et al.; "Enhancement of Antibody Response by Mouse Dendritic Cells Pulsed with Tobacco Mosaic Virus or with Rabbit Antiidiotypic Antibodies Raised against a Private Rabbit Idiotype"; Proc. Natl. Acad. Sci. USA; Dec. 1985, vol. 82, pp. 8149–8152.

Inaba, Kayo et al.; "Protein Specific Helper T—Lymphocyte Formation Initiated by Dendritic Cells"; Science; Aug. 1985, vol. 299, 475–479.

(List continued on next page.)

Primary Examiner—Leon B. Lankford, Jr.
(74) Attorney, Agent, or Firm—Hale and Dorr LLP

(57) ABSTRACT

A method for producing proliferating cultures of dendritic cell precursors is provided. Also provided is a method for producing mature dendritic cells in culture from the proliferating dendritic cell precursors. The cultures of mature dendritic cells provide an effective means of producing novel T cell dependent antigens comprised of dendritic cell modified antigens or dendritic cells pulsed with antigen, including particulates, which antigen is processed and expressed on the antigen-activated dendritic cell. The novel antigens of the invention may be used as immunogens for vaccines or for the treatment of disease. These antigens may also be used to treat autoimmune diseases such as juvenile diabetes and multiple sclerosis.

15 Claims, 31 Drawing Sheets

OTHER PUBLICATIONS

Figure 1:
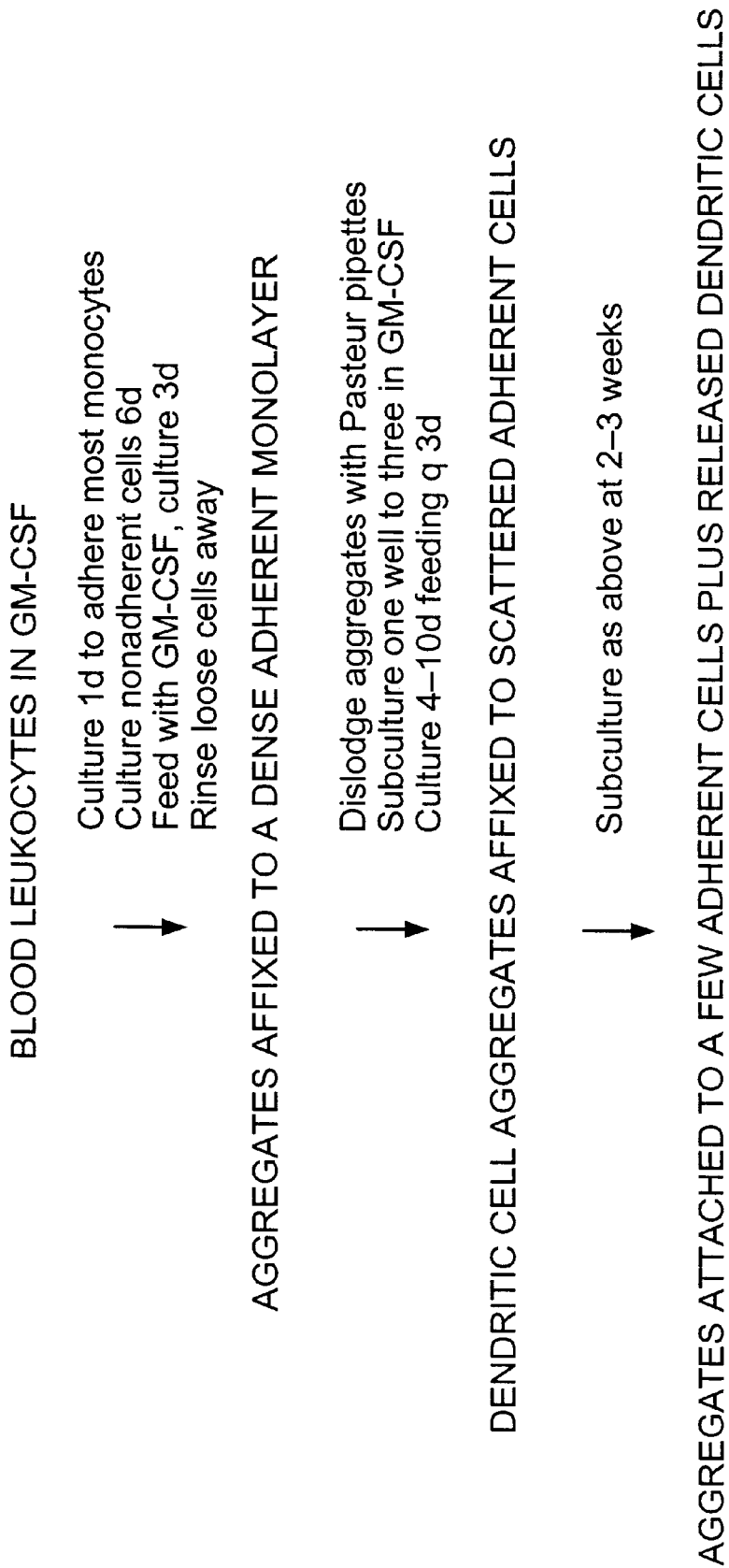
Figure 3A:
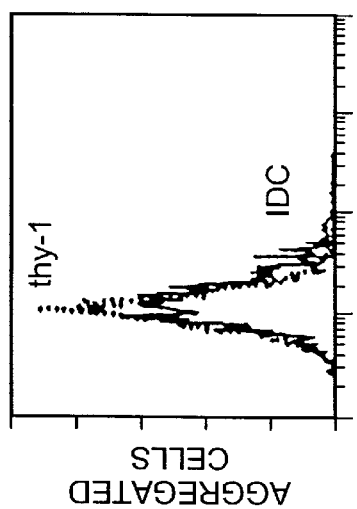
Figure 3B:
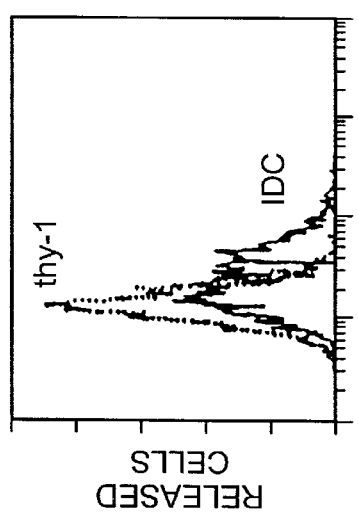
Figure 3C:
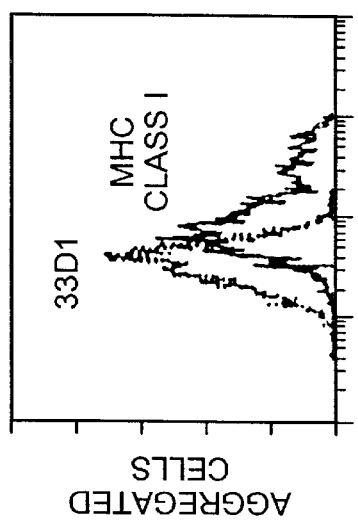
Figure 3D:
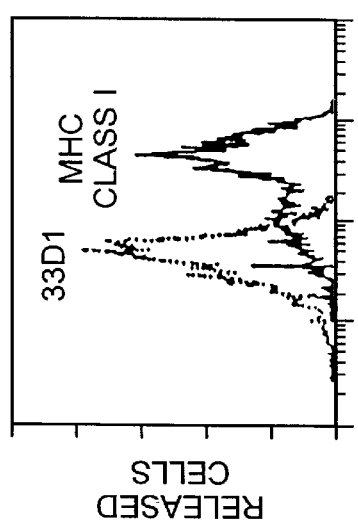
Figure 3E:
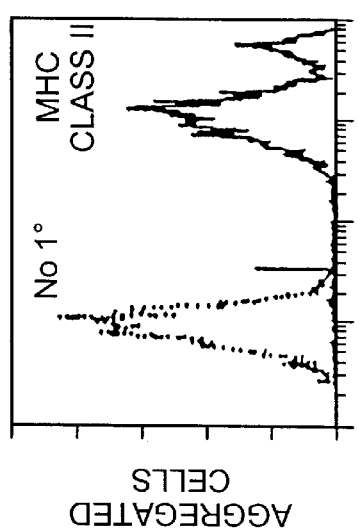
Figure 3F:
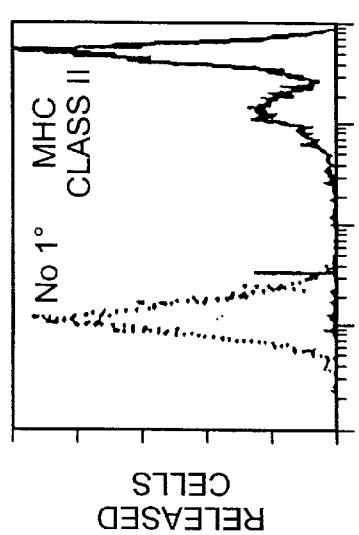

Inaba, Kayo et al.; "Clustering of Dendritic Cells, Helper T Lymphocytes, and Histocompatible B Cells During Primary Antibody Responses in Vitro"; J. Exp. Med.; Sep. 1984, vol. 160, pp. 858–876.

Knight, Stella C, et al.; "Role of Veiled Cells in Lymphocyte Activation"; European Journal of Immunology; Dec. 1982, vol. 12, pp. 1057–1060.

Kraal, Georg et al.; "Langerhans' Cells, Veiled Cells, and Interdigitating Cells in the Mouse Recognized by a Monoclonal Antibody"; J. Exp. Med., May 1986, vol. 163, pp. 981–997.

Inaba, Kayo et al.; "Resting and Sensitized T Lymphocytes Exhibit Distinct Stimulatory (Antigen–Presenting Cell) Requirements for Growth and Lymphokine Release"; J. Exp. Med.; Dec. 1984, vol. 160, pp. 1717–1735.

Klinkert, Wolfgang et al.; "Accessory and Stimulating properties of Dendritic Cells and Macrophages Isolated from Various Rat Tissues"; J. Exp. Med., Aug. 1982, vol. 156, pp. 1–19.

Van Voorhis, Wesley C. et al.; "Human Dendritic Cells"; J. Exp. Med., Apr. 1982, vol. 155, pp. 1172–1187.

Mason, D.W. et al.; "The Rat Mixed Lymphocyte Reaction: Roles of a Dendritic Cell in Intestinal Lymph and T–Cell Subsets Defined by Monoclonal Antibodies"; Immunology; Sep. 1981, vol. 44, pp. 75–87.

Steinman, Ralph M. et al.; "Identification of a Novel Cell Type in Peripheral Lymphoid Organs of Mice"; J. Exp. Med.; Feb. 1979, vol. 149, pp. 1–16.

Steinman, Ralph M., et al.; "Identification of a Novel Cell Type in Peripheral Lymphoid Organs of Mice"; J. Exp. Med.; Apr. 1973, vol. 137, pp. 1142–1162.

Caux, Christophe et al.; "Tumor Necrosis Factor–alpha Strongly Potentiates Interleukin–3 and Granulocyte– Macrophage Colony–Stimulating Factor–Induced Proliferation of Human $CD34^+$ Hematopoietic Progenitor Cells"; Blood, Jun. 1990, vol. 75, pp. 2292–2298.

"Peripheral Stem Cells Made to Work"; The Lancet, Mar. 1992, vol. 339, pp. 648–649.

Boog, Clair J.P. et al.; "Abolition of Specific Immune Response Defect by Immunization with Dendritic Cells"; Nature, Nov. 1985, vol. 318, pp. 59–62.

Rudensky, Alexander Yu, et al.; "Sequence Analysis of Peptides Bound to MHC Class II Molecules"; Nature, Oct. 1991, vol. 353, pp. 622–627.

Faustman, Denise L. et al.; Prevention of Rejection of Murine Islet Allografts by Pretreatment with Anti–Dendritic Cell Antibody; Proc. Natl. Acad. Sci. USA, Jun. 1984, vol. 81, pp 3864–3868.

Ziegler, H. Kirk et al.; "Decrease in Macrophage Antigen Catabolism Caused by Ammonia and Chloroquine is Associated with Inhibition of Antigen Presentation to T Cells"; Proc. Natl. Acad. Sci. USA, Jan. 1982, vol. 79, pp 175–178.

Lechler, R.I et al.; "Restoration of Immunogenicity to Passenger Cell–Depleted Kidney Allografts by the Addition of Donor Strain Dendritic Cells"; J. Exp. Med., Jan 1982, vol. 155, pp. 31–41.

Shimonkevitz, Richard et al.; Antigen Recognition by H–2–Restricted T Cells; J. Exp. Med., Aug. 1983, vol. 158, pp. 303–316.

Bujdoso, Raymond et al.; "Characterization of Sheep Afferent Lymph Dendritic Cells and their Role in Antigen Carriage"; J. Exp. Med., Oct. 1989, vol. 170, pp. 1285–1302.

Holt, Patrick G. et al.; "MHC Class II Antigen–Bearing Dendritic Cells in Pulmonary Tissues of the Rat"; J. Exp. Med., Feb. 1988, vol. 167, pp. 262–274.

Britz, J.S. et al.; "Specialized Antigen–Presenting Cells, Splenic Dendritic Cells and Peritoneal–Exudate Cells Induced by Mycobacteria Activate Effector T Cells that are Resistant to Suppression"; J. Exp. Med., May 1982, vol. 155, pp. 1344–1356.

Iwai, Hiroshi, et al.; "Acceptance of Murine Thyroid Allografts by Pretreatment of Anti–la Antibody or Anti–Dendrictic Cell Antibody in Vitor"; Transplantation, Jan. 1989, vol. 47, pp. 45–49.

Wraith, David C. et al.; "Antien Recognition in Autoimmune Encephalomyelitis and the Potential for Peptide–Mediated Immunotherapy"; Cell, 1980, vol. 59, pp. 247–255.

Nonacs, Ruta et al.; "Mechanisms of Mouse Spleen Dendritic Cell Function in the Generation of Influenza–specific, Cytolytic T. Lymphocytes"; J. Exp. Med., Aug. 1992, vol. 176, pp. 519–529.

Nixon–George, Ann et al.; "The Adjuvant Effect of Stearyl Tyrosine on a Recombinant Subunit Hepatitis B Surface Antigen"; The Journal of Immunology, Jun. 1990, vol. 144, pp. 4798–4802.

Waksman, Byron H. et al.; "Multiple Sclerosis as a Disease of Immune Regulation"; Proceedings of the Society for Experimental Biology and Medicine, 1984, vol. 175, pp. 282–294.

Dechema Biotechnol. Conf. 4(PT. A. Lect. Dechema Annu. Meet. Biotech. $8^{th}$, 1990), pp. 181–184.

Inaba, Kayo et al.; "Generation of Large Numbers of Dendritic Cells from Mouse Bone Marrow Cultures Supplemented with Granulocyte/Macrophage Colony–stimulating Factor"; J. Exp. Med., Dec. 1992, vol. 176, pp. 1693–1702.

Reid, Cecil D.L. et al.; "Interactions of Tumor Necrosis Factor with Granulocyte Macrophage Colony–Stimulating Factor and Other Cytokines in the Regulation of Dendritic Cell Growth in Vitro from Early Bipotent $CD34^+$ Progenitors in Human Marrow"; The Journal of Immunology, Oct. 15, 1992, vol. 149 pp. 2681–2688.

Naito, Koji et al.; "Macrophage Factors which Enhance the Mixed Leukocyte Reaction Initiated by Dendritic Cells"; The Journal of Immunology, May 15, 1989, vol. 142, pp. 1834–1839.

Inaba, Kayo et al; "The Function of $la^+$ Dendritic Cells and la Dendritic Cell Precursors in Thymocyte Mitogenesis to Lectin and Lectin Plus Interleukin 1"; J. Med., Jan. 1988, vol. 167, pp. 149–162.

Fisher, Richard I. et al.; "Neoplastic Cells Obtained from Hodgkin's Disease as Accessory Cells for Mitogen–Induced Human T Cell Proliferative Responses"; Journal of Immunology, May 1984, vol. 132, No. 5, pp. 2672–2677.

Shoukat Dedhar et al.; "Human Granulocyte–Macrophage Colony–Stimulating Factor a Growth Factor Active on a Variety of Cell Types of Nonhemopoietic Origin"; Proc. Natl. Acad. Sci. USA. vol. 85, pp. 9253–9257.

Markowicz, Sergiusz et al.; "Granulocyte–Macrophage Colony–Stimulating Factor Promotes Differentiation and Survival of Human Peripheral Blood Dendritic Cells in Vitro"; The Journal of Clinical Investigation, vol. 85, No. 3, Mar. 1990, pp 955–961.

Heufler, Christine et al.; "Granulocyte/macrophage Colony—Stimulating Factor and Interleukin 1 Mediate the Maturation of Murine Epidermal Langerhans Cells Into Potent Immunostimulatory Dendritic Cells"; J. Exp. Med., Feb. 1988, vol. 167, pp. 700–705.

Schuler, Gerold et al. "Murine Epidermal Langerhans Cells Mature into Potent Immunostimulatory Dendritic Cells in Vitro"; J. Exp. Med., Mar. 1985, vol. 161, No. 3, pp 526–546.

Romani, N. et al.; "Presentation of Exogenous Protein Antigens by Dendritic Cells to T Cell Clones: Intact Protein is Presented Best by Immature, Epidermal Langerhans Cells"; J. Exp. Med., 1987, 169:1169.

Inaba, Kayo et al.; "An Antigen–independent Contact Mechanism as an Early Step in T–Cell–Proliferative Responses to Dendritic Cells"; J. Exp. Med., 1989, 170;527.

Pure, E. et al., "Antigen Processing by Epidermal Langerhans Cells Correlates with the Level of Biosynthesis of Major Histocompatibility Complex Class II Molecules and Expression of Invariant Chain"; J. Exp. Med., 1990, 172:1459.

Kampgen, E.; et al.; "Class II Major Histocompatibility Complex Molecules of Murine Dendritic Cells: Synthesis, Sialylation of Invariant Chain, and Antigen Processing Capacity are Downregulated upon Culture"; Proc. Natl. Acad. Sci USA, 1991, 88:3014.

Austyn, J.M. et al.; "Migration Patterns of Dendritic Cells in the Mouse. Homing to T Cell–Dependent Areas of Spleen, and Binding within Marginal Zone"; J. Exp. Med., 1988, 167:646.

Larsen, C.P. et al.; "Migration of Dendritic Leukocytes from Cardiac Allografts into Host Spleens: a Novel Pathway for Initiation of Rejection"; J. Exp. Med., 1990, 171:307.

Austyn, J.M.; "Migration Patterns of Dendritic Leukocytes"; Transpl., 1990, 49:1.

Veldman, J.E. et al; Interdigitating Cells. In the Reticuloendothelial System, Morphology. I Carr, and WT. Daems, ed. Plenum Publishing Corp, New York, 1980, 381–416.

Witmer, M.D. et al.; "The Anatomy of Peripheral Lymphoid Organs with Emphasis on Accessory Cells: Light Microscopic, Immunocytochemical Studies of Mouse Spleen, Lymph Node and Peyer's Patch"; Am. J. Anat, 1984, 170:465.

Steinman, R.M. et al; "Identification of a Novel Cell Type in Peripheral Lymphoid Organs of Mice. III. Functional Properties in Vivo"; J. Exp. Med., 1974, 139:1431.

Pugh, C.W. et al.; "Characterization of Nonlymphoid Cells Derived from Rat Peripheral Lymph"; J. Exp. Med., 1983, 157:1758.

Fossum, S.; The Life History of Dendritic Leukocytes (DL). In Current Topics of Pathology. O.H. Ivessen, ed., Springer–Verlag, Berlin, 1989, 101–124.

Katz, S.I. et al.; "Epidermal Langerhans Cells are Derived from Cells Originating in Bone Marrow"; Nature, 1979, 282:324.

Hart, D.N.J et al.; "Demonstration and Characterization of Ia–Positive Dendritic Cells in the Interstitial Connective Tissues of Rat Heart and Other Tissues, But Not Brain", J. Exp. Med., 1981, 154:347.

Reid, C.D.L et al.; "Identification of Hematopoietic Progenitors of Macrophages and Dendritic Langerhans Cells (DL–CFU) in Human Bone Marrow and Peripheral Blood"; Blood, 1990, 76:1139.

Kajigaya, S. et al.; "A Recombinant Murine Granulocyte/macrophage (GM) Colony–Stimulating Factor Derived from an Inducer T Cell Line (IH5.5). Functional Restriction to GM Progenitor Cells"; J. Exp. Med., 1986, 164:1102.

Agger, R. et al.; "The Surface of Dendritic Cells in the Mouse as Studied with Monoclonal Antibodies"; Int. Rev. Immunol, 1990, 6:89.

Crowley, M. et al.; "The Cell Surface of Mouse Dendritic Cells: FACS Analyses of Dendritic Cells from Different Tissues Including Thymus"; Cell. Immuno., Cell. Immunol., 1989, 118:108.

Drexhage, H.A. et al.; "A Study of Cells Present inn Peripheral Lymph of Pigs with Special Reference to a Type of Cell Resembling the Langerhans Cells"; Cell. Tiss. Res., 1979, 202:407.

Romani, N. et al.; Langerhans Cells as Immature Dendritic Cells. CRC Press, Boston, 1991, 191–216.

Romani, N. et al.,; "Ontogeny of Ia–Positive and Thy–1 Positive Leukocytes of Murine Epidermis"; J Invest. Dermatol, 1986, 86:129.

Nussenzweig, M.C. et al.; "A Monoclonal Antibody Specific for Mouse Dendritic Cells", Proc. Natl. Acad. Sci. USA, 1982, 79:161.

Inaba, Kayo et al.; "Dendritic Cells as Antigen Presenting Cells in Vivo", Int. Rev. Immunol, 1990, 6:197.

Barclay, A.N. et al.; "Bone Marrow Origin of Ia–Positive Cells in the Medulla of Rat Thymus"; J. Exp. Med.; 1981, 153:1666.

Rabinowitz, S.S. et al.; "Macrosialin, a Macrophage–Restricted Membrane Sialoprotein Differentially Glycosylated in Response to Inflammatory Stimuli"; J. Exp. Med., 1991, 174:827.

Agger, R. et al.; "Two Populations of Splenic Dendritic Cells Detected with M342, a New Monoclonal to an Intracellular Antigen of Interdigitating Dendritic Cells and Some B Lymphocytes"; J. Leuk. Biol., 1992, 52:34.

Kaplow, L.S.; "Cytochemical Identification of Mononuclear Phagocytes, in 'Manual of Macrophage Methodology'" eds. H.B. Herscowitz, H.T. Holden, J.A. Bellanti and A. Ghaffer. Marcel Dekker, Inc., New York, 1981, 199–207.

Stossel, H. et al.; "Disappearance of Certain Acidic Organelles [Endosomes and Langerhans Cell Granules] Accompanies Loss of Antigen Processing Capacity Upon Culture of Epidermal Langerhans Cells"; J. Exp. Med., 1990, 172:1471.

Crowley, M.T. et al.,; "Use of the Fluorescence Activated Cell Sorter to Enrich Dendritic Cells from Mouse Spleen"; J. Immunol Methods, 1990, 133:55.

Goud, T.J.L.M. et al.; "Identification and Characterization of the Monoblast in Mononuclear Phagocyte Colonies Grown in Vitro"; J. Exp. Med., 1975, 142:1180.

Havenith, C.E.G., et al.; "T Cell Priming in Situ by Intratracheally Instilled Antigen–Pulsed Dendritic Cells"; Am. J. RSP. Cell & Molec. Biol., 1992, submitted.

Liu, L.M. et al.; "Antigen Acquisition by Dendritic Cells: Intestinal Dendritic Cells Acquire Antigen Administered Orally and Can Prime Naïve T Cells 'in vivo'"; J. Exp. Med., In press.

Pancholi, P. et al.; "Presentation of Mycobacterial Antigens by Human Dendritic Cells: Lack of Transfer from Infected Macrophages"; Infection and Immunity submitted.

Cohn, Z.A.; "The Fate of Bacteria within Phagocytic Cells. I. The Degradation of Isotopically Labeled Bacteria by Polymorphonuclear Leucocytes and Macrophages"; J. Exp. Med., 1963, 117:27.

Steinman, R.M. et al.; "The Interaction of Particulate Horseradish Peroxidase (HRP)–anti HRP Immunite Complexes in Mouse Peritoneal Macrophages in Vitro"; J. Cell Biol. 55:616.

Ehrenreich, B.A. et al.; "The Uptake and Digestion of Iodinated Human Serum Albumin by Macrophages in Vitro", J. Exp. Med, 1967, 126:941.

Steinman, R.M. et al.; "The Interaction of Soluble Horseradish Peroxidase in Mouse Peritoneal Macrophages in Vitro"; J. Cell Biol. 55:186.

Cohn, Z.A. et al.; "The Uptake, Storage and Intracellular Hydrolysis of Carbohydrates by Macrophages", J. Exp. Med. 1969, 129:201.

Ehrenreich, B.A. et al.; "The Fate of Peptides Pinocytosed by Macrophages in Vitro"; J. Exp. Med. 1969, 129:227.

Hunt, D.F. et al.; "Peptides Presented to the Immune System by the Murine Class II Major Histocompatibility Complex Molecule l–Ad"; Science, 1992, 256:1817.

Jensen, P.E.; "Protein Synthesis in Antigen Processing"; J. Immunol., 1988, 141:2545.

Harding, C.V. et al.; "Quantitation of Antigent–Presenting Cell MHC Class II/Peptide Complexes Necessary for T–Cell Stimulation"; Nature, 1990, 346:574.

Demotz, S. et al.; "The Minimal Number of Class II MHC–Antigen Complexes Needed for T Cell Activation"; Science, 1990, 249:1028.

Bhardwaj, N. et al.; "Small Amounts of Superantigen on Dendritic Cells are Sufficient to Initiate T Cell Responses". Submitted.

Breel, M. et al.; "Dendritic Cells of the Mouse Recognized by Two Monoclonal Antibodies"; Eur. J. Immunol, 1987, 17:1555.

Fossum, S. et al.; "The Roles of Interdigitating Cells and Natural Killer Cells in the Rapid Rejection of Allogeneic Lymphocytes"; Eur. J. Immunol, 1986, 16:440.

Reis e Sousa, C. et al.; "Phagocytosis of Antigens by Langerhans Cells in Vitro"; J. Exp. Med., In Press., 1993.

Harding, C.V. et al.; "Turnover of la–Peptide Complexes is Facilitated in Viable Antigen–Presenting Cells: Biosynthetic Turnover of IA vs. Peptide Exchange"; Proc. Natl. Acad. Sci USA, 1990, 86:4230.

Brodsky, F.M. et al.,; "The Cell Biology of Antigen Processing and Presentation"; Ann. Rev. Immunol, 1991, 9:707.

Freiden, Thomas R. et al.; "The Emergence of Drug–Resistant Tuberculosis in New York City"; J. of Med. 328:521.

* cited by examiner

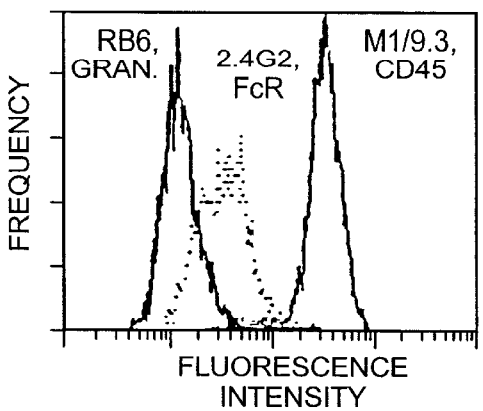
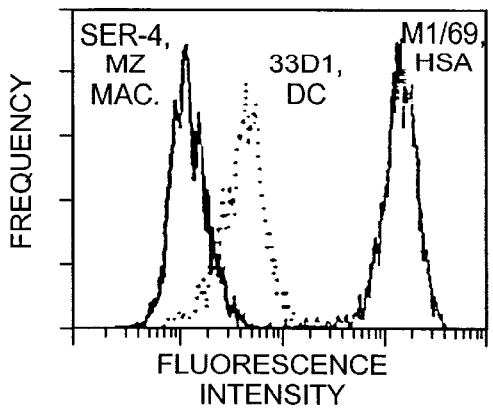
FIG. 2A  FIG. 2B
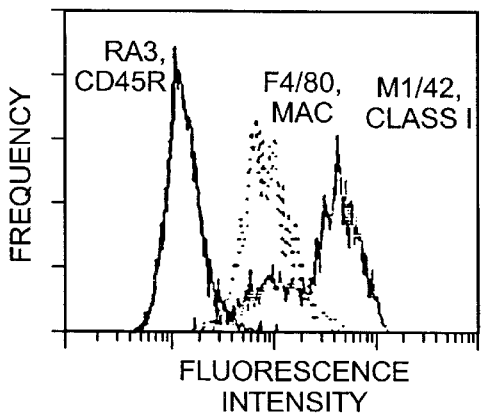
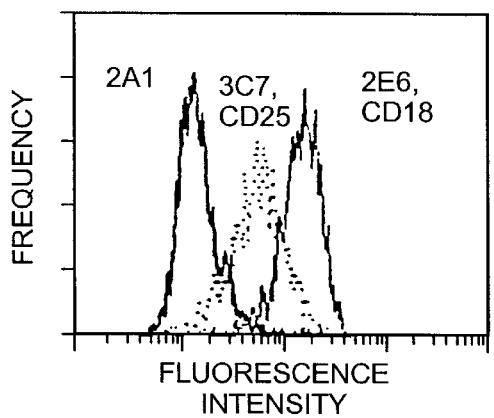
FIG. 2C  FIG. 2D
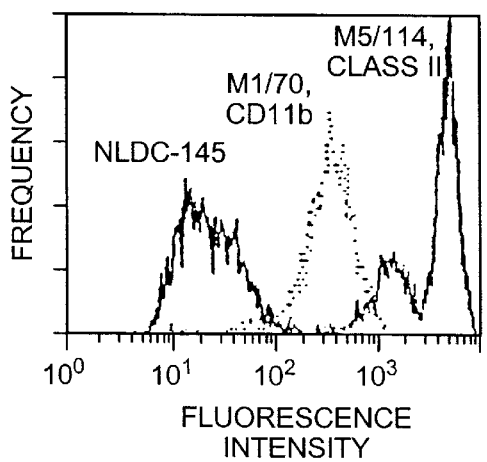
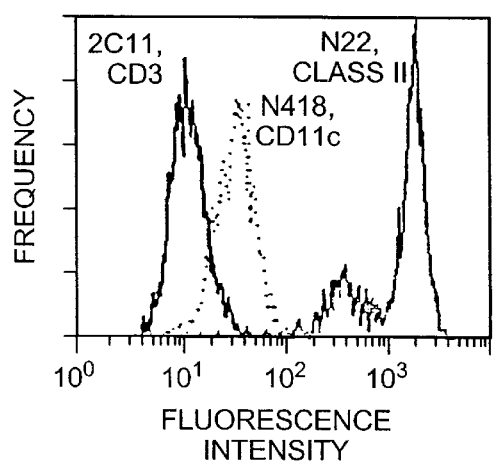
FIG. 2E  FIG. 2F FIG. 13A
FIG. 13B
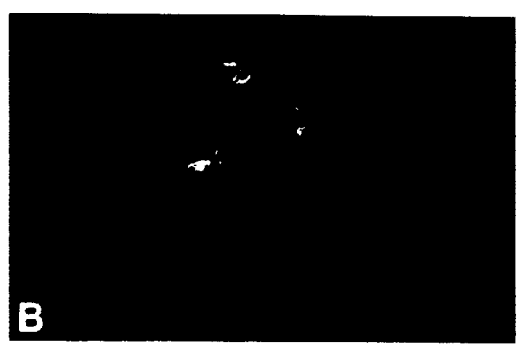
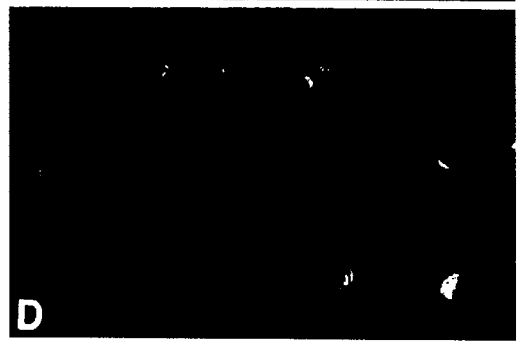
FIG. 13C
FIG. 13D

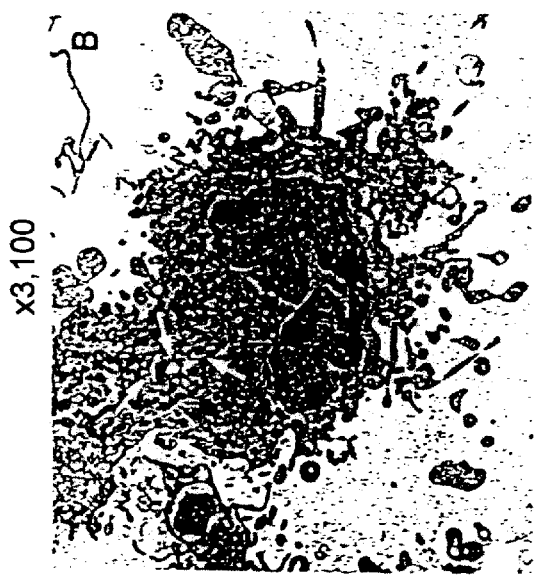
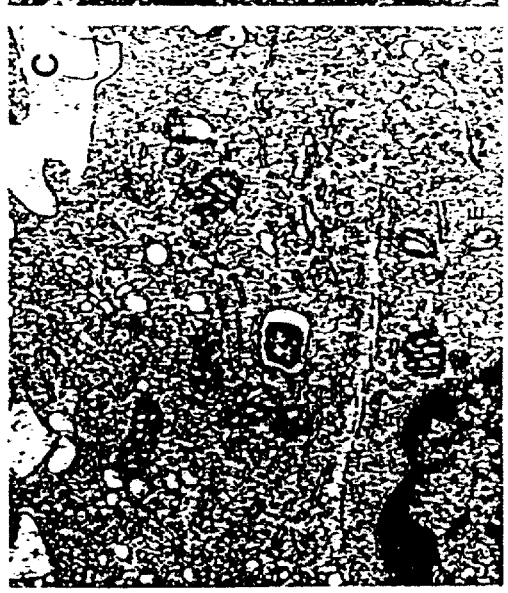
FIG. 14A
FIG. 14B
FIG. 14C
FIG. 14D

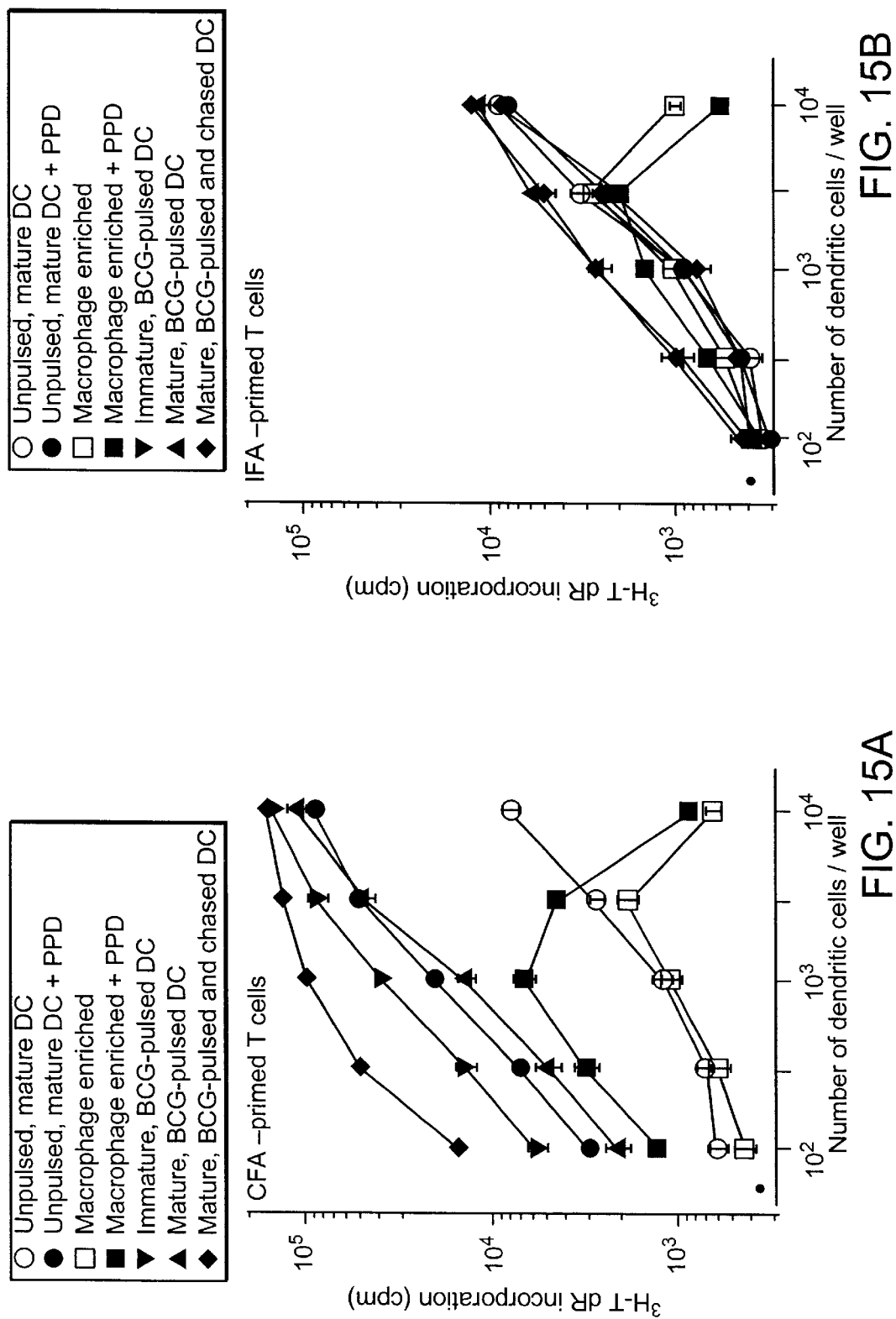

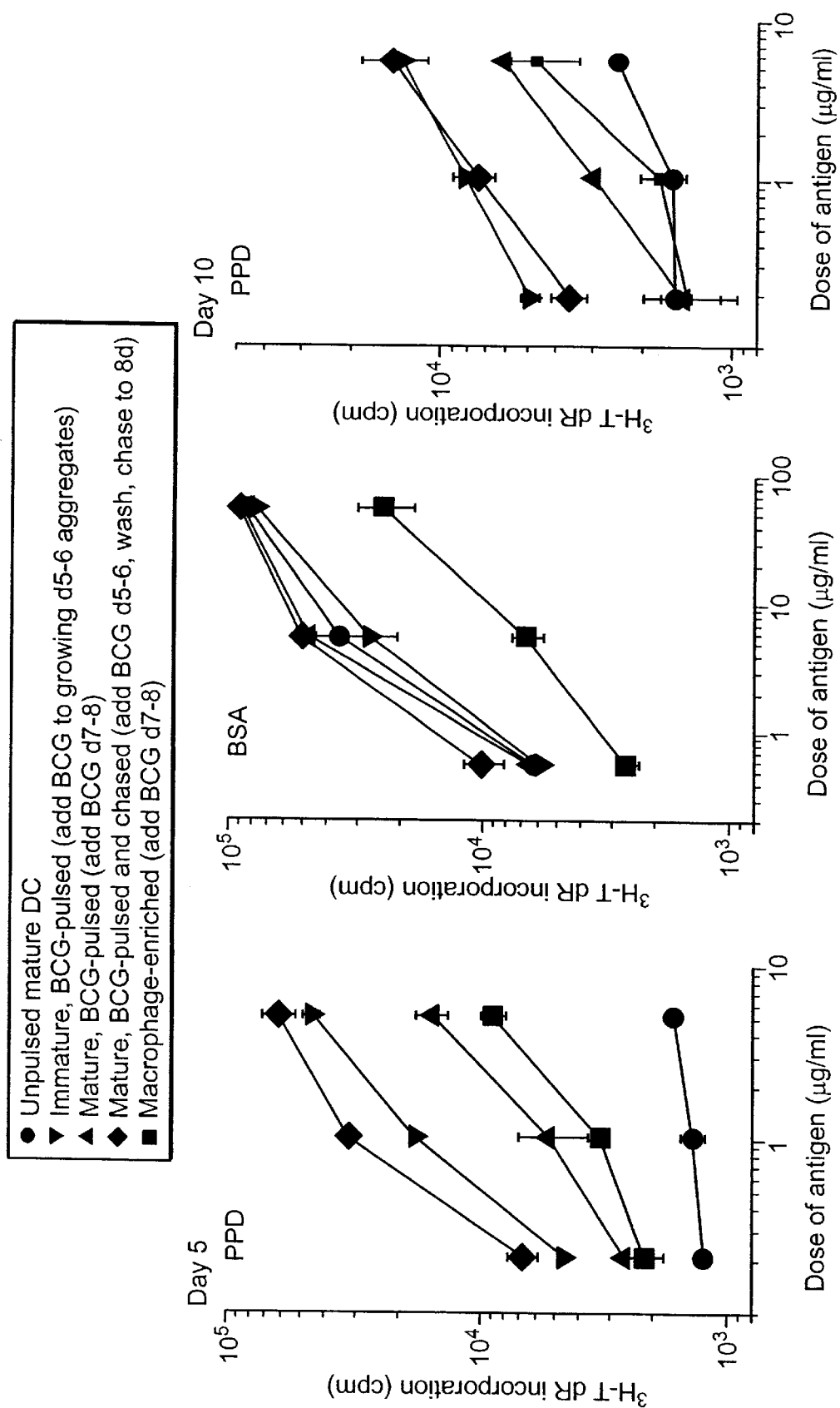

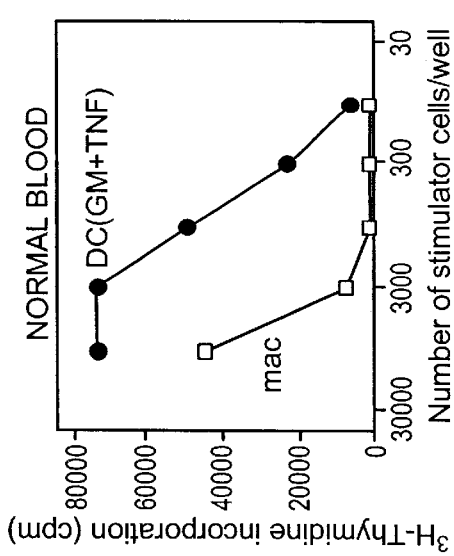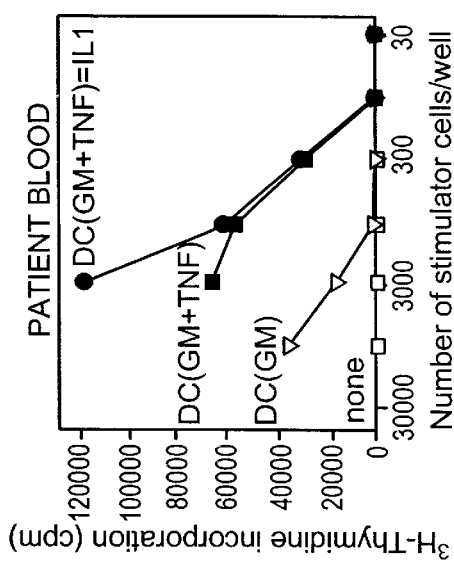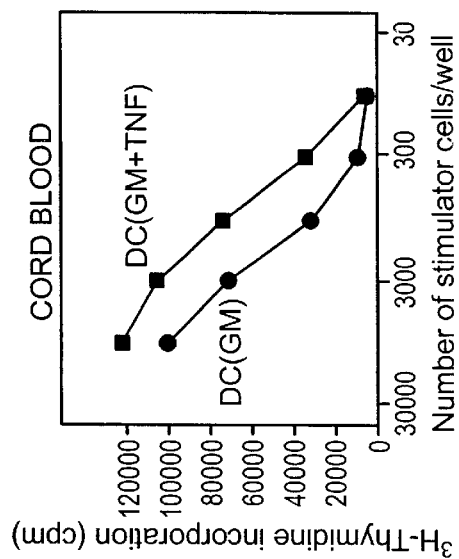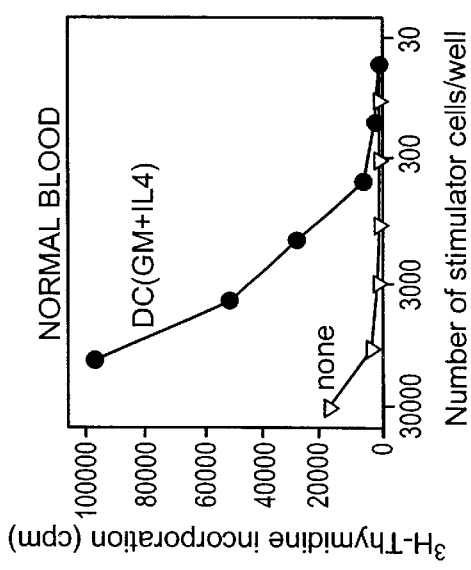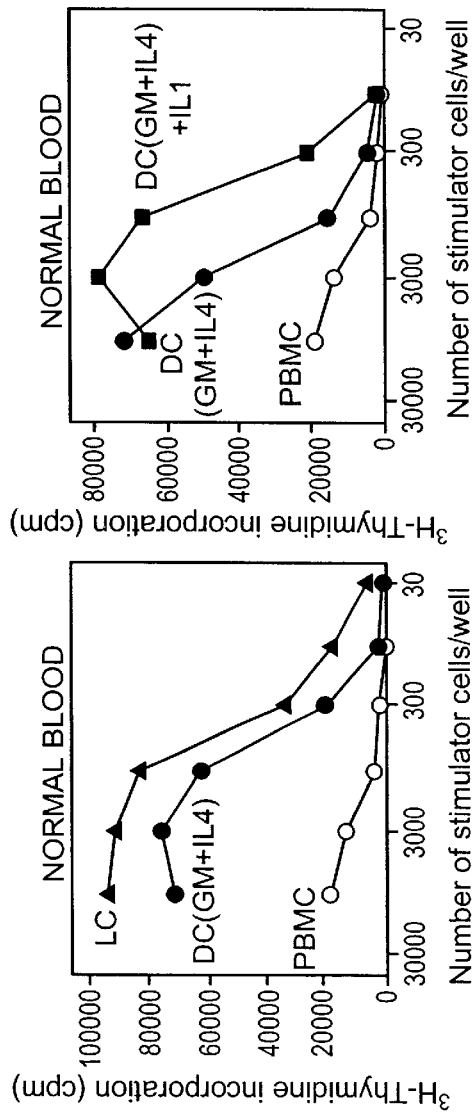

Figure 23A:
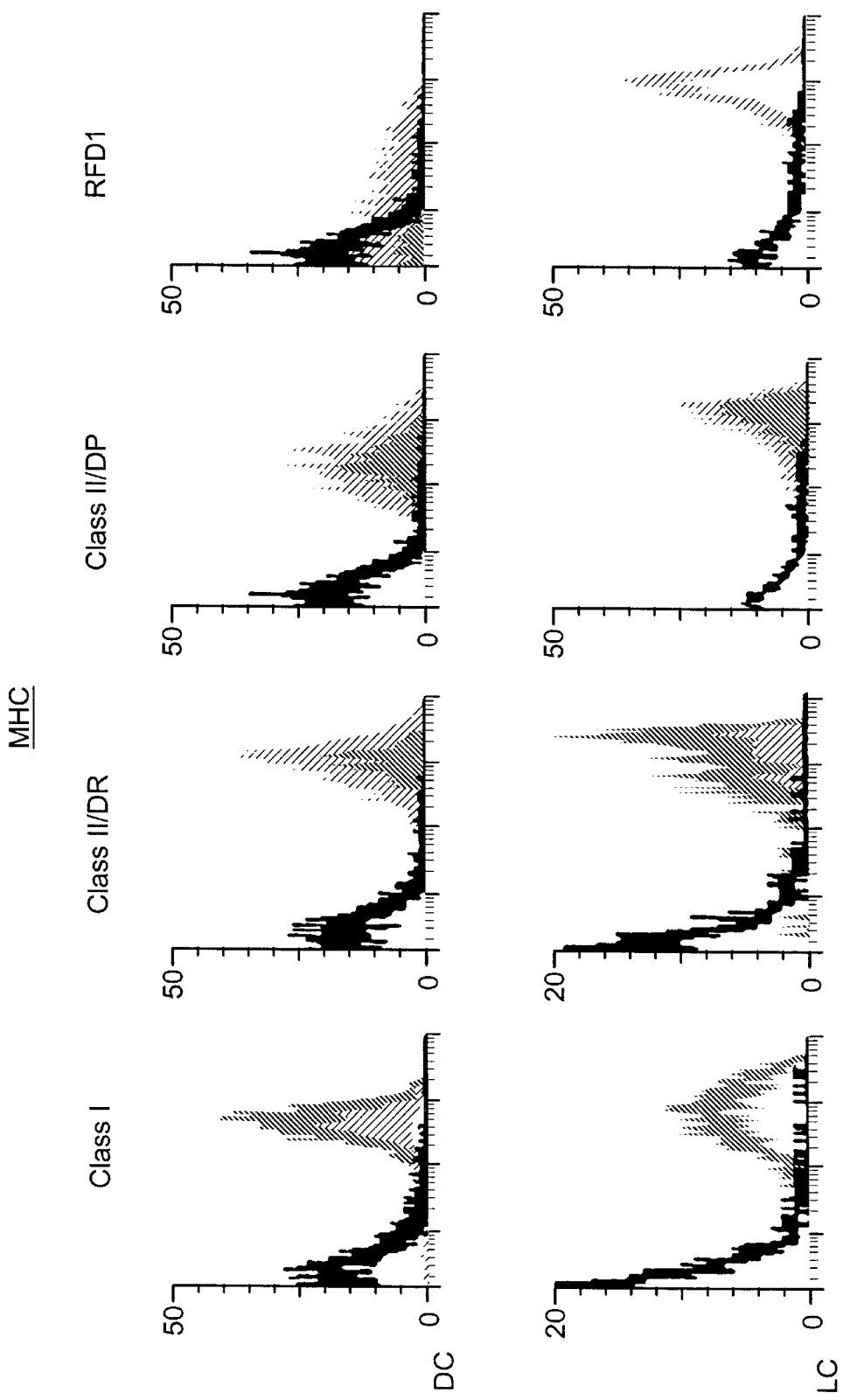
Figure 23B:
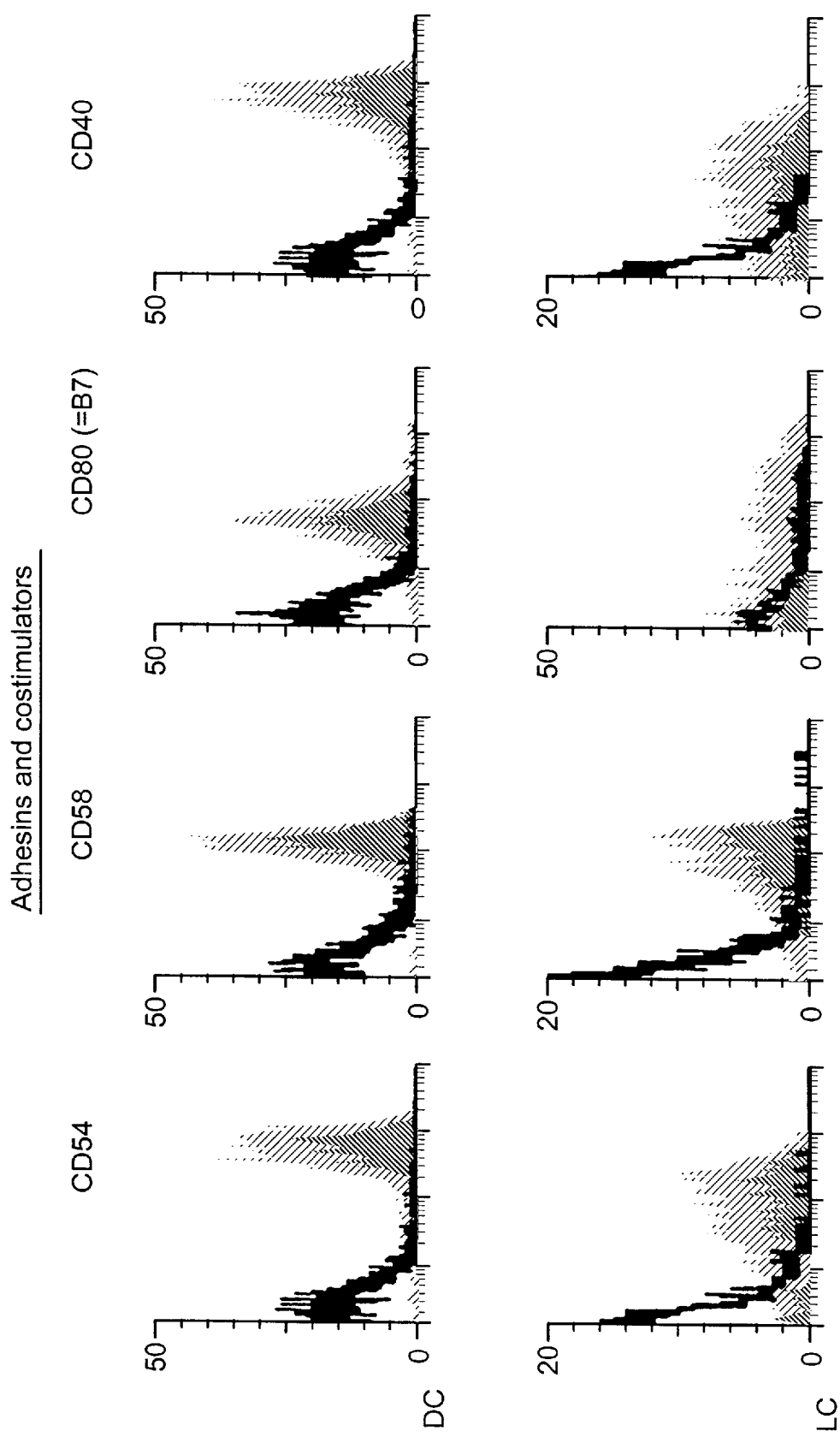
Figure 23C:
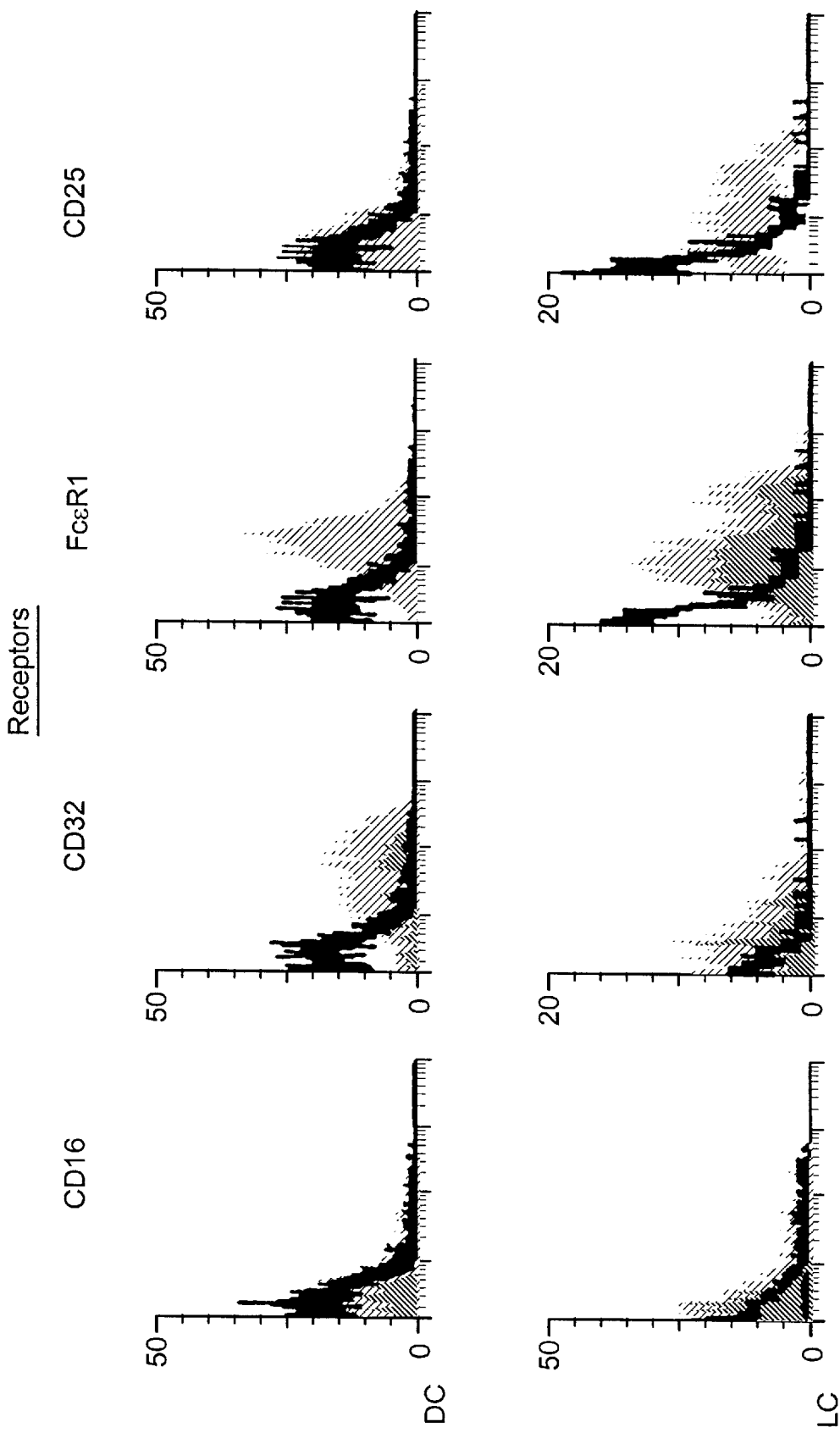
Figure 23D:
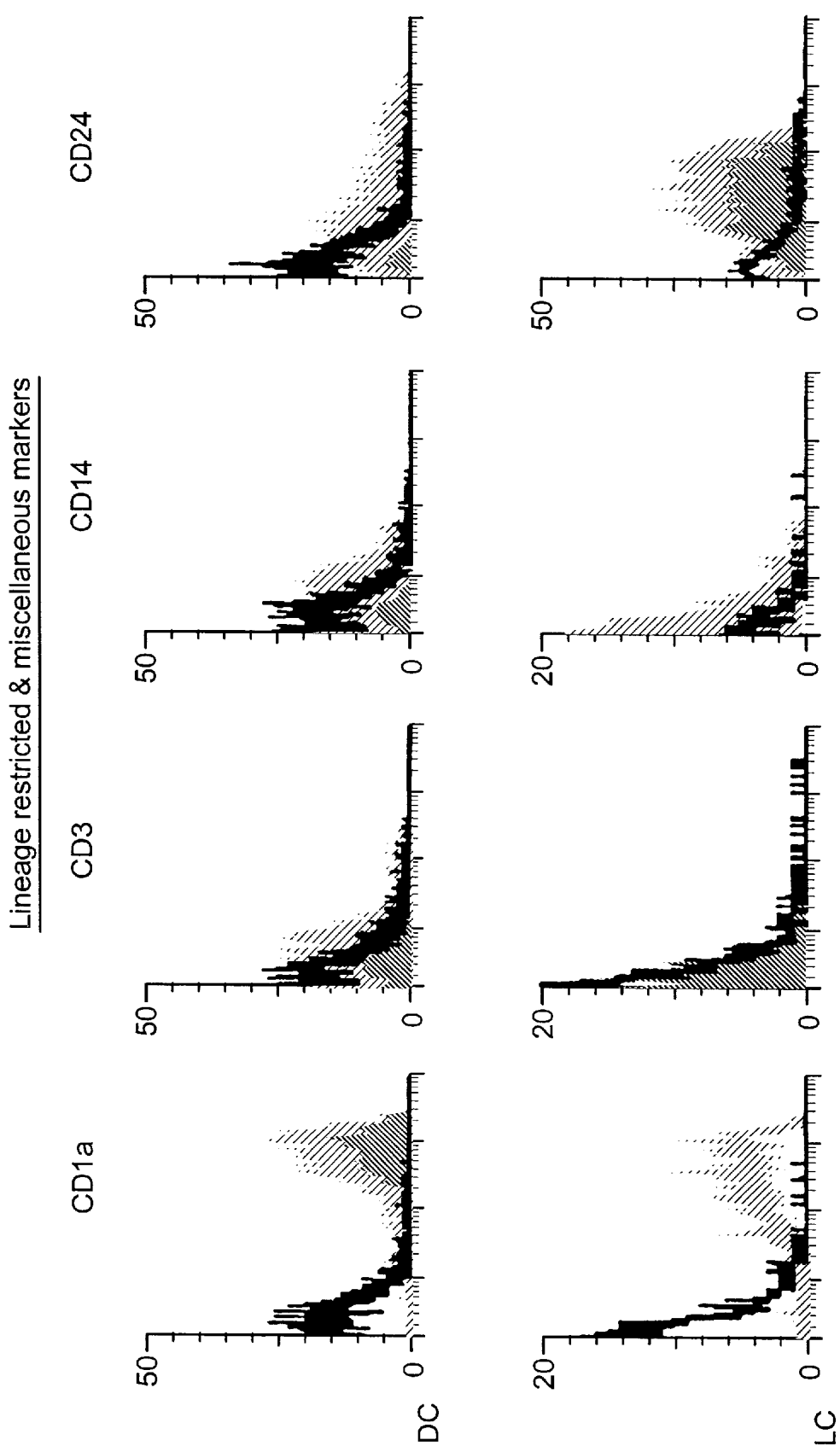
Figure 23E:
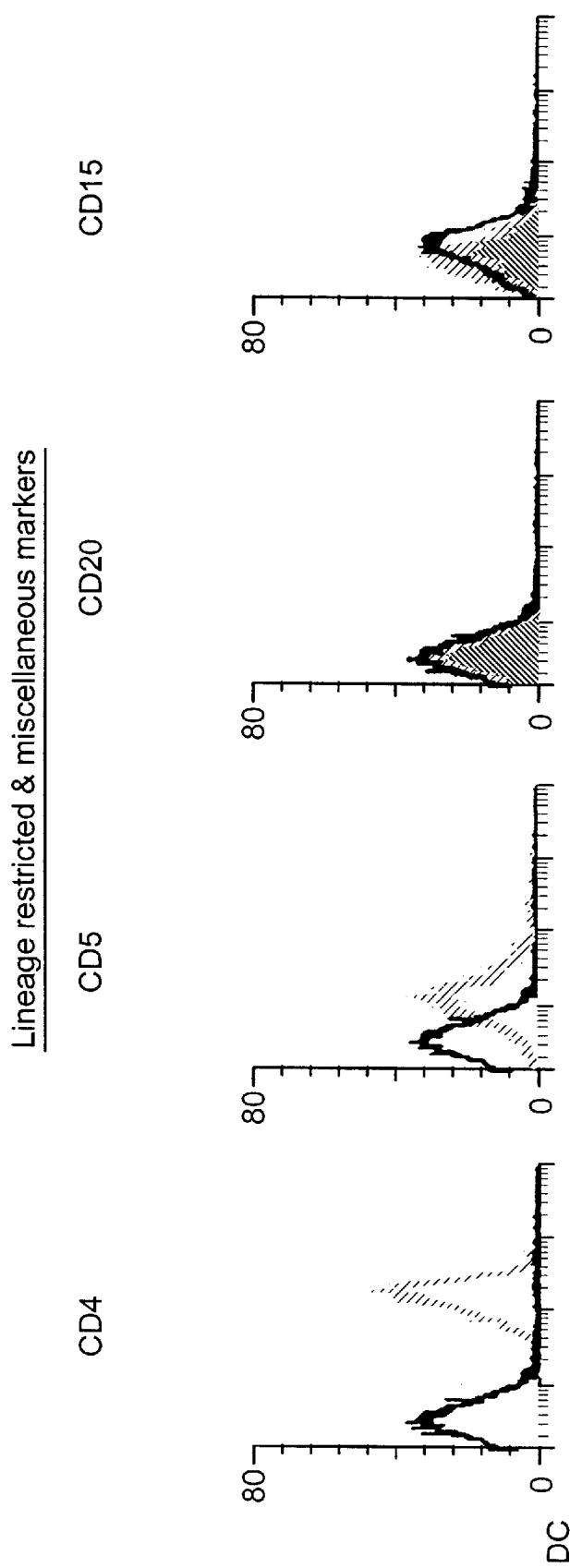
Figure 23F:
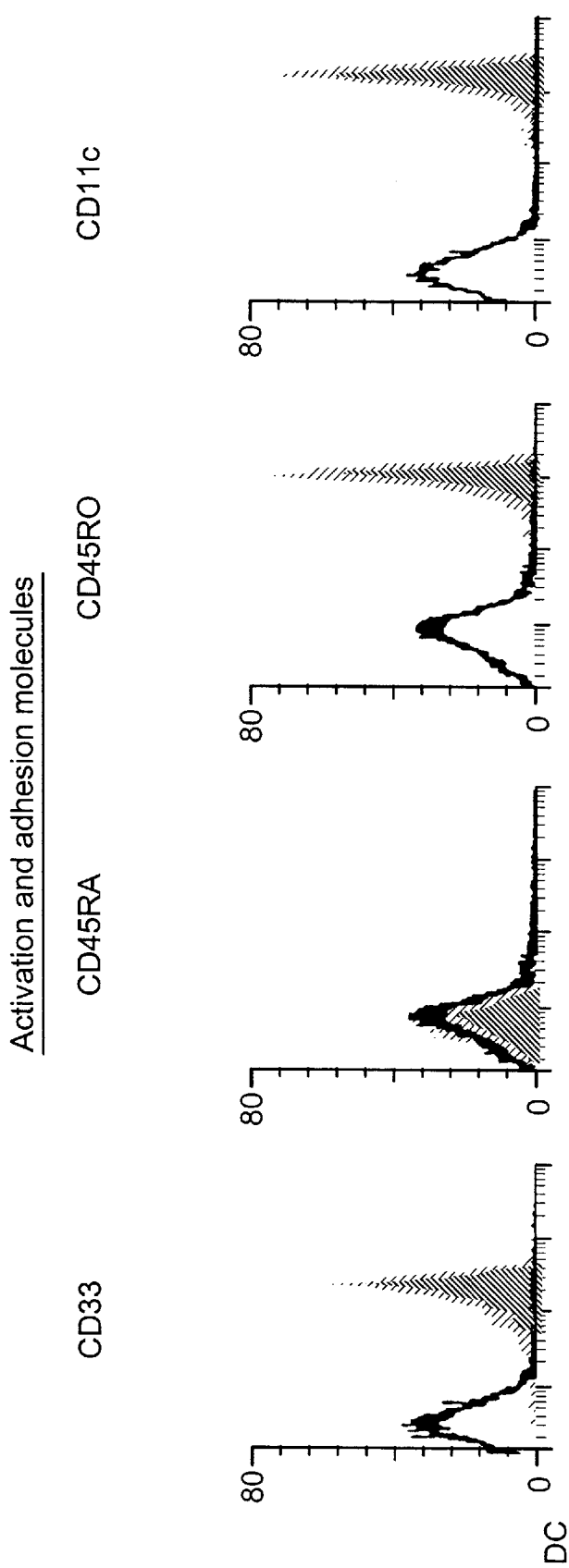

FIG. 22A
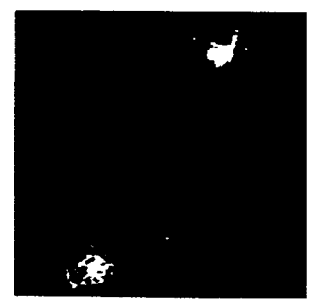
FIG. 22E
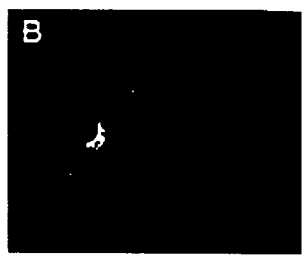
FIG. 22B
FIG. 22F
FIG. 22C
FIG. 22G
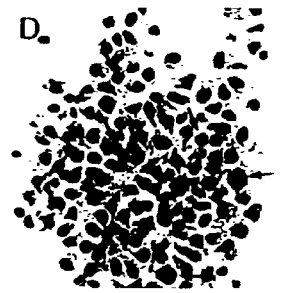
FIG. 22D
FIG. 22H
| FIG. 23A | FIG. 23B |
| --- | --- |
| FIG. 23C | FIG. 23D |
| FIG. 23E | FIG. 23F |
FIG. 23

METHOD FOR IN VITRO PROLIFERATION OF DENDRITIC CELL PRECURSORS AND THEIR USE TO PRODUCE IMMUNOGENS FOR TREATING AUTOIMMUNE DISEASES

This ia a divisional of co-pending application Ser. No. 08/261,537 filed Jun. 17, 1994 which is a CIP of application Ser. No. 08/040,677, filed Mar. 31, 1993, now abandoned, which is a CIP of application Ser. No. 07/981,357, filed Nov. 25, 1992, now abandoned, which is a CIP of application Ser. No. 07/861,612, filed Apr. 1, 1992, now abandoned.

This application is continuation-in-part of U.S. patent application Ser. No. 08/040,677 filed Mar. 31, 1993, which is a continuation-in-part of U.S. patent application Ser. No. 07/981,357 filed Nov. 25, 1992 which in turn is a continuation-in-part of U.S. patent application Ser. No. 07/861,612 filed Apr. 1, 1992.

This invention was made with United States Government support under NIH grant AI13013 awarded by the National Institutes of Health. The United States Government has certain rights in this invention. The making of this invention was also supported by the Austrian Government through grants NB 4370 (Austrian National Bank) and P 8549M (Austrian Science Foundation); and by Austrian National Bank (JUBILAEUMSFONDS PROJECT 4889).

TECHNICAL FIELD OF THE INVENTION

This invention relates to a method of culturing cells of the immune system. In particular a method is provided for culturing proliferating dendritic cell precursors and for their maturation in vitro to mature dendritic cells. This invention also relates to dendritic cell modified antigens which are T cell dependent, the method of making them, and their use as immunogens. Vaccines, methods of immunizing animals and humans using the mature dendritic cells of the invention, and the modified antigens are also described.

BACKGROUND OF THE INVENTION

The immune system contains a system of dendritic cells that is specialized to present antigens and initiate several T-dependent immune responses. Dendritic cells are distributed widely throughout the body in various tissues. The distribution of dendritic cells has been reviewed in (1). Dendritic cells are found in nonlymphoid organs either close to body surfaces, as in the skin and airways, or in interstitial regions of organs like heart and liver. Dendritic cells, possibly under the control of the cytokine granulocyte macrophage colony-stimulating factor, (hereinafter GM-CSF), can undergo a maturation process that does not entail cell proliferation (2,3). Initially, the dendritic cells process and present antigens most likely on abundant, newly synthesized MHC class II molecules, and then strong accessory and cell-cell adhesion functions are acquired (4–7). Dendritic cells can migrate via the blood and lymph to lymphoid organs (8–10). There, presumably as the "interdigitating" cells of the T-area (8,11–13), antigens can be presented to T cells in the recirculating pool (14). However, little is known about the progenitors of dendritic cells in the different compartments outlined above.

The efficacy of dendritic cells in delivering antigens in such a way that a strong immune response ensues i.e., "immunogenicity", is widely acknowledged, but the use of these cells is hampered by the fact that there are very few in any given organ. In human blood, for example, about 0.1% of the white cells are dendritic cells (25) and these have not been induced to grow until this time. Similarly, previous studies (20, 21) have not reported the development, in culture, of large numbers of dendritic cells from bone marrow. A more recent report described the development of dendritic cells in GM-CSF supplemented marrow cultures, however no documentation as to the origin of the dendritic cells or use of proliferating aggregates as an enriched source of dendritic cells was observed. (Scheicher et al. (1992)) *J. Immunol. Method.* 154:253–264. While dendritic cells can process foreign antigens into peptides that immunologically active T cells must recognize (4,6,7,14) i.e., dendritic cells accomplish the phenomenon of "antigen presentation", the low numbers of dendritic cells prohibits their use in identifying immunogenic peptides.

Dendritic cells in spleen (15) and afferent lymph (16,17) are not in the cell cycle but arise from a proliferating precursor. Ultimately, dendritic cells emanate from the bone marrow (15,16,18,19), yet it has been difficult to generate these cells in culture except for two reports describing their formation in small numbers (20,21). Although a bone marrow precursor cell has been reported, conditions have not been reported that direct its proliferation in culture (Steinman, R. (1991)) "The Dendritic Cell System and Its Role In Immunogenicity", *Ann. Rev. Immunol.*, 9:271–96. Identification of proliferating dendritic cells in bone marrow, in contrast to blood, is difficult because there are large numbers of granulocytes that develop in, response, to GM-CSF and these crowd the immature dendritic cell cultures, preventing maturation of the dendritic precursors. The use of cell surface markers to enrich bone marrow dendritic cell precursors has been reported to result in only modest increases because the markers are also expressed by numerous non-dendritic bone marrow cells (Bowers, W. E. and Goodell (1989)), "Dendritic Cell Ontogeny" *Res. Immunol.* 140:880–883.

Relatively small numbers of dendritic cells have also been isolated from blood (Vakkila J. et al. (1990) "Human Peripheral blood-derived dendritic cells do not produce interleukin 1α, interleukin 1β, or interleukin 6" *Scand. J. Immunol.* 31:345–352; Van Voorhis W. C. et al., (1982) "Human Dendritic Cells", *J. Exp. Med.*, 1172–1187.) However, the presence in blood of dendritic cell precursors has not been reported and as recently as 1989 the relationship between blood dendritic cells and mature dendritic cells in other tissues was uncertain. Furthermore, it was recognized that dendritic cells are "rare and difficult to isolate and have not as yet been shown to give rise to DC [dendritic cells] in peripheral tissues." (MacPherson G. G. (1989) "Lymphoid Dendritic cells: Their life history and roles in immune responses", *Res. Immunol.* 140:877–926).

Granulocyte/macrophage colony-stimulating factor (GM-CSF) is a factor which modulates the maturation and function of dendritic cells. (Witmer-Pack et al, (1987) "Granulocyte/macrophage colony-stimulating factor is essential for the viability and function of cultured murine epidermal Langerhans cells". *J.Exp.Med.* 166:1484–1498; Heufler C. et al., (1988) "Granulocyte/macrophage colony-stimulating factor and interleukin 1 mediate the maturation of murine epidermal Langerhans cells into potent immunostimulatory dendritic cells", *J. Exp. Med.* 167:700–705). GM-CSF stimulated maturation of dendritic cells in vitro suggests that the presence of GM-CSF in a culture of dendritic cell precursors would mediate maturation into immunologically active cells, but the important goal of achieving extensive dendritic cell growth has yet to be solved.

T-dependent immune responses are characterized by the activation of T-helper cells in the production of antibody by B cells. An advantage of T-dependent over T-independent immune responses is that the T-dependent responses have memory, i.e. cells remain primed to respond to antigen with rapid production of antibody even in the absence of antigen and the immune response is therefore "boostable". T-independent immune responses are, in contrast, relatively poor in children and lack a booster response when a T-independent antigen is repeatedly administered. The immunologic memory of T cells likely reflects two consequences of the first, "primary" or "sensitizing" limb of the immune response: (a) an expanded number of antigen-specific T cells that grow in response to antigen-bearing dendritic cells, and (b) the enhanced functional properties of individual T cells that occurs after dendritic cell priming (Inaba et al., (1984) Resting and sensitized T lymphocytes exhibit distinct stimulatory (antigen presenting cell) requirements for growth and lymphokine release; *J.Exp.Med.* 160:868–876; Inaba and Steinman, (1985) "Protein-specific helper T lymphocyte formation initiated by dendritic cells", *Science* 229: 475–479; Inaba et al., (1985) "Properties of memory T lymphocytes isolated from the mixed leukocyte reaction", *Proc.Natl.Acad.Sci.* 82:7686–7690).

Certain types of antigens characteristically elicit T-cell dependent antibody responses whereas others elicit a T-cell independent response. For example, polysaccharides generally elicit a T-cell independent immune response. There is no memory response and therefore no protection to subsequent infection with the polysaccharide antigen. Proteins, however, do elicit a T-cell dependent response in infants. The development of conjugate vaccince containing a polysaccharide covalently coupled to a protein converts the polysaccharide T-independent response to a T-dependent response. Unfortunately, little is known concerning the sites on proteins which confer their T-cell dependent character, therefore hampering the design of more specific immunogens.

As stated above, dendritic cells play a crucial role in the initiation of T-cell dependent responses. Dendritic cells bind and modify antigens in a manner such that the modified antigen when presented on the surface of the dendritic cell can activate T-cells to participate in the eventual production of antibodies. The modification of antigens by dendritic cells may, for example, include fragmenting a protein to produce peptides which have regions which specifically are capable of activating T-cells.

The events whereby cells fragment antigens into peptides, and then present these peptides in association with products of the major histocompatibility complex, (MHC) are termed "antigen presentation". The MHC is a region of highly polymorphic genes whose products are expressed on the surfaces of a variety of cells. MHC antigens are the principal determinants of graft rejection. Two different types of MHC gene products, class I and class II MHC molecules, have been identified. T cells recognize foreign antigens bound to only one specific class I or class II MHC molecule. The patterns of antigen association with class I or class II MHC molecules determine which T cells are stimulated. For instance, peptide fragments derived from extra cellular proteins usually bind to class II MHC molecules, whereas proteins endogenously transcribed in dendritic cells generally associate with newly synthesized class I MHC molecules. As a consequence, exogenously and endogenously synthesized proteins are typically recognized by distinct T cell populations.

Dendritic cells are specialized antigen presenting cells in the immune response of whole animals (14,31). Again however, the ability to use dendritic cells to identify and extract the immunogenic peptides is hampered by the small numbers of these specialized antigen presenting cells.

Particle uptake is a specialized activity of mononuclear and polymorphonuclear phagocytes. Dead cells, immune complexes, and microorganisms all are avidly internalized. Following fusion with hydrolase-rich lysosomes, the ingested particles are degraded (60,61). This degradation must be to the level of permeable amino acids (62,63) and saccharides, otherwise the vacuolar apparatus would swell with indigestible materials (64,65). Such clearance and digestive functions of phagocytes contribute to wound healing, tissue remodeling, and host defense.

Another consequence of endocytosis, the processing of antigens by antigen presenting cells (APCs), differs in many respects from the scavenging function of phagocytosis. First, processing requires the generation of peptides at least 8–18 amino acids in length (66,67), while scavenging entails digestion to amino acids (62,63). Secondly, presentation requires the binding of peptides to MHC class II products (6,68), whereas scavenging does not require MHC products. Thirdly, antigen presentation can function at a low capacity, since only a few hundred molecules of ligand need to be generated for successful stimulation of certain T-T hybrids (69,70) and primary T cell populations (71). During scavenging, phagocytes readily clear and destroy hundreds of thousands of protein molecules each hour (63). Lastly, antigen presentation is best carried out by cells that are rich in MHC class II but show little phagocytic activity and few lysosomes, i.e., dendritic cells and B cells, while phagocytes (macrophages and neutrophils) often have low levels of class II and abundant lysosomes. These observations, together with the identification of antigenic specializations within the endocytic system of dendritic cells and B cells, have lead to the suggestion that the machinery required for antigen presentation may differ from that required for scavenging, both quantitatively and qualitatively (31).

In the case of dendritic cells, there have been indications that these APCs are at some point during their lifetime capable of phagocytic activity. Pugh et al. noted Feulgen-stained inclusions in some afferent lymph dendritic cells and suggested that phagocytosis of other cells had taken place prior to entry into the lymph (16). Fossum noted phagocytic inclusions in the interdigitating dendritic cells of the T cell areas in mice that were rejecting allogeneic leukocytes (71). Reis e Sousa et al. (74) found that freshly isolated epidermal Langerhans cells, which are immature but nonproliferating dendritic cells, internalize small amounts of certain particulates. Neither report, however, demonstrates or suggests the occurrence of phagocytosis when particles are administered to cultures of proliferating dendritic cells.

Injection of dendritic cells pulsed with pathogenic lymphocytes into mammals to elicit an active immune response against lymphoma is the subject of PCT patent application WO91/13632. In addition, Francotte and Urbain, *Proc. Nat'l. Acad. Sci. USA* 82:8149 (1985) reported that mouse dendritic cells, pulsed in vitro with virus and injected back into mice, enhances the primary response and the secondary response to the virus. Neither the report by Francotte and Urbain and patent application WO 91/13632 provide a practical method of using dendritic cells as an adjuvant to activate the immune response because both of these methods depend on dendritic cells obtained from spleen, an impractical source of cells for most therapies or immunization procedures. In addition, neither report provides a method to obtain dendritic cells in sufficient quantities to be clinically useful.

SUMMARY OF THE INVENTION

This invention provides a method of producing a population of dendritic cell precursors from proliferating cell cultures. The method comprises (a) providing a tissue source comprising dendritic cell precursors; (b) treating the tissue source from (a) to increase the proportion of dendritic cell precursors to obtain a population of cells suitable for culture in vitro; (c) culturing the tissue source on a substrate in a culture medium comprising GM-CSF, or a biologically active derivative of GM-CSF, to obtain proliferating nonadherent cells and cell clusters; (d) subculturing the nonadherent cells and cell clusters to produce cell aggregates comprising proliferating dendritic cell precursors; and (e) serially subculturing the cell aggregates one or more times to enrich the proportion of dendritic cell precursors.

In another embodiment of this invention, cells may be cultured in the presence of factors which increases the proportion of dendritic cell precursors by inhibiting the proliferation or maturation of non-dendritic cell precursors.

For example, cells may be cultured in the presence of factors which inhibit macrophage proliferation and/or maturation. Such a factor should be provided in an amount sufficient to promote the proliferation of dendritic cells while inhibiting the proliferation and/or maturation of macrophage precursor cells or macrophages. Examples of such agents include Interleukin-4 (IL-4) and Interleukin-13 (IL-13). These agents are particularly useful for culturing cells from preferred tissue sources such as blood, and more preferably specifically human blood isolated from healthy individuals.

This invention also provides a method of producing in vitro mature dendritic cells from proliferating cell cultures. The method comprises (a) providing a tissue source comprising dendritic cell precursor cells; (b) treating the tissue source from (a) to increase the proportion of dendritic cell precursors in order to obtain a population of cells suitable for culture in vitro; (c) culturing the tissue source on a substrate in a culture medium comprising GM-CSF, or a biologically active derivative of GM-CSF, to obtain non-adherent cells and cell clusters; (d) subculturing the nonadherent cells and cell clusters to produce cell aggregates comprising proliferating dendritic cell precursors; (e) serially subculturing the cell aggregates one or more ties to enrich the proportion of dendritic cell precursors; and (f) continuing to culture the dendritic cell precursors for a period of time sufficient to allow them to mature into mature dendritic cells.

To reduce the proportion of non-dendritic precursor cells, the tissue source may be pretreated prior to culturing the tissue source on a substrate to obtain the non-adherent cells or during the early stages of the culture. Preferred tissue sources for the practice of the invention are bone marrow and, in particular, blood.

This invention also provides a method of increasing the proportion of dendritic cells present in the tissue source by pretreating the individual with a substance to stimulate hematopoiesis.

When bone marrow is used as the tissue source the pretreatment step comprises killing cells expressing antigens which are not expressed on dendritic precursor cells by contacting the bone marrow with antibodies specific for antigens not present on dendritic precursor cells in a medium comprising complement. Removal of undesirable non-dendritic cell precursors may also be accomplished by adsorbing the undesirable non-dendritic or their precursor cells onto a solid support.

This invention also provides dendritic cell precursors and dendritic cells in amounts which may be used therapeutically and which also may be used to prepare new therapeutic antigens. In addition, the dendritic cell precursors and dendritic cells prepared according to the method of this invention are also provided.

Another embodiment of the invention are antigen-activated dendritic cells prepared according to the method of the invention in which antigen-activated dendritic cells have been exposed to antigen and express modified antigens for presentation to and activation of T cells.

This invention also provides novel antigens which are produced by exposing an antigen to cultures of dendritic cells prepared according to the method of the invention in which the antigen is modified by the dendritic cells to produce modified antigens which are immunogenic fragments of the unmodified or native antigen and which fragments activate T cells.

These novel antigens may be used to immunize animals and humans to prevent or treat disease.

This invention also provides a method of preparing antigens from dendritic cell precursors comprising providing precursor dendritic cells from a population of precursor cells capable of proliferating, contacting the precursor cells with antigen for a period of time sufficient to allow the dendritic cell precursors to phagocytose the antigen and obtain antigen-containing dendritic cell precursors; culturing the antigen containing-dendritic cell precursors under conditions and for a period of time sufficient for the antigen to be processed and presented by dendritic cell precursors.

The antigens processed by the dendritic cell precursors as a result of phagocytosis may themselves be used alone or in combination with adjuvants including dendritic cell precursors to evoke an immune response in an individual to the antigen.

Also provided are compositions and methods for increasing the number of myeloic dendritic progenitor cells in blood in those individuals.

In a further embodiment, the yield of dendritic cell precursors is increased by culturing the precursors in a sufficient amount of GM-CSF and other cytokines to promote proliferation of the dendritic cell precursors. Other cytokines include but are not limited to G-CSF, M-CSF, TNF-α, Interleukin-3, and Interleukin-1α, Interleukin-1β, Interleukin 6, Interleukin-4, Interleukin-13 and stem cell factor.

In another embodiment, the invention provides self-peptide antigens produced by pulsing the dendritic cells of the invention with a protein to which an individual has developed an immune response and extracting the relevant self-peptide or autoantigen.

This invention also provides a method of treating autoimmune diseases by treating an individual with therapeutically effective amounts of self-peptides produced according to the method of the invention to induce tolerance to the self-proteins.

The treatment of autoimmune diseases comprising administering to an individual in need of treatment a therapeutically effective amount of antigen-activated dendritic cells where the antigen is a self-protein or autoantigen is also provided.

The use of the compositions and methods of the invention to treat autoimmune diseases selected from the group of juvenile diabetes, myasthenia gravis, and multiple sclerosis is also provided.

This invention also provides treatment for inflammatory diseases in which the pathogenesis involves exaggerated T cell mediated immune responses such as those present in atopic dermatitis and contact dermatitis.

This invention also provides a method for providing an antigen to a host comprising exposing an antigen to a culture of dendritic cells prepared according to the method of this invention to produce antigen-activated dendritic cells followed by inoculating the host with the antigen-activated dendritic cells.

This invention further provides a method of activating T cells comprising the use of proliferating dendritic cells for capturing protein, viral, and microbial antigens in an immunogenic form in situ and then presenting these antigens in a potent manner to T cells either in vitro or in situ.

This invention additionally provides a method comprising the use of mature and precursor dendritic cells to present MHC class I and II products with antigen peptides.

This invention also provides a method for making antigenic peptides that are specific for an individual's MHC products thereby increasing the number of specialized stimulatory antigenic presenting cells available to provide an immunogenic response in an individual.

Also provided are compositions and methods to treat infectious diseases, including but not limited to diseases caused by mycobacteria including tuberculosis, bacteria, and viruses.

Compositions and methods for using dendritic cells or dendritic cell precursors as vehicles for active immunization and immunotherapy in situ are also provided.

Vaccines comprised of any of the antigens or antigen-activated dendritic cells described above are also provided as are the methods of immunizing against disease in humans or animals comprising administering any of the compositions of the invention.

An object of this invention is to provide a method of culturing dendritic cell precursors in vitro so that they evolve into mature dendritic cells suitable for use as immunogens or adjuvants when combined with an antigen.

It is also an object of this invention to provide dendritic cell precursors capable of phagocytosing antigenic material to be processed and presented by the dendritic cell precursors.

Another object of this invention is to provide a convenient and practical source of sufficient quantities of dendritic cells and dendritic cell precursors to be useful in the treatment or prevention of disease.

Another object of this invention is to provide novel immunogens comprising the dendritic cells or dendritic cell precursors of this invention which have been exposed to antigen and express modified antigen on their surface.

Another object of this invention is to provide antigens which have been modified through their exposure to dendritic cell precursors or dendritic cells and which modified antigens are effective as T-cell dependent antigens.

A further objective of the invention is to provide a method of immunizing individuals with T-cell dependent antigens for the prevention and treatment of disease.

FIGURE LEGENDS

FIG. 1. Flow plan for inducing dendritic cell "colonies."

FIG. 2. FIG. 2 comprises FIGS. 2A through 2F which are FACS analyses of dendritic cells released from proliferating aggregates. Several mAbs which recognize various cell surface determinants on dendritic cell precursors (23,24,28) are shown. Except for MHC class I and II products, the phenotype of the released cells is homogeneous. The staining with no primary mAb was identical to RB6 and RA3.

FIG. 3. FIG. 3, comprises FIGS. 3A through 3F which are FACS analyses of dendritic cell precursors that could be dislodged by Pasteur pipetting of proliferating aggregates, (3A, 3B and 3C) and dendritic cells released spontaneously (3D, 3E and 3F) in culture. The mAb are: M1/42 anti-MHC class I [ATCC # TIB 126]; NLDC145 anti-interdigitating cell (13); M5/114 anti-MHC class II [ATCC # TIB 120]; 33D1 anti-dendritic cell [ATCC # TIB 227]; B5-5 anti-thy-1. The staining with anti-MHC mabs is bimodal, but the released cell fraction of dendritic cells is richest in expression of MHC class I and II.

Figure 4:
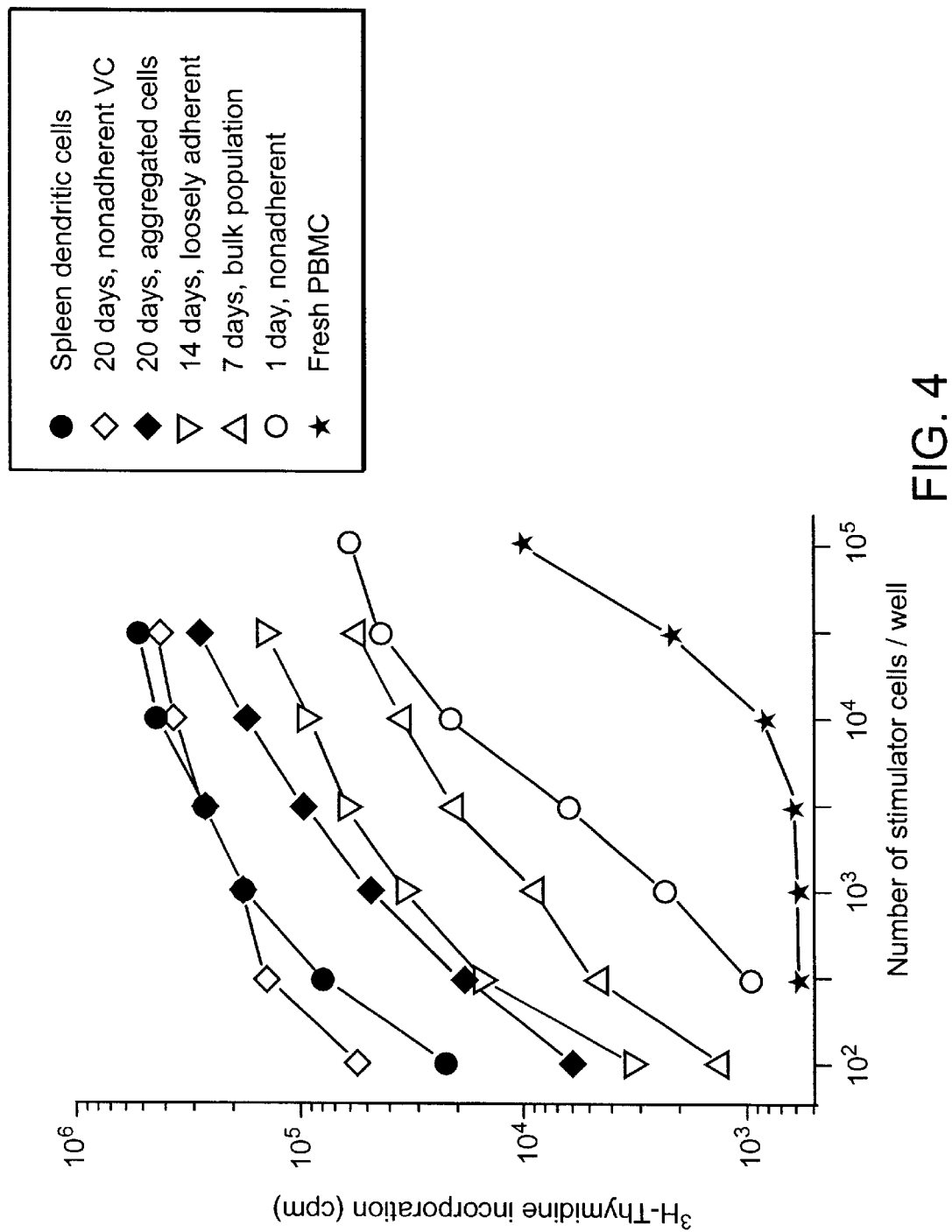

FIG. 4. MLR stimulating activity of populations isolated from the GM-CSF stimulated mouse blood cultures [see text].

Figure 5B:
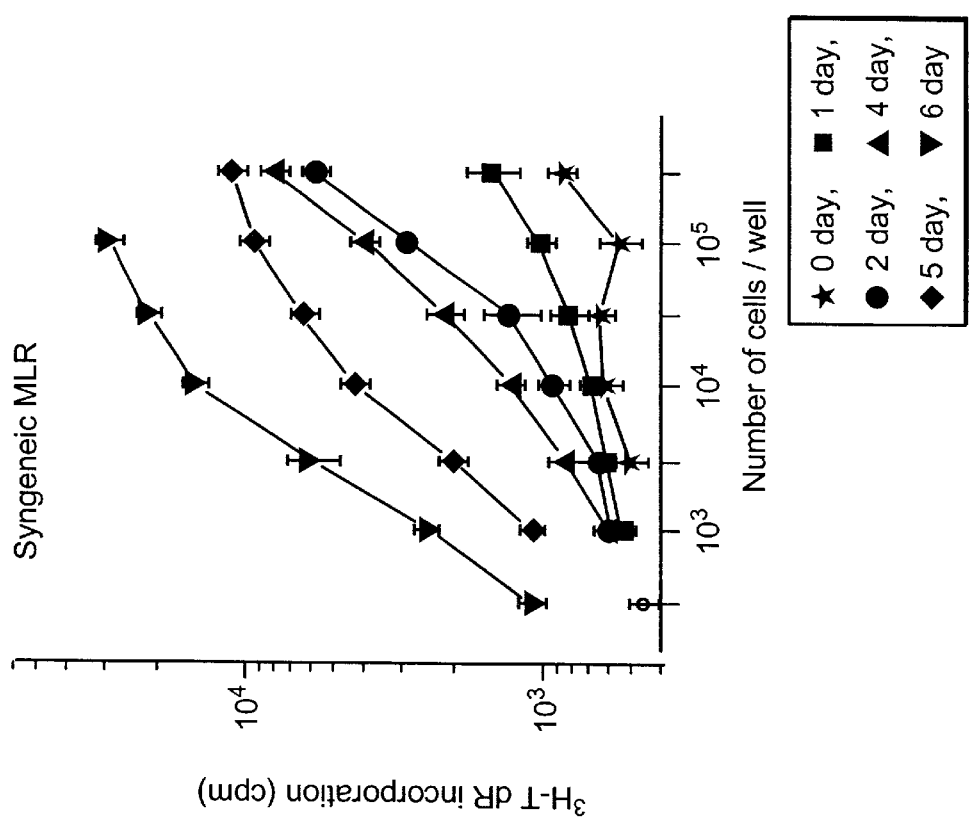
Figure 5A:
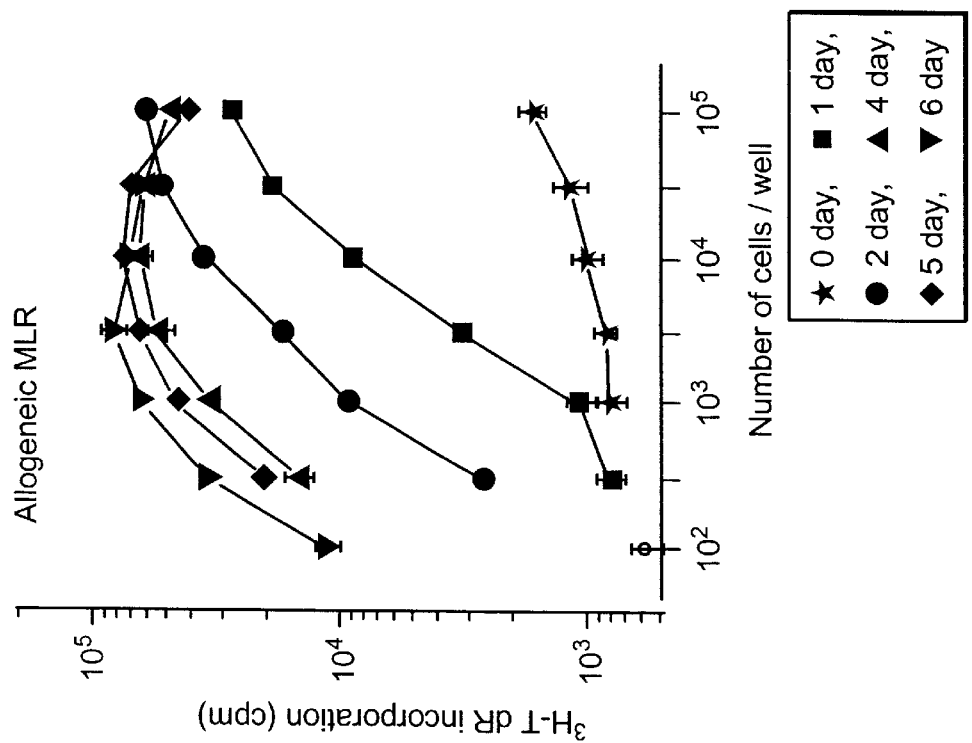

FIG. 5. (FIGS. 5A–5B) Progressive development of MLR stimulating activity in bone marrow cultured in the presence of GM-CSF.

Ia-negative precursors, B and T cell-depleted marrow cells were cultured in GM-CSF with ¾ of the medium being replaced every 2 d. At each time point, the cells were dislodged by gently pipetting. After irradiation, graded doses of marrow cells were applied to $3 \times 10^5$ allogeneic [C57BL/6, (5A, left)] or syngeneic [BALB/C×DBA/2 F1 (5B)] T cells and cultured for 4 days in the MLR. 3H-TdR uptake was measured at 80–94 h [values are means of triplicates with standard error bars].

Figure 6B:
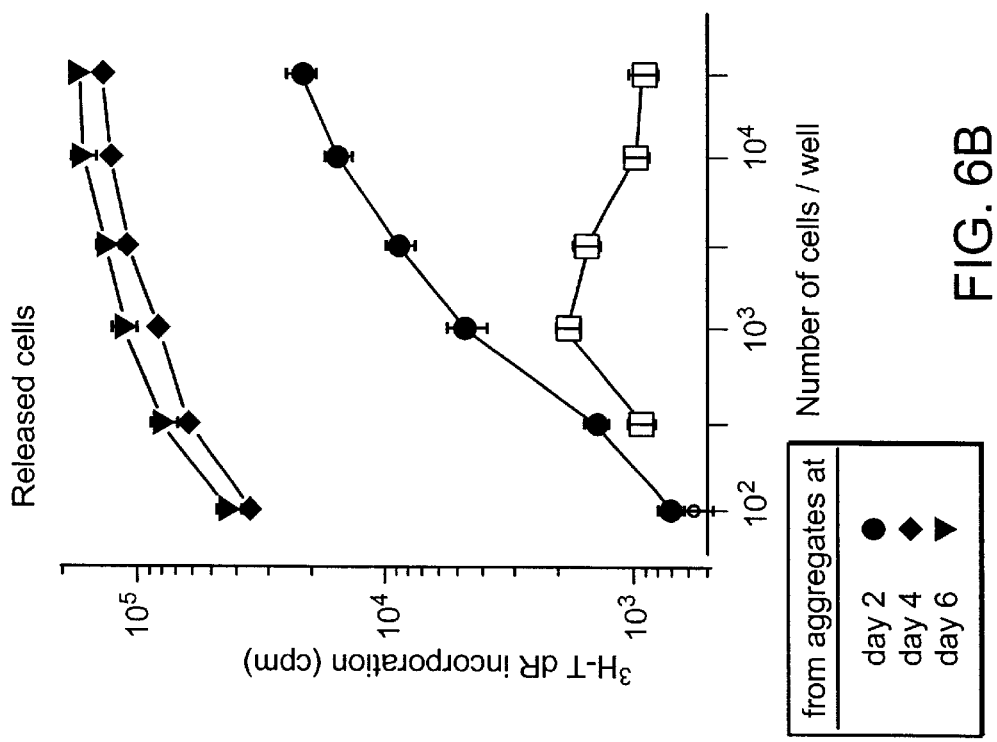
Figure 6A:
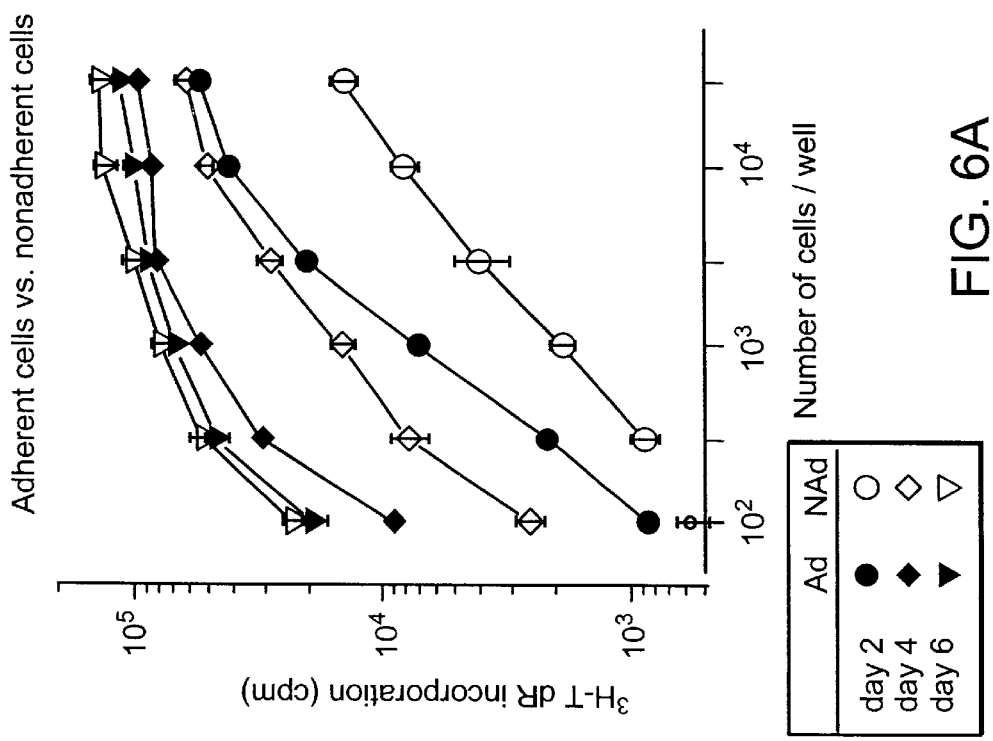
Figure 7A:
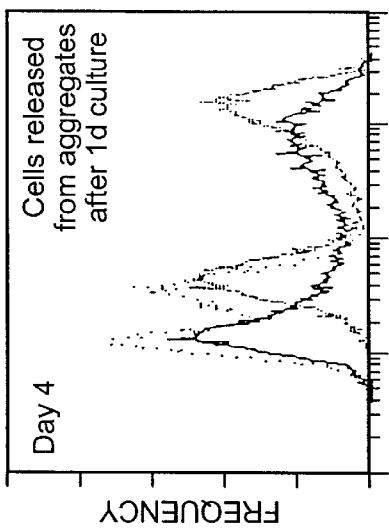
Figure 7B:
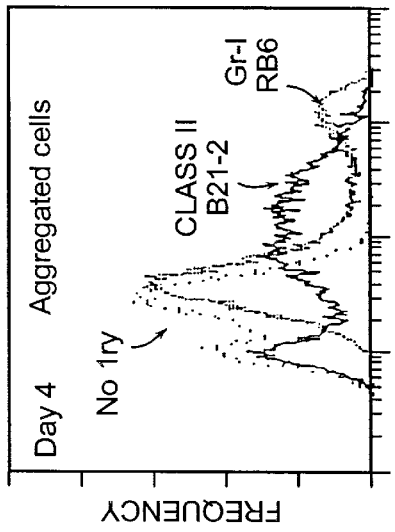
Figure 7C:
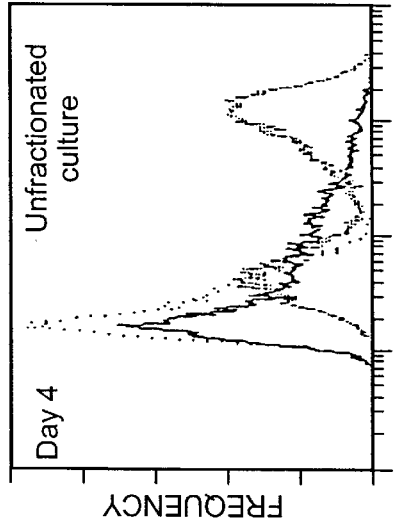
Figure 7D:
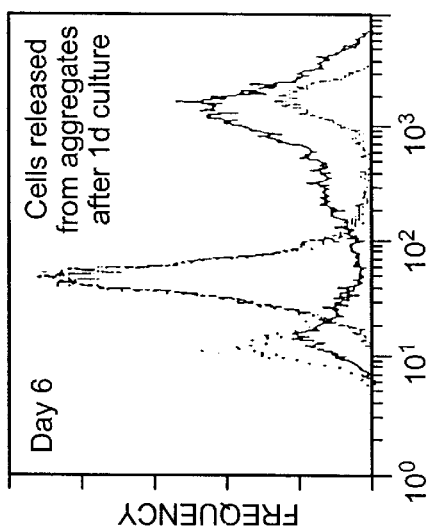
Figure 7E:
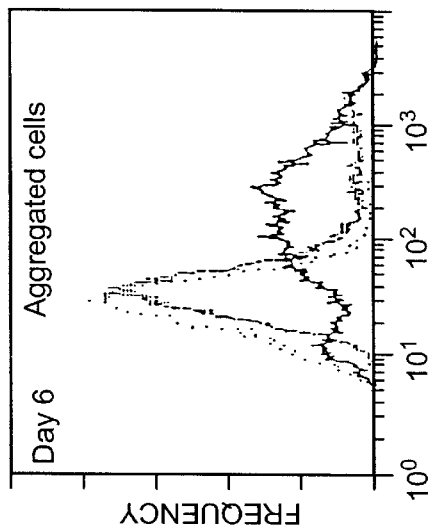
Figure 7F:
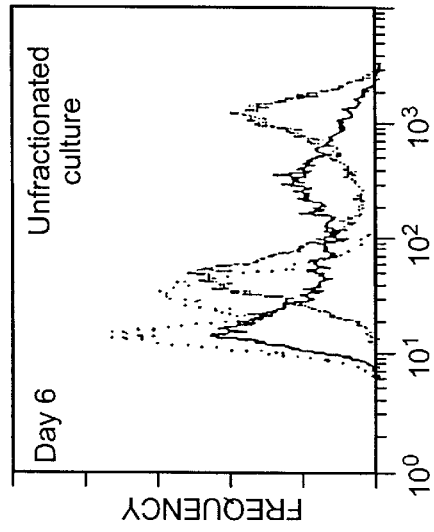
Figure 8A:
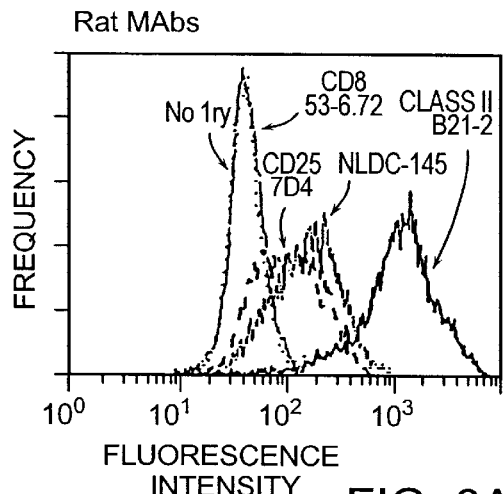
Figure 8B:
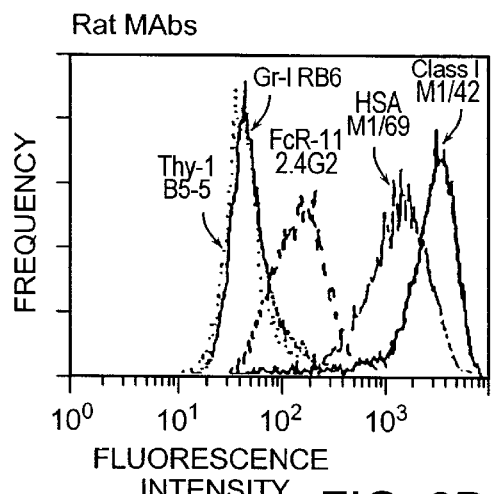
Figure 8C:
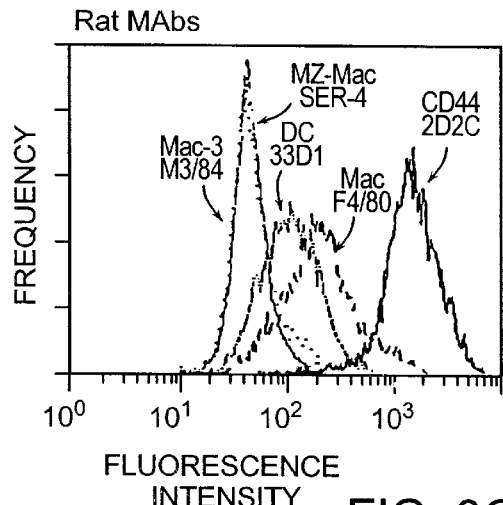
Figure 8D:
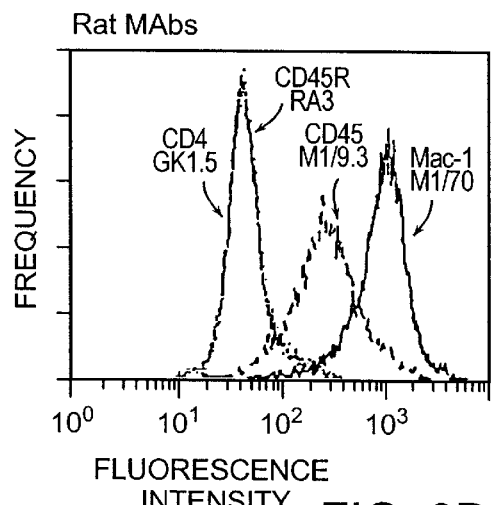
Figure 8E:
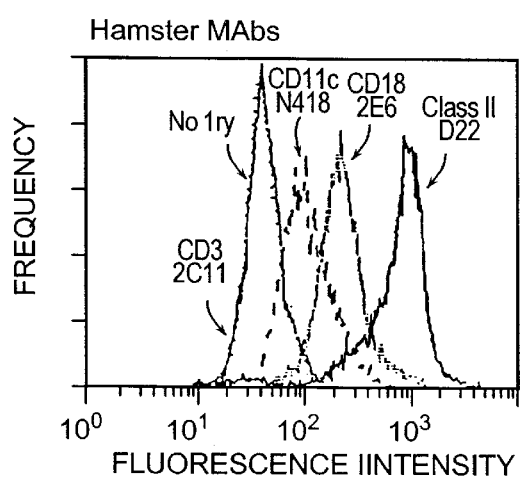

FIG. 6. (FIGS. 6A–6B) Physical properties of the MLR stimulating cells that develop in GM-CSF supplemented bone marrow cultures [see text].

6A. Cultures similar to those in FIG. 5 were separated into nonadherent [open symbols] and loosely adherent fractions [closed symbols], the latter being cells that could be dislodged by gently pipetting over the monolayer. For the d4 separations, loosely adherent cells [mainly granulocytes] were rinsed away at d2, and for the d6 separation, granulocytes were rinsed away at d2 and d4. The cells were irradiated and applied in graded doses to allogeneic T cells as in. FIG. 5.

6B. At the indicated time points, free cells and cell aggregates were dislodged from the stromal monolayer and separated by 1 g sedimentation. The aggregates were cultured for 1 day to provide released cells. These cells were irradiated and tested as MLR stimulators, as were firmly adherent cells that were dislodged in the presence of 10 mM EDTA [open squares].

FIG. 7. (FIGS. 7A–7F) Cell cytofluorometry of the development of Ia-positive cells from aggregates within bone marrow cultures supplemented with GM-CSF.

GM-CSF stimulated, bone marrow cultures [left (7A, 7D), unfractionated] were compared with loosely attached cell aggregates [middle (7B, 7E)] and cells released from the aggregates after overnight culture [right (7C, 7F)]. The cells were taken at day 4 (7A, 7B, 7C) or day 6 (7D, 7E, 7F), so that the released cells were analyzed at day 5 and day 7. The cells were stained with no primary mAb [no 1ry], or with mAb to granulocytes [RB-6] or MHC class II products [B21-2] followed by FITC-mouse anti-rat Ig.

FIG. 8. FIGS. 8A through 8E are detailed cell cytofluorometric phenotype analyses of the Ia-positive cells released from the growing dendritic cell aggregates. Contaminating, Ia-negative granulocytes were gated out on the basis of lower forward light scatter, so that one could examine the expression of many surface antigens on the larger cells using rat (FIGS. 8A through 8D) and hamster anti-mouse mAbs (7,17) (FIG. 8E) as indicated.

Figure 9:
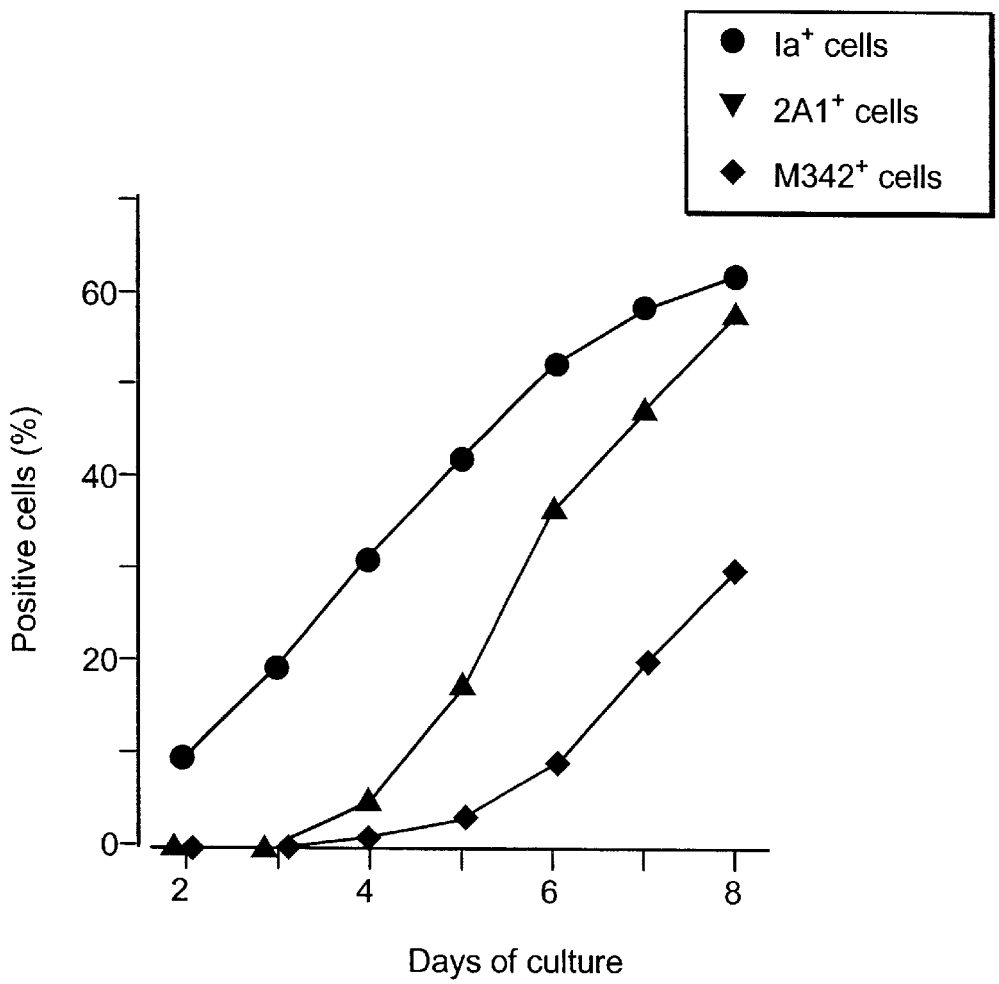

FIG. 9. Quantitation of developing cells that bear the dendritic cell restricted granule antigens 2A1 and M342.

Dendritic cells contain intracellular granules that react with the mAb such as M342 and 2A1 (34) mAbs. Ia-negative nonlymphocytes from mouse marrow were cultured in GM-CSF, and the loosely adherent granulocytes rinsed away at d2 and d4. The data on day 2 and 4 represent cells that could be dislodged by pipetting, while the data on d3 and d5–8 were cells released from the monolayer. At each of the indicated time points, at least 500 cells were counted in cytospins prepared and stained. [See text]. When cultures are started at $5 \times 10^5$ cells/cm$^2$ and fed with ¾ volume fresh medium every 2 days, the yields of total and Ia$^+$ cells were at d2, $1.05 \times 10^6$ and $2.1 \times 10^4$, at d4 $1.81 \times 10^6$ and $2.12 \times 10^5$, and at d6, $1.54 \times 10^6$ and $3.21 \times 10^5$.

Figure 10:
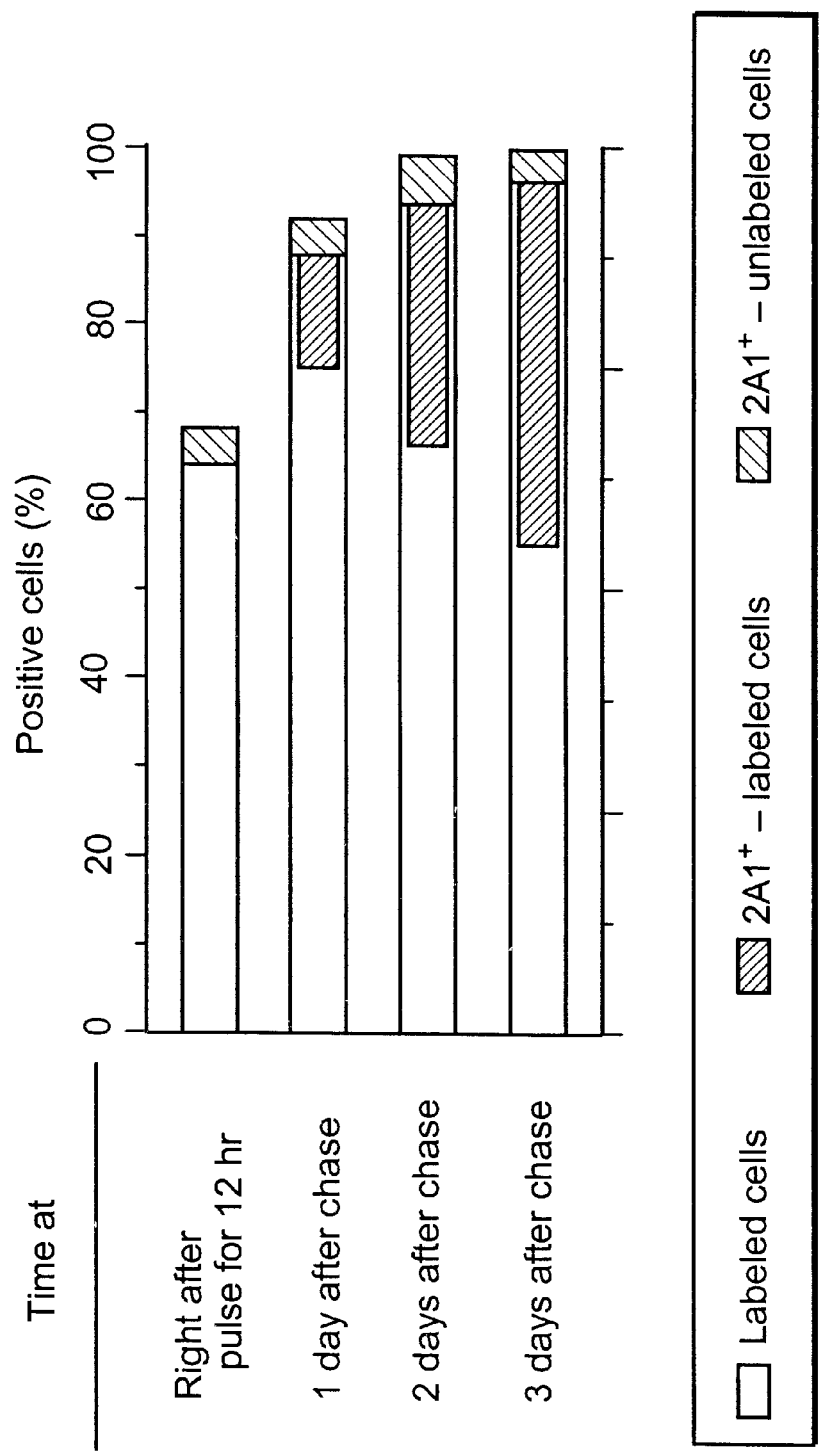

FIG. 10. Progenitor-progeny relationships in growing dendritic cells. Growing aggregates were separated at d4 from bone marrow cultures and pulsed with $^3$H-TDR at 0.1 $\mu$Ci/ml, $3 \times 10^5$ cells/well, for 12 h. All wells were replaced with fresh medium and returned to culture for 1, 2, or 3 days of chase. The yields of released cells during the chase were 2.0, 2.9, and $3.0 \times 10^5$ respectively per well. The content of Ia$^+$ cells was 28% after the pulse, and 47%, 55%, and 62% on days 1, 2, and 3 respectively. The data are shown as percentage of cells that were radiolabeled, with the filled in bars being cells that express the 2A1 granule cell antigen of mature dendritic cells.

Figure 11:
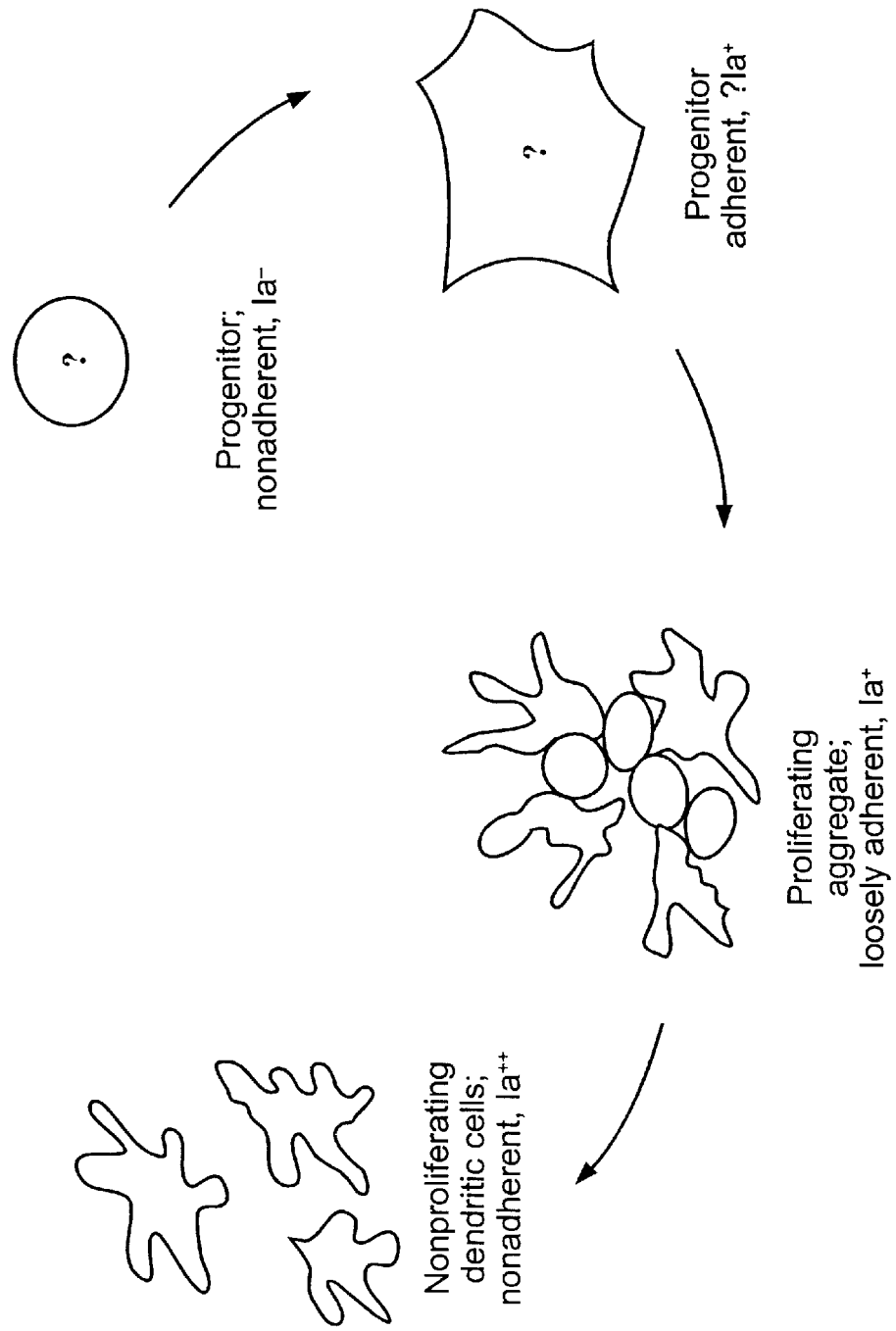

FIG. 11. Diagram of the proposed pathway of dendritic cell development in marrow cultures supplemented with GM-CSF. A proliferating aggregate forms from a precursor that either attaches to the cell stroma or is itself adherent. During dendritic cell differentiation, which is evident at the periphery of the aggregate and in cells released therefrom, there is a progressive increase in cell processes, MHC class II, NLDC-145 surface antigen, and M342 and 2A1 intracellular antigen [see text] and a progressive decrease in adherence to plastic.

Figures 12A, 12B, 12C, 12D:
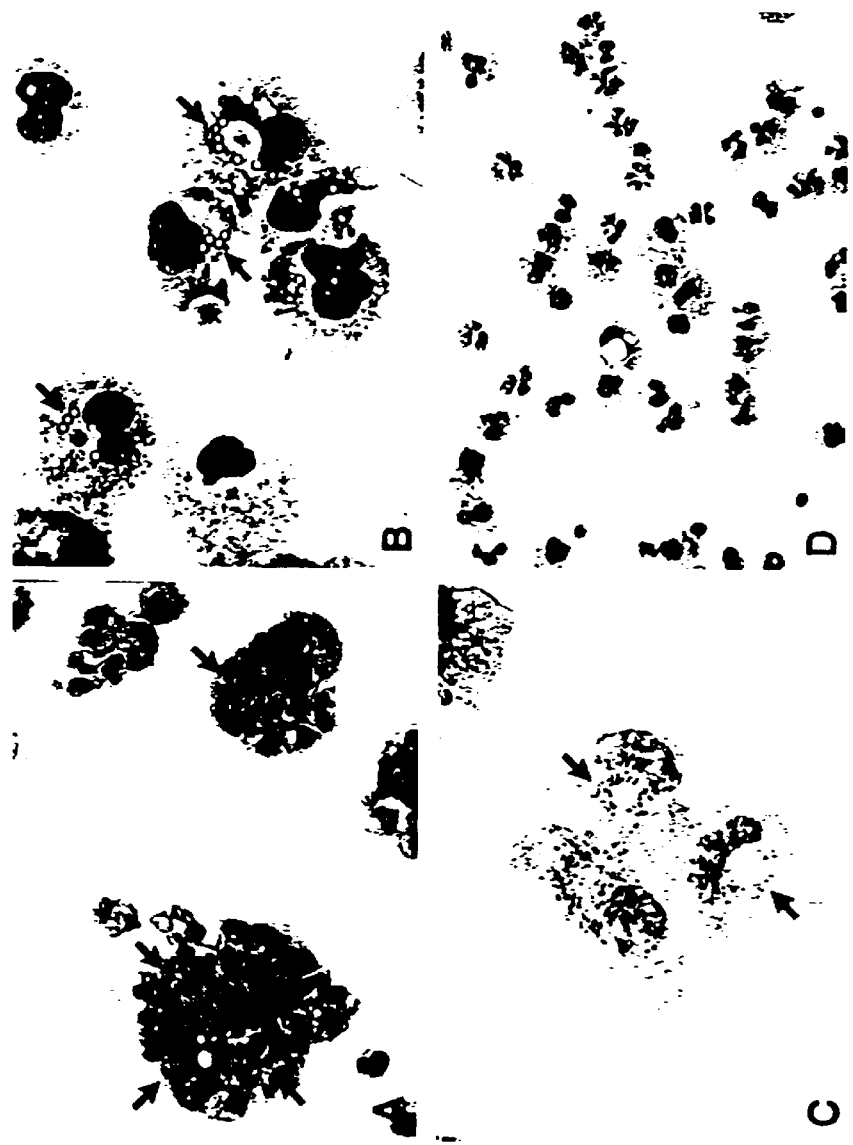

FIG. 12. (FIGS. 12A–12D) Diff-Quick stains of developing dendritic cells that have been exposed to latex and carbon.

12A. An aggregate of developing dendritic cells cytospun after a 20 h exposure to 2 u latex spheres. Many cells in the aggregate are labeled with the uniform latex particles [arrows].

12B. Same as A, but the cultures were chased for a day to allow the production of mature single dendritic cells. Many of the released dendritic cells contain the uniform and lucent latex spheres arranged around a clear cut centrosphere [arrows].

12C. Same as A and B, but the aggregates were pulsed with colloidal carbon and then chased for a day in carbon-free medium. The centrosphere of some of the mature dendritic cells that release from the aggregate contain small but clear cut endocytic granules of black, indigestible phagocytic tracer [arrows].

12D. Mature dendritic cells were exposed to carbon after they had been produced from proliferating aggregates. Carbon deposits are not evident.

FIG. 13. (FIGS. 13A–13D) Uptake of BCG into developing dendritic cells using two-color labels for acid fast bacilli and dendritic cell antigens. Clusters of developing dendritic cells [6 d marrow cultures induced with GM-CSF] were exposed for 20 h to BCG. The monolayers were washed and chased in medium with GM-CSF for 2 d. The cells were dissociated, labeled with FITC-anti-I-A mAb, and the class II-rich cells were isolated by cell sorting [most of the cells in the culture are class II-rich as shown previously (16)]. The sorted cells were cytospun, stained with auramine-rhodamine to visualize the cell-associated BCG, and double labeled with a different mAb and immunoperoxidase. The left and right panels of each pair are phase contrast (FIGS. 13A and 13C) and acid fast (FIGS. 13B and 13D) views respectively. Arrows on the left indicate the location of the bacilli on the right. The label for class II, [I-A and I-E, M5/114] outlines the cell processes better than the dendritic cell-restricted NLDC-145 antibody.

FIG. 14. (FIGS. 14A–14D) Electron microscopy of BCG in dendritic cells.

As in FIG. 2, BCG was added to GM-CSF stimulated d6 bone marrow cultures for a day. After washing and 2 more days of culture, the released cells were processed for electron microscopy.

14A (×5,400), 14B (×3,100). Low power views to show the typical dendritic cells with numerous processes and a few phagocytosed BCG [arrows].

14C (×20,000),14D (×15,000). Higher power views to show phagosomal membranes against the BCG, as well as organelles of the dendritic cell centrosphere including endocytic vacuoles [E], Golgi apparatus [GA], and small vesicles with a dense core [*].

FIG. 15. Antigen presentation to CFA primed (FIG. 15A)/ IFA (FIG. 15B) primed T cells.

T cells were purified from lymph nodes that drain paws that had been primed with complete [CFA] or incomplete [IFA]Freunds adjuvant. The different APCs are listed. Mature dendritic cells are d8 bone marrow cultures, and immature dendritic cells are from d5–6 cultures.

Figure 16:
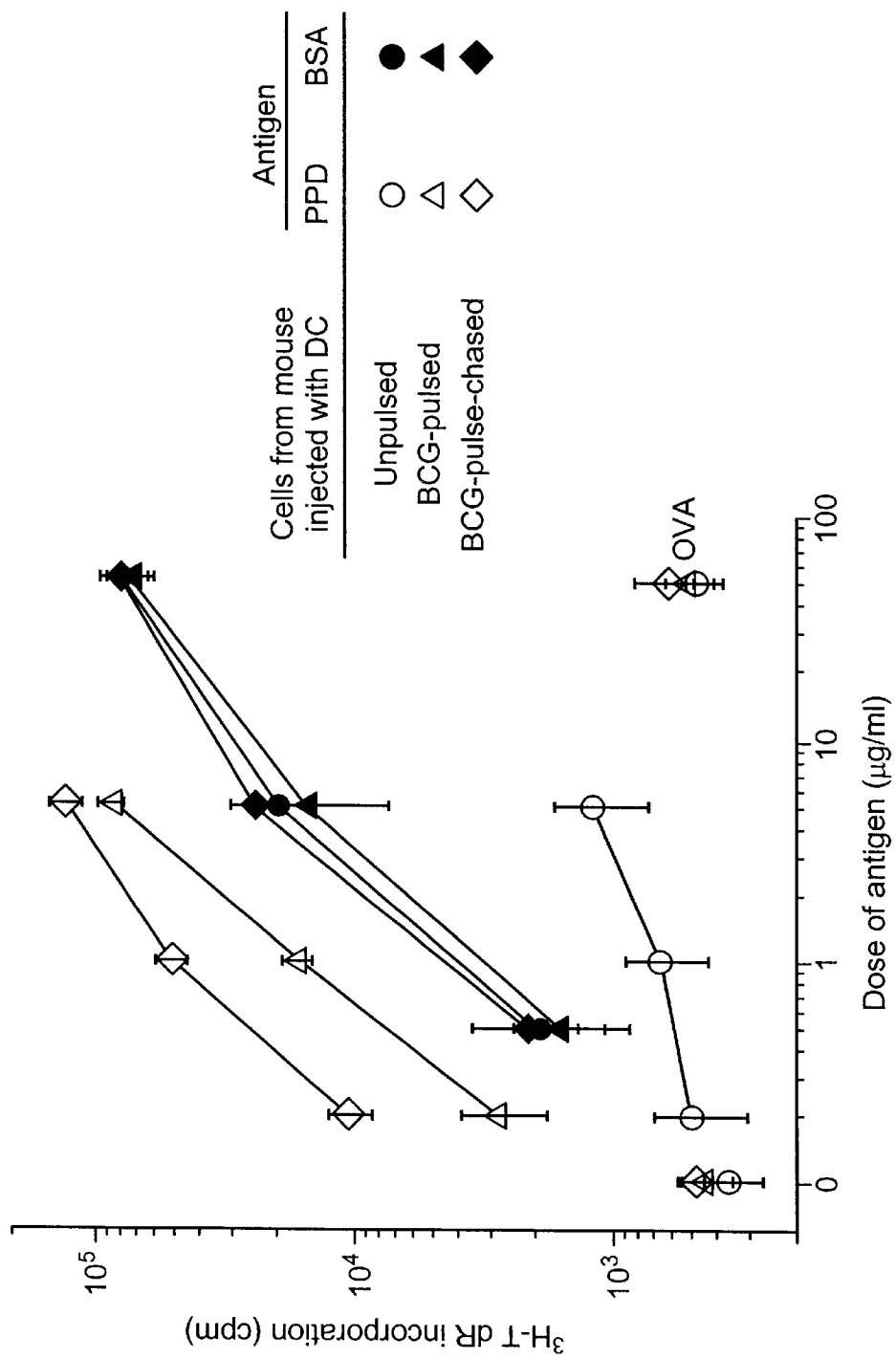

FIG. 16. Antigen presentation to naive lymph node T cells in situ.

Growing cultures of bone marrow dendritic cells were pulsed with BCG at d5–6, and used immediately or after a 2 d chase culture to activate T cells. The populations were injected into the paws of naive mice without artificial adjuvants. Five days later the draining lymph nodes were taken and stimulated in vitro with graded doses of PPD or BSA (the dendritic cells had been grown with fetal calf serum), the BSA to serve as a nonparticulate antigen. Data are means and standard errors for groups of 5 mice, each studied separately. Control lymph nodes not exposed to BCG pulsed dendritic cells did not respond to PPD or to BSA (<2000 cpm).

FIG. 17. (FIGS. 17A–17C) Antigen presentation to naive spleen cells in situ.

Growing cultures of bone marrow dendritic cells were pulsed with BCG at d5–6 (immature), at d7–8 (mature), or at d5–6 followed by a 2 d chase. $10^6$ cells of each group were injected i.v. into groups of mice. 5 or 10 days later, the spleen cells were cultured in vitro with graded doses of PPD (17A and 17C) or BSA (17B) as antigen. Since the dendritic cells were cultured in FCS, the use of BSA serves as control to ensure that all dendritic cell populations were comparably immunogenic in vivo. Unprimed spleen did not respond to either BSA or PPD.

Figure 18A:
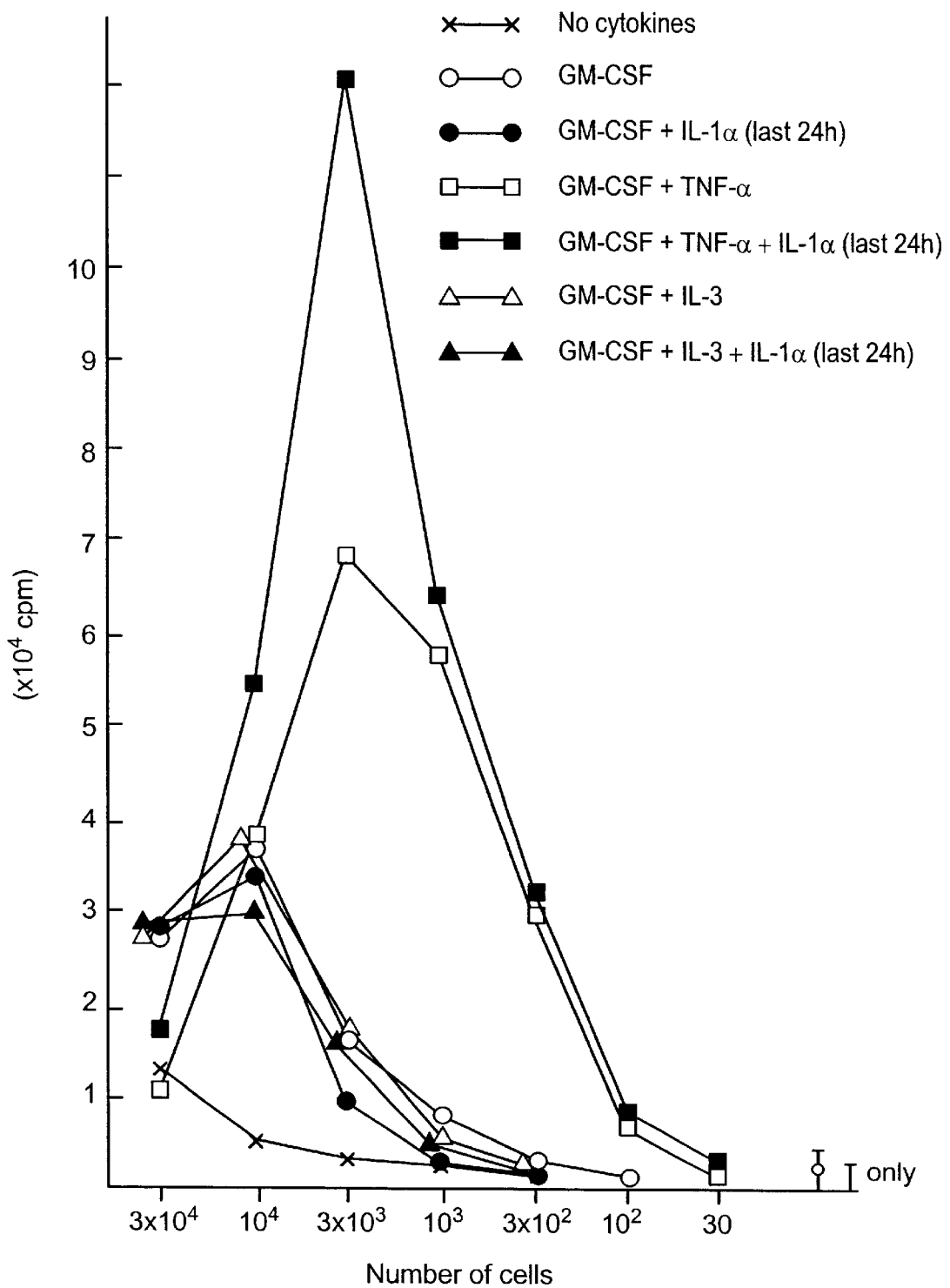
Figure 18B:
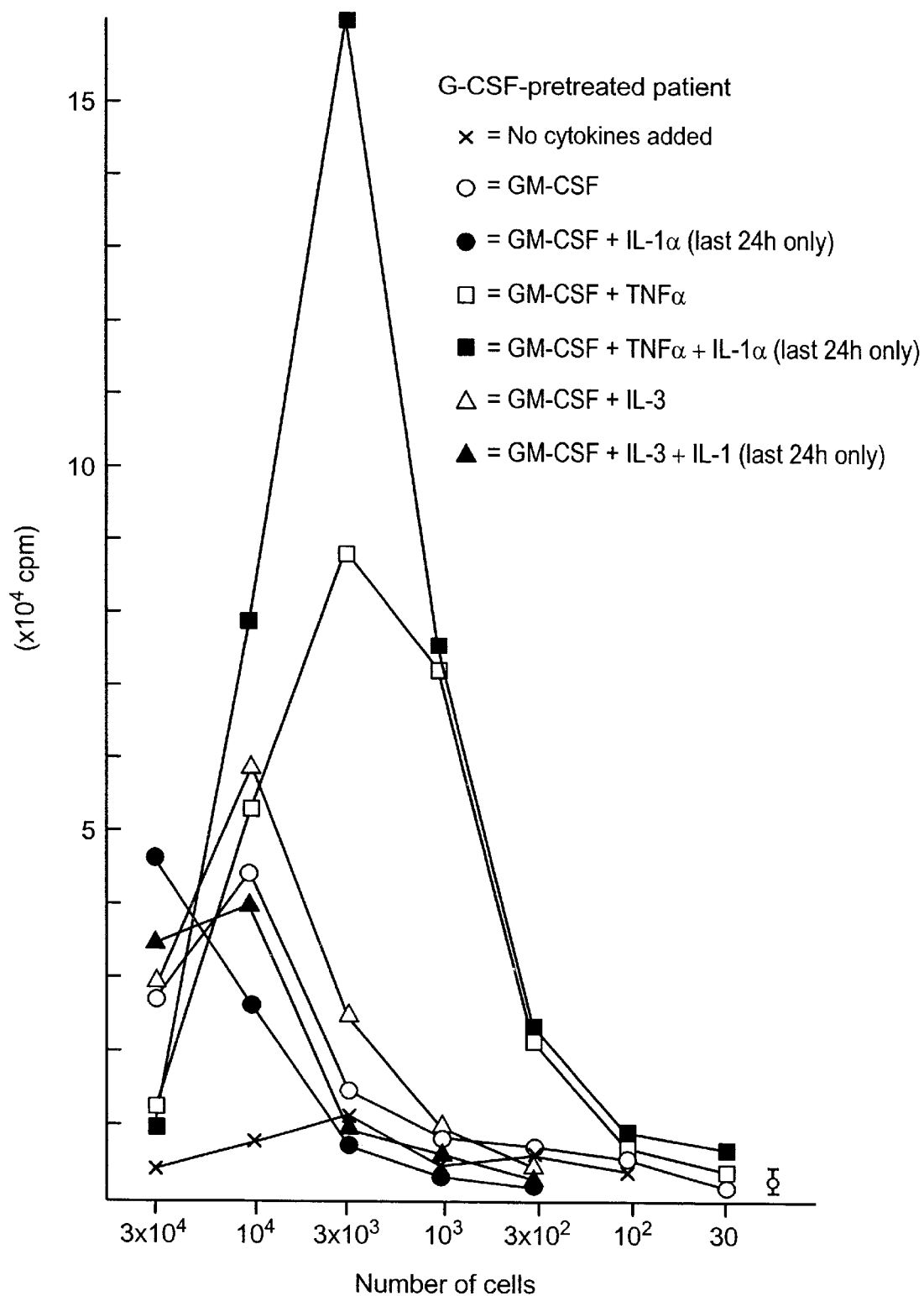
Figure 18C:
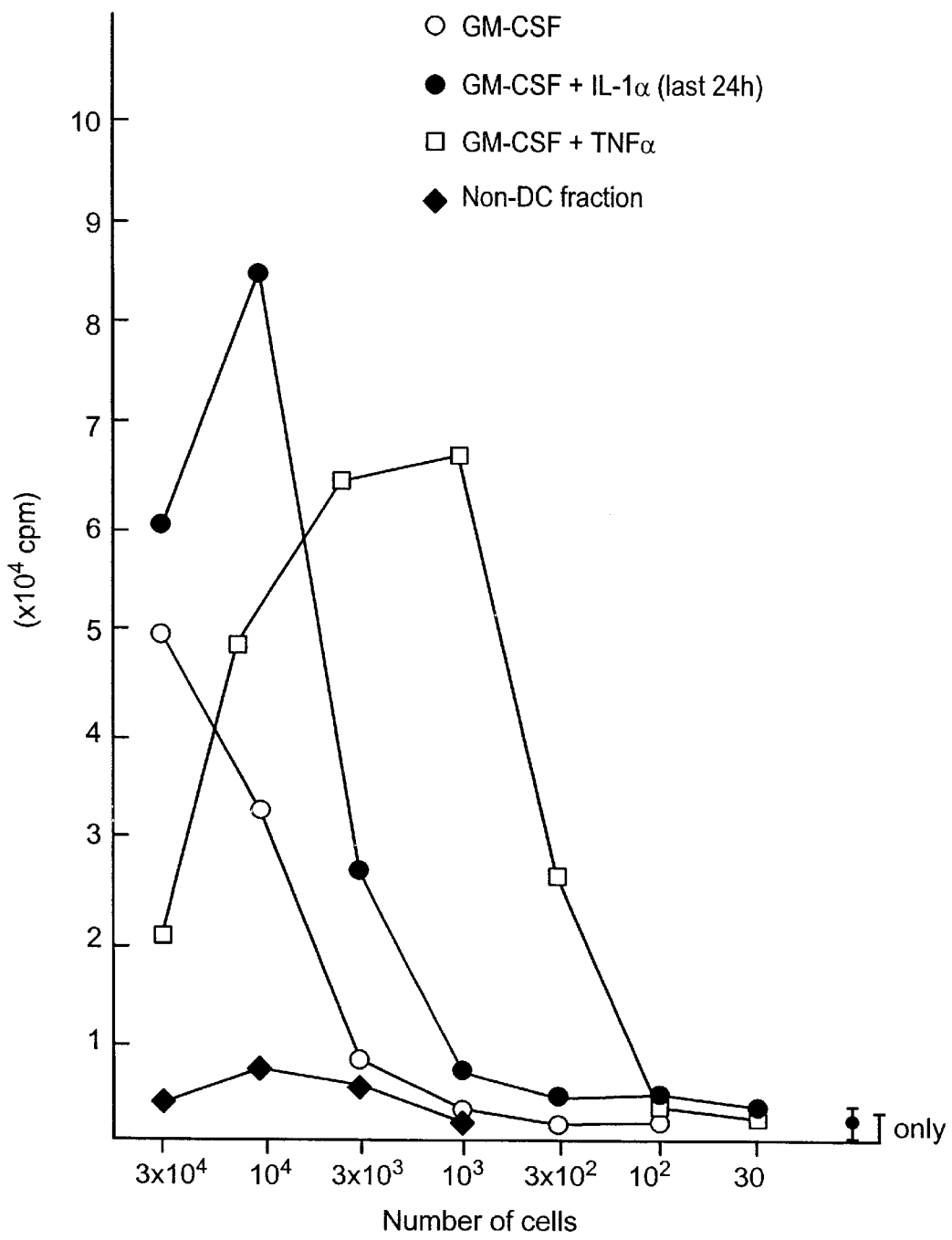
Figure 19C:
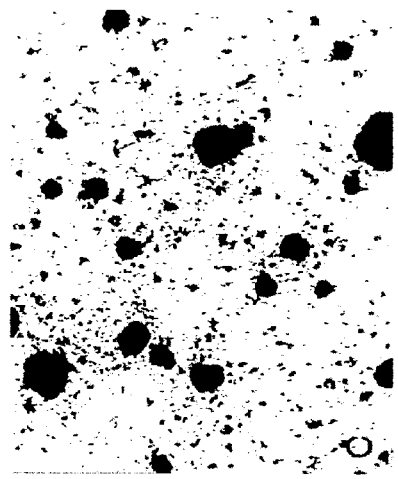
Figure 19B:
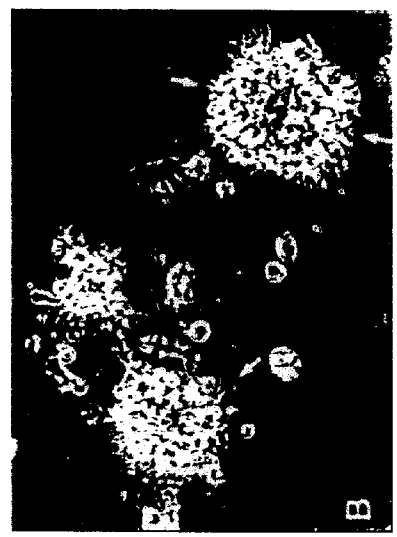
Figure 19A:
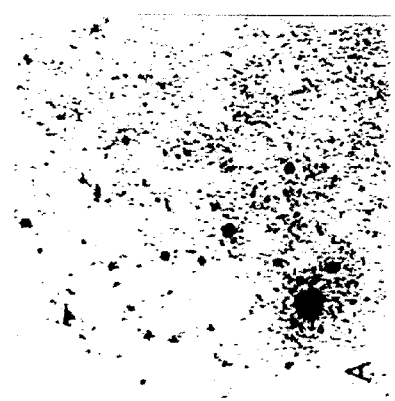
Figure 19E:
Figure 19D:

FIGS. 18A, 18B and 18C. Mixed Leukocyte Reaction (MLR) assay of human dendritic cells produced according to the method described in Example 6. Graded doses of irradiated cells (30 to 30,000 in serial 3 fold dilutions) were added to $2 \times 10^5$ accessory cell-depleted T cells. The T cell response of cells that had been cultured the absence of added cytokine (X); and in the presence of GM-CSF (O); GM-CSF+IL-1α (●); GM-CSF+TNF-α (□); GM-CSF+ TNF-α+IL-1α (■); GM-CSF+IL-3 (Δ); and GM-CSF+IL-3+IL-1 (▼) was measured with a 16 h pulse of $^3$H-thymidine on the 5th day. The response of non-dendritic cells is also shown in C, (♦). Three different experiments, shown in FIGS. 18A, 18B, and 18C are presented. Patients providing cells for experiments A & B were pretreated with G-CSF; patient in experiment C was pretreated with GM-CSF. Cytokines were used at the following concentrations: rhu GM-CSF, 400 or 800 U/ml; rhu IL-1α, 50 LAF units/ml (IL-1α was present in cultures only during the last 24 hours prior to harvesting the cells); rhu TNF-α 50 U/ml; and rhu IL-3 100 U/ml. The values on the X axis represent the number of dendritic cells except for X where dendritic cells were absent and the number is equivalent to total cell number. Standard deviations of triplicate cultures were<10% of the mean, and are not shown.

FIG. 19. FIG. 19 comprises FIGS. 19A through 19E which shows development of DCs in liquid cultures of cord blood mononuclear cells supplemented with GM-CSF and TNF. After 6 d small adherent aggregates are visible under the inverted phase contrast microscope (19A). Higher magnification reveals that they display typical veils at their edges (white arrows), and are affixed to adherent spindle-shaped cells (19B). At d14 the DC aggregates have become much larger (19C), and then finally release typical single DCs which display many processes (19D, bright field), notably characteristic veils (arrow indicates one such veil that appears en face) (19E, phase contrast). 19A, 19C, ×25; 19B, ×100; 19D, 19E, ×350.

FIG. 20. FIG. 20 comprises FIGS. 20A through 20F and shows T cell stimulatory function (1° allogeneic MLR) of dendritic cells (DC) grown from cord blood with GM-CSF+ TNF α (20A), DC grown with GM-CSF+TNF from blood of cancer patients after high-dose chemotherapy and G-CSF treatment (20B), and DC grown from normal peripheral blood with GM-CSF+TNF α (20C) or with GM-CSF+IL-4 (20D, 20E, 20F). Responder cells were purified T lymphocytes ($2 \times 10^5$ in 96 flat bottom wells). Equal numbers of irradiated (3000 rad, $^{137}$Cs) blood DC (closed circles in all panels) as identified by FACS analyses (CD1a$^+$/HLA-DR$^+$ cells, compare FIG. 23) were compared both to cultured epidermal Langerhans cells [LC] from the same donor in 20D and to poorly stimulating cell populations (whole PBMC in 20D, and 20E; adherent macrophages from the same cultures in 20C; control cultures grown in the absence of cytokines in 20F [open triangles]).

Note that DC are 10–50-fold stronger than PBMC (20D, 20E) or macrophages (20C) and that they are comparable to DC from skin (20D). In addition, 20B and 20E show the enhancing effect of IL-1 (added during the last 24 h of culture) on the T cell stimulatory capacity of DC. Without cytokines no immunostimulatory DC develop in the cultures (20F).

Figure 21C:
Figure 21B:
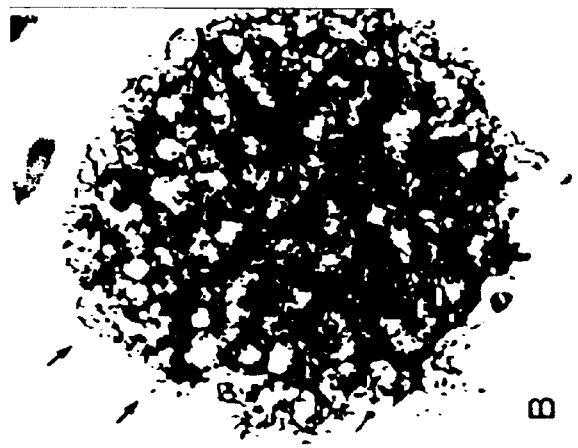
Figure 21A:
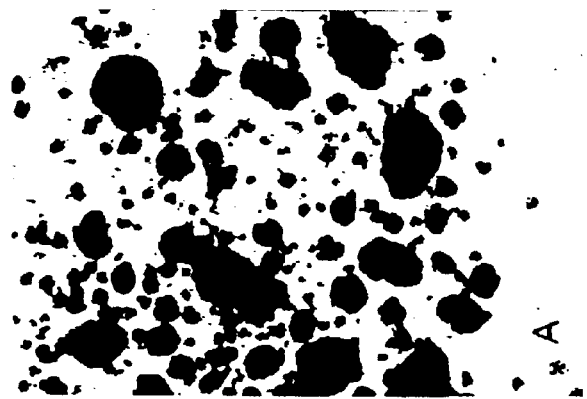

FIG. 21. FIG. 21 comprises FIGS. 21A through 21C which shows development of DCs in liquid cultures of normal, adult blood mononuclear cells supplemented with GM-CSF+IL-4. On d2.5 small adherent DC aggregates are readily visible under the inverted phase contrast microscope (21A). On d7 the DC aggregates have become nonadherent, very large, and loose (21B). The nonadherent fraction of the cultures was harvested and vigorously resuspended to obtain single DCs in large numbers (21C, arrows mark some veils). 21A, 21B, ×25; 21C, ×500.

FIG. 22. FIG. 22 comprises FIGS. 22A through 22H and shows phenotype and proliferation characteristics of DCs grown from normal blood with GM-CSF+IL-4. Fluorescence pictures in each row represent identical microscopic fields of double-labeled cytospin preparations. FIGS. 22A through 22D are stained with anti-HLA-DR. DC grown in GM-CSF and IL-4 are strongly HLA-DR positive (22A) but display only a dull spot of anti-CD68 reactivity (22E). In contrast, control cells grown in parallel without cytokines (mainly macrophages) show an inverted pattern: very low HLA-DR (22B) but brilliant CD68 expression (22F). MAb Lag (22C) identifies occasional Birbeck granule containing cells in the center of an HLA-DR-expressing aggregate of DC (22G). Peroxidase staining of nuclei and nucleoli with mAb Ki-67 (22D and 22H) demonstrates that proliferation occurs predominantly in aggregates (22H); singly dispersed DC derived from firmly adherent cells (see text) are not stained (22D). 22A–C and 22E–G, 200×; 22D and 22H, 100×.

FIG. 23 Cytofluorographic analysis of dendritic cells (DC) grown from normal peripheral blood with GM-CSF+ IL-4. Two different representative experiments are shown. Epidermal Langerhans cells (LC) cultured for 3d were included in one experiment for comparison. Three color immunolabeling was performed. Cells were stained with different mouse mAb's followed in sequence by biotinylated anti-mouse Ig, streptavidin-phycoerythrin, mouse Ig for blocking free binding sites, and FITC-conjugated anti-HLA-DR. Dead cells and lymphocytes were excluded from analysis by propidium iodide staining and light scatter properties, respectively. More than 90% of the remaining cells were strongly MHC-class II positive and constituted DC. The phenotype of this population is shown here (shaded curves). Isotype-matched control antibodies are included in each histogram (bold curves). Blood DC display a phenotype typical for DC as described and almost identical to cultured LC in direct comparison (Lenz, et al. (1993). *J. Clin. Invest.*, 92:2587; Freudenthal, P. S. and R. M. Steinman. (1990) *Proc. Natl. Acad. Sci. USA.*, 87:7698; Romani, et al. (1989) *J. Invest. Dermatol.*, 93:600; O'Doherty, et al. (1993) *J. Exp. Med.*, 178:1067. Notably, they do not express CD14 but have high levels of MHC molecules (HLA-ABC, DR, DQ, DP), adhesions (CD54, CD58, CD11a*, CD11c), and costimulatory molecules (CD40, B7/CD80). They are also negative with markers for granulocytes (CD15), NK cells (CD16), B cells (CD19*, CD20), and T cells (CD3, CD8*). Expression of CD5 and the staining pattern of CD45RA and –RO are as described for DC isolated from fresh blood O'Doherty, et al. (1993) *J. Exp. Med.*, 178:1067 (34).
* not shown here.

Figure 24:

FIG. 24. Ultrastructure of DCs grown from normal, adult blood mononuclear cells with GM-CSF+IL-4. Low power view (×4,700) shows three profiles of DCs. Arrowheads indicate veils, i.e. thin cytoplasmic processes devoid of organelles. Area marked by bracket is shown at higher magnification (×33,000) to demonstrate the characteristic abundance of mitochondria and paucity of lysosomes/phagosomes.

DETAILED DESCRIPTION OF THE INVENTION

This invention relates to a method of producing cultures of proliferating dendritic cell precursors which mature in vitro to mature dendritic cells. The dendritic cells and the dendritic cell precursors produced according to the method of the invention may be produced in amounts suitable for various immunological interventions for the prevention and treatment of disease.

The starting material for the method of producing dendritic cell precursors and mature dendritic cells is a tissue source comprising dendritic cell precursors which precursor cells are capable of proliferating and maturing in vitro into dendritic cells when treated according to the method of the invention. Such precursor cells are nonadherent and typically do not label with mAb markers found on mature dendritic cells such as Ia antigens, 2A1 and M342 antigens (34, 44) and the NLDC145 interdigitating cell source antigen (13). Preferably such tissue sources are spleen, afferent lymph, bone marrow and blood. More preferred tissue sources are bone marrow and blood. Blood is also a preferred tissue source of precursor cells because it is easily accessible and could be obtained in relatively large quantities.

To increase the number of dendritic precursor cells in animals, including humans it is preferable to treat such individuals with substances which stimulate hematopoiesis. Such substances include G-CSF, GM-CSF and may include other factors which promote hematopoiesis. The amount of hematopoietic factor to be administered may be determined by one skilled in the art by monitoring the cell differential of individuals to whom the factor is being administered. Typically, dosages of factors such as G-CSF and GM-CSF will be similar to the dosage used to treat individuals recovering from treatment with cytotoxic agents. Preferably, GM-CSF or G-CSF is administered for 4 to 7 days at standard doses prior to removal of source tissue to increase the proportion of dendritic cell precursors. (Editorial, Lancet, 339: Mar. 14, 1992, 648–649). For example, we have determined that dosages of G-CSF of 300 micrograms daily for 5 to 13 days and dosages of GM-CSF of 400 micrograms daily for 4 to 19 days have resulted in significant yields of dendritic cells.

Fetal or umbilical cord blood, which is also rich in growth factors is also a preferred source of blood for obtaining precursor dendritic cells.

According to a method of the invention, the tissue source may be treated prior to culturing culturing to enrich the proportion of dendritic precursor cells relative to other cell types. Such pretreatment may also remove cells which may compete with the proliferation of dendritic precursor cells or inhibit their proliferation or survival. Pretreatment may also be used to make the tissue source more suitable for in vitro culture. The method of treatment will likely be tissue specific depending on the particular tissue source. For example, spleen or bone marrow if used as a tissue source would first be treated so as to obtain single cells followed by suitable cell separation techniques to separate leukocytes from other cell types. Treatment of blood would involve cell separation techniques to separate leukocytes from other cells types including red blood cells (RBCs) which are toxic. Removal of RBCs may be accomplished by standard methods known to those skilled in the art. In addition, antitoxins such as anti-erythroid monoclonal VIE-64 antibody which bind RBCs may be used to facilitate binding of RBC to a substrate for removal using a panning technique.

According to a preferred method of this invention, when bone marrow is used as the tissue source, B cells are removed prior to culturing of bone marrow in GM-CSF. While B cells and pre-B cells do not grow in response to GM-CSF, they represent approximately 50% of the initial marrow suspension and thereby preclude the use of staining with anti-Ia monoclonal antibodies to quickly enumerate dendritic cells. Additionally, granulocytes are GM-CSF responsive and readily proliferate in the presence of GM-CSF. As such, the B cells and granulocytes mask the presence of dendritic cell precursors. B cells can express the M342 and 2A1 granular antigens that are useful markers for distinguishing dendritic cells from macrophages and granulocytes. Moreover, granulocytes have a tendency to overgrow the cultures and compete for available GM-CSF. The most preferred method under this invention is to remove the majority of nonadherent, newly-formed granulocytes from the bone marrow cultures by gentle washes during the first 2–4 days in culture.

Preferably, in one form of pretreatment cells which compete and mask the proliferation of precursor dendritic cells are killed. Such pretreatment comprises killing cells expressing antigens which are not expressed on dendritic precursor cells by contacting bone marrow with antibodies specific for antigens not present on dendritic precursor cells in a medium comprising complement. Another form of pretreatment to remove undesirable cells suitable for use with this invention is adsorbing the undesirable precursor cells or their precursors onto a solid support using antibodies specific for antigens expressed on the undesirable cells. Several methods of adsorbing cells to solid supports of various types are known to those skilled in the art and are suitable for use with this invention. For example, undesirable cells may be removed by "panning" using a plastic surface such as a petri dish. Alternatively, other methods which are among those suitable include adsorbing cells onto magnetic heads to be separated by a magnetic force; or immunobeads to be separated by gravity. Non adsorbed cells containing an increased proportion of dendritic cell precursors may then be separated from the cells adsorbed to the solid support by known means including panning. These pretreatment step serves a dual purpose: they destroy or revives the precursors of non-dendritic cells in the culture while increasing the proportion of dendritic cell precursors competing for GM-CSF in the culture.

In addition, Ia-positive cells, i.e. B cells and macrophages preferably are killed by culturing the cells in the presence of a mixture of anti Ia-antibodies, preferably monoclonal antibodies, and complement. Mature dendritic cells which are also present in bone marrow are also killed when the cells from the bone marrow are cultured in the presence of anti Ia-antibodies, however, these mature dendritic cells occur in such low quantities in the blood and bone marrow and possess such distinct antigenic markers from dendritic cell precursors that killing of these mature dendritic cells will not significantly effect the proliferation and yield of dendritic cell precursors. T and B cells as well as monocytes which also may be present in the bone marrow may be killed by including antibodies directed against T and B cell antigens and monocytes. Such antigens include but are not limited to CD3, CD4, the B cell antigen B220, thy-1, CD8 and monocyte antigens. The remaining viable cells from the bone marrow are then cultured in medium supplemented-with about 500–1000 U/ml GM-CSF and cultured as described below. It should be noted that CD4 and CD8 antigens may be present on young dendritic cell precursors, therefore, antibodies directed to these antigens may deplete the dendritic cell precursor populations.

When blood is used as a tissue source, blood leukocytes may be obtained using conventional methods which maintain their viability. According to the preferred method of the invention, blood is diluted into medium (preferably RPMI) containing heparin (about 100 U/ml) or other suitable anticoagulant. The volume of blood to medium is about 1 to 1. Cells are pelleted and washed by centrifugation of the blood in medium at about 1000 rpm (150 g) at 4° C. Platelets and red blood cells are depleted by suspending the cell pellet in a mixture of medium and ammonium chloride. Preferably the mixture of medium to ammonium chloride (final concentration 0.839 percent) is about 1:1 by volume. Cells are pelleted by centrifugation and washed about 2 more times in the medium-ammonium chloride mixture, or until a population of leukocytes, substantially free of platelets and red blood cells, is obtained.

Any isotonic solution commonly used in tissue culture may be used as the medium for separating blood leukocytes from platelets and red blood cells. Examples of such isotonic solutions are phosphate buffered saline, Hanks balanced salt solution, or complete growth mediums including for example RPMI 1640. RPMI 1640 is preferred.

Cells obtained from treatment of the tissue source are cultured to form a primary culture on an appropriate substrate in a culture medium supplemented with GM-CSF or a GM-CSF derivative protein or peptide having an amino acid sequence which sequence maintains biologic activity typical of GM-CSF. The appropriate substrate may be any tissue culture compatible surface to which cells may adhere. Preferably, the substrate is commercial plastic treated for use in tissue culture. Examples include various flasks, roller bottles, petri dishes and multi-well containing plates made for use in tissue culture. Surfaces treated with a substance, for example collagen or poly-L-lysine, or antibodies specific for a particular cell type to promote cell adhesion may also be used provided they allow for the differential attachment of cells as described below. Cells are preferably plated at an initial cell density of about $7.5 \times 10^5$ cells per $cm^2$. At this dose, the surface is not fully covered by cells, but there are no big spaces (2–3 cell diameters) either.

When bone marrow which has been treated to reduce the proportion of non-dendritic cell precursors is cultured, aggregates comprising proliferating dendritic cell precursors are formed. The Ia-negative marrow nonlymphocytes comprising dendritic cell precursors are preferably cultured in high numbers, about $10^6$/well ($5 \times 10^5$ cells/$cm^2$) Liquid marrow cultures which are set up for purposes other than culturing dendritic cell precursors are typically seeded at 1/10th this dose, but it is then difficult to identify and isolate the aggregates of developing dendritic cells.

The growth medium for the cells at each step of the method of the invention should allow for the survival and proliferation of the precursor dendritic cells. Any growth medium typically used to culture cells may be used according to the method of the invention provided the medium is supplemented with GM-CSF. Preferred medias include RPMI 1640, DMEM and α-MEM, with added amino acids and vitamins supplemented with an appropriate amount of serum or a defined set of hormones and an amount of GM-CSF sufficient to promote proliferation of dendritic precursor cells. Serum-free medium supplemented with hormones is also suitable for culturing the dendritic cell precursors. RPMI 1640 supplemented with 5% fetal calf serum (FCS) and GM-CSF is preferred. Cells may be selected or adapted to grow in other serums and at other concentrations of serum. Cells from human tissue may also be cultured in medium supplemented with human serum rather than FCS. Medias may contain antibiotics to minimize bacteria infection of the cultures. Penicillin, streptomycin or gentamicin or combinations containing them are preferred. The medium, or a portion of the medium, in which the cells are cultured should be periodically replenished to provide fresh nutrients including GM-CSF.

GM-CSF has surprisingly been found to promote the proliferation in vitro of precursor dendritic cells. Cells are cultured in the presence of GM-CSF at a concentration sufficient to promote the survival and proliferation of dendritic cell precursors. The dose depends on the amount of competition from other cells (especially macrophages and granulocytes) for the GM-CSF, or to the presence of GM-CSF inactivators in the cell population. Preferably, the cells are cultured in the presence of between about 1 and 1000 U/ml of GM-CSF. More preferably cells from blood are cultured in the presence of GM-CSF at a concentration of between about 30 and 100 U/ml. This dose has been found to be necessary and sufficient for maximal responses by cells obtained from mouse blood. Most preferably, cells are cultured in the presence of GM-CSF at a concentration of about 30 U/ml. GM-CSF at a concentration of between about 400–800 U/ml has been found to be optimal for culturing proliferating human dendritic cells from blood. Cells from bone marrow require higher concentrations of GM-CSF because of the presence of large numbers of proliferating granulocytes which compete for the available GM-CSF, therefore, doses between about 500–1000 U/ml are preferred for cultures of cells obtained from marrow.

When suspensions of mouse bone marrow are cultured in the presence of GM-CSF, three types of myeloid cells expand in numbers. (1) Neutrophils predominate but do not adhere to the culture surface. Neutrophils have a characteristic nuclear morphology, express the RB-6 antigen, and lack MHC class II products. (2) Macrophages are firmly adherent to the culture vessel, express substantial levels of the F4/80 antigen, and for the most part express little or no MHC class II [but see below].

When mouse or human blood leukocytes are cultured in GM-CSF at 30 U/ml or 400–800 U/ml, respectively, the cultures develop a large number of aggregates or cell balls from which typical dendritic cells are eventually released. In the absence of GM-CSF, no colonies develop. Cytologic criteria may be used to initially detect the dendritic cells which characteristically extend large, sheet-like processes or veils (25–27).

GM-CSF may be isolated from natural sources, produced using recombinant DNA techniques or prepared by chemical synthesis. As used herein, GM-CSF includes GM-CSF produced by any method and from any species. "GM-CSF" is defined herein as any bioactive analog, fragment or derivative of the naturally occurring (native) GM-CSF. Such fragments or derivative forms of GM-CSF should also promote the proliferation in culture of dendritic cell precursors. In addition GM-CSF peptides having biologic activity can be identified by their ability to bind GM-CSF receptors on appropriate cell types.

It may be desirable to include additional cytokines in the culture medium in addition to GM-CSF to further increase the yield of dendritic cells. Such cytokines include granulocyte colony-stimulating factor (G-CSF), monocyte-macrophage colony-stimulating factor (M-CSF), interleukins 1 α and 1 β, 3, 4, 6, and 13 (IL-1 α, IL-1β, IL-3, IL-4, IL-6, and IL-13 respectively), tumor necrosis factor α (TNFα), and stem cell factor (SCF). Cytokines are used in amounts which are effective in increasing the proportion of dendritic cells present in the culture either by enhancing proliferation or survival of dendritic cell precursors. Preferably, cytokines are present in the following concentrations: IL-1α and β, 1 to 100 LAF units/ml; TNF-α, 5–500 U/ml; IL-3, 25–500 U/ml; M-CSF, 100–1000 U/ml; G-CSF, 25–300 U/ml; SCF, 10–100 ng/ml; IL-4, 500–1000 U/ml and IL-6, 10–100 ng/ml. More preferred concentrations of cytokines are: IL-1α, 50 LAF units/ml; TNFα, 50 U/ml; IL-3, 100 U/ml; M-CSF, 300 U/ml; and G-CSF, 100 U/ml. Preferred cytokines are human proteins. Most preferred cytokines are produced from the human gene using recombinant techniques (rhu). (TNFα) at concentrations from about 10–50 U/ml may be used to increase dendritic cell yields several fold.

In certain tissue sources the presence of non-dendritic cell precursors or stem cells capable of maturing to non-dendritic cells may reduce the proportion of mature dendritic cells obtained. It may therefore be desirable to reduce the population of non-dendritic cells present in the culture by including factors which inhibit the proliferation or maturation of non-dendritic cell precursors. For example, if human blood isolated from healthy humans is the tissue source for dendritic precursors it is preferred that isolated peripheral blood mononuclear cells are cultured in GM-CSF and at least one additional agent. This agent should inhibit the proliferation and/or maturation of other cell types within the culture. It is preferable that such an agent inhibit macrophage proliferation and/or maturation without substantially inhibiting dendritic cell proliferation and/or maturation. Examples of such a macrophage inhibiting agent includes, but are not limited to, IL-4 and IL-13. A suggested range for IL-4 is 500–1000 U/ml. It is preferred that the IL-4 be present at the start or immediately thereafter of the culture. The IL-4 may be isolated from natural sources or recombinantly produced.

Without being bound by theory the TNF-α may facilitate the proliferation of dendritic progenitors present in human cord blood and human blood isolated from chemotherapeutic patients pretreated with GM-CSF but does not enhance proliferation of many dendritic precursors present in normal human blood.

GM-CSF, however is essential for the proliferation and maturation of dendritic cell precursors.

TNF-α appears to facilitate the proliferation of dendritic cell progenitors cultured in GM-CSF found in cord blood (Caux et al Nature (1992) 360:258–261; example 8 and blood isolated from chemotherapeutic patients pretreated with GM-CSF). However TNF-α does not appear to facilitate dendritic cell proliferation in many dendritic cell progenitors isolated from normal human blood and cultured in GM-CSF (see example 8).

TNF-α may, however negatively impact on antigen retention and presentation in non-proliferating dendritic cells. In another embodiment of this invention proliferating dendritic cell are cultured in the presence of GM-CSF and TNF-α at a time sufficient to allow increased proliferation of the dendritic cell progenitors without impairing the antigen presenting and retention abilities of the dendritic cell.

The primary cultures from the tissue source are allowed to incubate at about 37° C. under standard tissue culture conditions of humidity and pH until a population of cells has adhered to the substrate sufficiently to allow for the separation of nonadherent cells. The dendritic cell precursor in blood initially is nonadherent to plastic, in contrast to monocytes, so that the precursors can be separated after overnight culture. Monocytes and fibroblasts are believed to comprise the majority of adherent cells and usually adhere to the substrate within about 6 to about 24 hours. Preferably nonadherent cells are separated from adherent cells between about 8 to 16 hours. Most preferably nonadherent cells are separated at about 12 hours. Any method which does not dislodge significant quantities of adherent cells may be used to separate the adherent from nonadherent cells. Preferably, the cells are dislodged by simple shaking or pipetting. Pipetting is most preferred.

To culture precursor cells from human blood from this primary culture, cells which have been depleted of cells that are not dendritic cell precursors are cultured on a substrate at a density of preferably about $5\times10^5$ cells per cm$^2$. After 5 days, with feedings every other day, cell aggregates appear (also referred to as "balls"). These aggregates may then be treated as described below.

The nonadherent cells from the primary culture are subcultured by transferring them to new culture flasks at a density sufficient to allow for survival of the cells and which results in the development over time of clusters of growing cells that are loosely attached to the culture surface or to the firmly adherent cells on the surface. These clusters are the nidus of proliferating dendritic cell precursors. As used herein "culture flasks" refers to any vessel suitable for culturing cells. It is desirable to subculture all of the non-adherent cells from the primary culture at a density of between about $2\times10^5$ cells and $5\times10^5$ cells per cm$^2$. Preferably at about $2.5\times10^5$ per cm$^2$. Cells are incubated for a sufficient time to allow the surface of the culture dish to become covered with a monolayer of tightly adherent cells including macrophages and fibroblasts affixed to which are aggregates of nonadherent cells. At this time, any nonadherent cells are removed from the wells, and the cellular aggregates are dislodged for subculturing. Preferably the cells from the aggregates are subcultured after about 10 days or when the number of aggregated cells per cm$^2$ reaches about 3 to $4\times10^5$.

For serially subculturing the aggregated cells, the aggregated cells are dislodged from the adherent cells and the aggregated cells are subcultured on a total surface area of preferably between about 2 to 5 times that of the surface area of the parent culture. More preferably the cells are subcultured on a surface area that is about 3 times the surface area of the parent culture. Cells having sheet-like processes typical of dendritic cells appear in the culture at about 4–7 days. Between about day 10 and day 17 of culture the number of single cells that can be recovered from a given surface area doubles. Both dendritic cell precursors and mature dendritic cells are present in the aggregates.

For producing dendritic cell from bone marrow, preferably the distinctive aggregates of proliferating, less mature dendritic cells are separated away from the stroma at about after about 4–6 d of culture. Large numbers of dendritic cells are released and it is this released population that expresses the cardinal features of mature dendritic cells. Because bone marrow initially contains a. greater proportion of dendritic cell precursors than blood, only about 4–6 days of culture of the cells obtained from bone marrow are necessary to achieve about the same number of cells which are obtained after about 10 to 25 days of culture of cells obtained from blood.

To further expand the blood derived population of dendritic cells, cell aggregates may be serially subcultured multiple times at intervals which provide for the continued proliferation of dendritic cell precursors. Preferably, aggregates are subcultured prior to the release into the medium of a majority of cells having the dendritic cell morphology, for example between about 3 and 30 days. More preferably aggregates of cells are subcultured between about 10 to 25 days in culture, and most preferably at 20 days. The number of times the cells are serially subcultured depends on the number of cells desired, the viability of the cells, and the capacity of the cultures to continue to produce cell aggregates from which dendritic cells are released. Preferably, cells can be serially subcultured for between about 1 to 2 months from when the nonadherent cells were subcultured or between about one to five times. More preferably cells are serially subcultured about two to three times. Most preferably cells are serially subcultured twice.

According to a preferred method, to serially subculture the cells of the primary and subsequent cultures, cells are dislodged by pipetting most of the aggregates of growing dendritic cells as well as some cells in the monolayer of growing macrophages and fibroblasts. Pipetting usually disrupts the aggregates, particularly the peripheral cells of the aggregates which are more mature. With time in culture, e.g., at 2 weeks, the aggregates of the growing dendritic cells become more stable and it is possible to dislodge the aggregates for separation by 1 g sedimentation.

Alternative approaches may be used to isolate the mature dendritic cells from the growing cultures. One is to remove cells that are nonadherent and separate the aggregates from cells attached to substrate and single cells by 1 g sedimentation. Dendritic cells are then released in large numbers from the aggregates over an additional 1–2 days of culture, while any mature dendritic cells can be isolated from other single cells by floatation on dense metrizamide as described (Freudenthal and Steinman, Proc. Natl. Acad. Sci. USA 87:7698–7702, 1990). The second method, which is simpler but essentially terminates the growth phase of the procedure, is to harvest all the nonadherent cells when the aggregates are very large, leave the cells on ice for about 20 minutes, resuspend vigorously with a pipette to disaggregate the aggregates and float the mature dendritic cells on metrizamide columns.

Typically the contents of five 16 mm wells are applied to a 6 ml column of 50% FCS -RPMI 1640 in a 15 ml conical tube [Sarstedt, 62.553.002 PS]. After at least 20 min, the applied medium and top 1 ml of the column are removed. RPMI is added, the aggregates are pelleted at 1000 rpm at 40° for 5 min, and the cells are suspended gently for subculture in fresh medium.

Various techniques may be used to identify the cells present in the cultures. These techniques may include analysis of morphology, detecting cell type specific antigens with monoclonal antibodies, identifying proliferating cells using tritiated thymidine autoradiography, assaying mixed leukocyte reactions, and demonstrating dendritic cell homing.

The dendritic cells besides being identified by their stellate shape may also be identified by detecting their expression of specific antigens using monoclonal antibodies.

A panel of monoclonal antibodies may be used to identify and characterize the cells in the GM-CSF expanded cultures. The monoclonal antibodies are reviewed elsewhere (23, 24 which are incorporated herein by reference).

Among the specific monoclonal antibodies suitable for identifying mature dendritic cells are: 1) those which bind to the MHC class I antigen (M1/42 anti-MHC class I [ATCC # TIB 126]); 2) those which bind to the MHC class II antigen (B21-2 anti-MHC class II [ATCC # TIB 229]; M5/114 anti-MHC class II [ATCC # TIB 120]); 3) those which bind to heat stable antigen (M1/69 anti-heat stable antigen [HSA, ATCC #T1B 125]); 4) 33D1 anti-dendritic cell antibodies [ATCC # TIB 227]; 5) those which bind to the interdigitating cell antigen (NLDC145 anti-interdigitating cell (13); and 6) those which bind to antigens in granules in the perinuclear region of mature dendritic cells (monoclonal antibodies 2A1 and M342, (23) Agger et al.). Other antigens which are expressed by the dendritic cells of the invention and which may be used to identify mature dendritic cells are CD44 (identified with monoclonal antibody 2D2C), and CD11b (identified with monoclonal antibody M1/70. The M1/69, M1/70, M1/42 monoclonal antibodies are described in Monoclonal antibodies, NY, Plenum 1980, ed. R. Kennett et al. pages 185–217 which is incorporated herein by reference. Those of skill in the art will recognize that other antibodies may be made and characterized which are suitable for identifying mature dendritic cells. Similarly, the production of dendritic precursor cells also facilitates the production of antibodies specific for dendritic precursor cells.

To identify and-phenotype the proliferating cells and their progeny, cultures may be labelled with tritiated thymidine to identify the cells in the S phase of mitosis. In addition to labelling the cells with a mitotic label, cells may also be co-labelled with monoclonal antibodies to determine when markers associated with mature dendritic cells are expressed. The distinctive phenotype of the dendritic cell precursors is stable so that for example, the dendritic cell progeny do not become macrophages even when maintained in macrophage colony stimulating factor (M-CSF).

Another index of dendritic cell maturity is the ability of mature dendritic cells to stimulate the proliferation of T-cells in the mixed leukocyte reaction (MLR). The ability of dendritic cells to migrate to lymph nodes, i.e., dendritic cell homing is another index of dendritic cell maturation which may be used to assess the maturity of the cells in culture.

The criteria that have become evident for identifying dendritic precursor cells according to the invention enables the identification of proliferating progenitors of dendritic cells in other organs. It is known that proliferating precursors give rise to the rapidly turning over populations of dendritic cells in spleen (15) and afferent lymph (16). The proliferation of leukocytes [other than T cells] occurs in the bone marrow, but it may be that for dendritic cells, the marrow also seeds the blood and other tissues with progenitors which then proliferate extensively as shown here. By being able to prepare the otherwise trace dendritic cell in large numbers according to the method of this invention, other previously unexplored areas of dendritic cell function may now be determined. Specifically, growing dendritic cells will facilitate molecular and clinical studies on the mechanism of action of these APCs, including their capacities to capture and retain antigens in an immunogenic form and act as adjuvants for the generation of immunity in vivo.

There is an increased interest in the use of constituent proteins and peptides to modulate T cell responses to complex microbial and cellular antigens in situ. Typically artificial adjuvants such as alum are required to produce a maximum immunogenic effect. Several antigens are known to be immunogenic when administered in association with dendritic cells but in the absence of additional adjuvants (1). The immunogenicity of dendritic cells in situ has been shown with for example contact allergens (45), transplantation antigens (46–49), and more recently foreign proteins (31,50,51). Other types of antigens include but are not limited to microbial, tumor and viral antigens. Dendritic cells serve directly as APCs in situ, because the T cells that are primed are restricted to recognize only antigens presented by the particular MHC class of the immunizing dendritic cells rather than host APCs (14,31,50,51). These observations, when coupled with data that dendritic cells are efficient at capturing protein antigens in an immunogenic form in situ (52–54), allow these APCs to be considered "nature's adjuvant". This invention therefore enables the utilization of dendritic cells by disclosing methods and compositions suitable for providing sufficient quantities of dendritic cell precursors in order to take advantage of their unique antigen presenting capabilities in clinical and therapeutic practices.

Dendritic cells are capable of processing complex antigens into those peptides that would be presented by self MHC products. Among the preferred embodiments of our invention is a method for using dendritic cells whereby the dendritic cell precursors internalize particulates during an early stage in their development from proliferating progenitors. We have established that stimulation of bone marrow suspensions with GM-CSF leads to the production of clusters of proliferating dendritic cell precursors. The cells that pulse label with 3H-thymidine in the clusters lack many of the characteristic markers of dendritic cells, e.g., stellate shape and antigenic features like NLDC-145 antigen and high levels of MHC class II. In pulse chase experiments, 3H-thymidine-labeled progeny with all the features of dendritic cells are released. We have found that cells within the aggregate also are phagocytic, and that in analogous pulse chase protocols, the progeny dendritic cells are clearly labeled with the phagocytic meal. When the particles are BCG organisms such as those causing tuberculosis, mycobacterial antigens associated with the dendritic cells are presented in a potent manner to T cells in vitro and in situ.

Foreign and autoantigens are processed by the dendritic cells of the invention to retain their immunogenic form. The immunogenic form of the antigen implies processing the antigen through fragmentation to produce a form of the antigen that can be recognized by and stimulate T cells. Preferably, such foreign or autoantigens are proteins which are processed into peptides by the dendritic cells. The relevant peptides which are produced by the dendritic cells may be extracted and purified for use as immunogens.

Peptides processed by the dendritic cells may also be used as toleragens to induce tolerance to the proteins processed by the dendritic cells or dendritic cell precursors. Preferably when used as toleragens, the processed peptides are presented on dendritic cells which have been treated to reduce their capacity to provoke an immune response as by inhibiting their accessory function by blocking accessory molecules such as B7 present on the dendritic cells.

The antigen-activated dendritic cells of the invention are produced by exposing antigen, in vitro, to the dendritic cells prepared according to the method of the invention. Dendritic cells are plated in culture dishes and exposed to antigen in a sufficient amount and for a sufficient period of time to allow the antigen to bind to the dendritic cells. The amount and time necessary to achieve binding of the antigen to the dendritic cells may be determined by immunoassay or binding assay. Other methods known to those of skill in the art may be used to detect the presence of antigen on the dendritic cells following their exposure to antigen.

Without being bound by theory, the information at present suggests that the development of dendritic cells proceeds by the following pathway [FIG. 11]. The dendritic cell precursors in both blood and marrow lack MHC class II antigens as well as B and T cell and monocyte markers [B220, CD3, thy-1, CD4/8], and the precursors are nonadherent. The precursors attach to the stroma and give rise to aggregates of class II positive cells. Perhaps the growing aggregates arise from a subset of strongly class II-positive cells that are found in the firmly adherent monolayer even at later time points. However, these firmly adherent, class II rich cells lack the MLR stimulatory activity of dendritic cells and may express substantial levels of Fcγ receptors and the F4/80 antigen. The final stage of development is that the loosely attached aggregate releases mature, nonproliferating dendritic cells. The latter have even higher levels of MHC class II [FIGS. 2–3] and can attach transiently to plastic, much like many of the dendritic cells released from spleen (25). As development occurs in the aggregate, there seems to be a reduction in the levels of cytoplasmic staining for Fcγ receptors and F4/80 antigen, and an increase in granule [M342, 2A1] and surface antigens [33D1, NLDC145] that are characteristic of dendritic cells. Lastly, accessory function for primary T-dependent immune responses increases as cells are released from the growing aggregates.

Mature dendritic cells, while effective in sensitizing T cells to several different antigens, show little or no phagocytic activity. To the extent that endocytosis is required for antigen processing and presentation, it was not previously evident how dendritic cells would present particle-associated peptides. Based on our work, it is now evident that progenitors to dendritic cells which this invention provides can internalize such particles for processing and presentation. The types of particles which may be internalized by phagocytosis include bacteria, viral, mycobacteria or other infectious agents capable of causing disease. Accordingly, any antigenic particle which is internalized and processed by the dendritic cell precursors of this invention is also suitable for making the various immunogens, toleragens and vaccines described as part of this invention. Processing of antigen by dendritic cells or dendritic cell precursors includes the fragmentation of an antigen into antigen fragments which are then presented.

Phagocytoses of particulate matter by dendritic cell precursors may be accomplished by culturing the dendritic cell precursors in the presence of particulate matter for a time sufficient to allow the cells to phagocytose, process and present the antigen. Preferably, culturing of the cells in the presence of the particles should be for a period of between 1 to 48 hours. More preferably, culturing cells in the presence of particulate matter will be for about 20 hours. Those of skill in the art will recognize that the length of time necessary for a cell to phagocytose a particle will be dependent on the cell type and the nature of the particle being phagocytosed. Methods to monitor the extent of such phagocytosis are well known to those skilled in the art.

Cells should be exposed to antigen for sufficient time to allow antigens to be internalized and presented on the cell surface. The time necessary for the cells to internalize and present the processed antigen may be determined using pulse-chase protocols in which exposure to antigen is followed by a wash-out period. Once the minimum time necessary for cells to express processed antigen on their surface is determined, a pulse-chase protocol may be used to prepare cells and antigens for eliciting immunogenic responses.

The phagocytic dendritic precursor cells are obtained by stimulating cell cultures comprising dendritic precursor cells with GM-CSF to induce aggregates of growing dendritic cells. These dendritic precursor cells may be obtained from any of the source tissues containing dendritic cell precursors described above. Preferably, the source tissue is bone marrow or blood cultures. Cells within these aggregates are clearly phagocytic. If the developing cultures are exposed to particles, washed and "chased" for 2 days, the number of MHC-class II rich dendritic cells increases substantially and at least 50% contain internalized particles such as BCG mycobacteria or latex particles. The mycobacteria-laden, newly developed, dendritic cells are much more potent in presenting antigens to primed T cells than corresponding cultures of mature dendritic cells that are exposed to a pulse of organisms.

A similar situation pertains when BCG-charged, dendritic cells are injected into the footpad or blood stream of naive mice. Those dendritic cells that have phagocytosed organisms induce the strongest T cell responses to mycobacterial antigens in draining lymph node and spleen. The administration of antigens to GM-CSF induced, developing dendritic cells—by increasing both antigen uptake and cell numbers—will facilitate the use of these APCs for active immunization in situ. The production of such strong immunogenic responses due to the presentation of antigen by the dendritic cells makes these cells and this system particularly desirable as adjuvants useful for producing immunogenic responses in individuals. Such immunogenic responses and the development of antibodies to the presented antigens may be used to treat ongoing infections or prevent future infections as with a vaccine. The use of dendritic cells to produce a therapeutic or prophylactic immune response in an individual may be particularly useful to treat or prevent infection by drug resistant organisms, such as, for example, the BCG mycobacterium causing tuberculosis.

Immunogenicity of ingested particles can be obtained with BCG myccbacteria (FIGS. 12–13). In any inoculum of the BCG vaccine, there are live bacilli [approximately 50% of the bacilli act as colony forming units], dead bacilli, and probably a number of mycobacterial proteins. The phagocytosed pool of BCG is being presented to T cells by dendritic cells. This is evident after comparing the presentation of mycobacterial antigens with bovine serum albumin (BSA), a component of the serum in which the dendritic cells are grown. All the APC populations were comparable in presenting BSA, but dendritic cells that had phagocytosed the most BCG were the most effective APCs for mycobacteria (FIGS. 12 and 13, ♦). BCG particle uptake, therefore, accounts for the bulk of the mycobacterial priming by the dendritic cell precursors.

Another embodiment of this invention is therefore to pulse dendritic cell precursors with mycobacteria tuberculosis bacteria antigen, including for example BCG antigen, to induce host resistance to mycobacteria infection, a matter of importance given the need to develop better vaccination and treatment protocols for tuberculosis, including the drug resistant variety (78).

In effect, the pulse and chase protocol which may be used to charge developing dendritic cells with organisms according to our invention allows the two broad components of immunostimulation to take place sequentially. These components are a) antigen capture and presentation, here the capture of particulates by immature dendritic cells, and b) development of potent accessory or immunostimulatory functions during the chase period. The situation is comparable to that seen in the handling of soluble proteins (4,6) and particles (74) by epidermal Langerhans cells. Each of the two broad components of APC function entails many subcomponents. For example, immature dendritic cells not only are more phagocytic but display other features needed for antigen presentation such as active biosynthesis of abundant MHC class II molecules and invariant chain (6,7) and numerous acidic endocytic vacuoles (36).

The capacity to charge APCs with antigens using pulse chase protocols may be a special feature of dendritic cells. Prior studies with macrophages and B cells had suggested that T cell epitopes are short-lived (75). The results described here and elsewhere (6,14,71) indicates that immunogenic peptides can be long lived on dendritic cells at least 2 days prior to injection into mice. This retention capacity should enable dendritic cells to migrate and sensitize T cells in draining lymphoid tissues over a period of several days (14,50,51).

An important feature of the dendritic cells of this invention is the capacity to efficiently present microbial and other antigens on both class I and II products. In the case of BCG, the bulk of the primed cells are CD4+ T cells, most likely because the antigenic load is handled by the endocytic pathway and MHC class II products (76). In the case of influenza, it has been found that the class I pathway for inducing CD8+ cytotoxic T lymphocytes (CTL) requires adequate delivery of antigen (infectious virus) into the cytoplasm, whereas the purely endocytic pathway delivers noninfectious virions for presentation only to CD4+ helpers (77). Developing dendritic cell cultures provides an opportunity for charging MHC class I products with peptide, since cell proliferation allows various methods of gene insertion (as with retroviral vectors) to be applied.

According to this further embodiment of the invention, the proliferating dendritic cells may be injected with a vector which allows for the expression of specific proteins by the dendritic cells. These viral proteins which are expressed by the dendritic cell may then be processed and presented on the cell surface on MHC I receptors. The viral antigen-presenting cells or the processed viral antigens themselves may then be used as immunogens to produce an immunogenic response to the proteins encoded by the vector.

Vectors may be prepared to include specific DNA sequences which code and express genes for proteins to which an immunogenic response is desired. Preferably, retroviral vectors are used to infect the dendritic cells. The use of retroviral vectors to infect host cells is known to those skilled in the art and is described in WO 92/07943 published May 14, 1992 and in Richard C. Mulligan, "Gene Transfer and Gene Therapy:Principle, Prospects and Perspective" in *Enology of Human Disease at the DNA Level*, Chapter 12. J. Linsten and A. Peterson, eds. Rover Press, 1991 which are both incorporated herein by reference.

By using developing dendritic cells to charge MHC class I and/or II products, several desirable components of T cell modulation in situ can be achieved. Antigen uptake and presentation by immature progenitors, allows the APC to tailor the peptides that are appropriate for an individual's MHC products, and increases the number of specialized stimulatory APCs. These properties of dendritic cell progenitor populations meet many of the demands for using cells as vehicles for active immunization and immunotherapy in situ.

The present invention provides for the first time a method of obtaining dendritic cells in sufficient quantities to be used to treat or immunize animals or humans with dendritic cells which have been activated with antigens. In addition, dendritic cells may be obtained in sufficient quantities to be useful as reagents to modify antigens in a manner to make the antigens more effective as T-cell dependent antigens.

To use antigen-activated dendritic cells as a therapeutic or immunogen the antigen-activated dendritic cells are injected by any method which elicits an immune response into a syngeneic animal or human. Preferably, dendritic cells are injected back into the same animal or human from whom the source tissue was obtained. The injection site may be subcutaneous, intraperitoneal, intramuscular, intradermal, or intravenous. The number of antigen-activated dendritic cells reinjected back into the animal or human in need of treatment may vary depending on inter alia, the antigen and size of the individual. A key feature in the function of dendritic cells in situ is the capacity to migrate or home to the T-dependent regions of lymphoid tissues, where the dendritic cells would be in an optimal position to select the requisite antigen-reactive T cells from the pool of recirculating quiescent lymphocytes and thereby initiate the T-dependent response.

According to the preferred method of stimulating an immune response in an individual, a tissue source from that individual would be identified to provide the dendritic cell precursors. If blood is used as the tissue source preferably the individual is first treated with cytokine to stimulate hematopoieses. After isolation and expansion of the dendritic cell precursor population, the cells are contacted with the antigen. Preferably, contact with the antigen is conducted in vitro. After sufficient time has elapsed to allow the cells to process and present the antigen on their surfaces, the cell-antigen complexes are put back into the individual in sufficient quantity to evoke an immune response. Preferably between $1 \times 10^6$ and $10 \times 10^6$ antigen presenting cells are injected back into the individual.

The novel antigens of the invention are prepared by combining substances to be modified or other antigens with the dendritic cells prepared according to the method of the invention. The dendritic cells process or modify antigens in a manner which promotes the stimulation of T-cells by the processed or modified antigens. Such dendritic cell modified antigens are advantageous because they can be more specific and have fewer undesirable epitopes than non-modified T-dependent antigens. The dendritic cell modified antigens may be purified by standard biochemical methods. For example, it is known to use antibodies to products of the major histocompatibility complex (MHC) to select MHC-antigenic peptide complexes and then to elute the requisite processed peptides with acid [Rudensky et al., *Nature* 353:622–7 (1991); Hunt et al., *Science* 255: 1261–3 (1992) which are incorporated herein by reference].

Antigen-activated dendritic cells and dendritic cell modified antigens may both be used to elicit an immune response against an antigen. The activated dendritic cells or modified antigens may by used as vaccines to prevent future infection or may be used to activate the immune system to treat ongoing disease. The activated dendritic cells or modified antigens may be formulated for use as vaccines or pharmaceutical compositions with suitable carriers such as physiological saline or other injectable liquids. The vaccines or pharmaceutical compositions comprising the modified antigens or the antigen-activated dendritic cells of the invention would be administered in therapeutically effective amounts sufficient to elicit an immune response. Preferably, between about 1 to 100 micrograms of modified antigen, or its equivalent when bound to dendritic cells, should be administered per dose.

The present invention also provides a method and composition for treating autoimmune disease. Such autoimmune diseases include but are not limited to juvenile diabetes, multiple sclerosis, myasthenia gravis and atopic dermatitis. Without being bound by theory, it is believed that autoimmune diseases result from an immune response being directed against "self-proteins", i.e., autoantigens that are present or endogenous in an individual. In an autoimmune response, these "self-proteins" are being presented to T cells which cause the T cells to become "self-reactive". According to the method of the invention, dendritic cells are pulsed with the endogenous antigen to produce the relevant "self-peptide". The relevant self-peptide is different for each individual because MHC products are highly polymorphic and each individual MHC molecules might bind different peptide fragments. The "self-peptide" may then be used to design competing peptides or to induce tolerance to the self protein in the individual in need of treatment.

Because dendritic cells can now be grown from precursors according to the methods and principles identified here, and because dendritic cells can modify antigens to produce killer T cells, the compositions of this invention are particularly useful as vaccines towards viruses and tumor cells for which killer T cells might provide resistance.

EXAMPLES

Example 1

Production of Mouse Dendritic Cells In Vitro From Proliferating Dendritic Cell Precursors From Blood Materials A. Mice: BALB/C, BALB/C×DBA/2 F1, BALB/C× C57BL/6 F1, C57BL/6×DBA/2 F1, and C57BL/6 males and females, 6–8 weeks of age were purchased from Japan SLC Inc [Shizuoka, Japan], the Trudeau Institute [Saranac Lake, N.Y.], and Charles River Wiga [Sulzberg, FRG]. Four preparations of rGM-CSF were evaluated with similar results, the yield of dendritic cells reaching a plateau with 30–100 U/ml. The preparations were from Dr. S. Gillis, Immunex Corp, Seattle Wash.; Genetics Institute [supernatant from COS cells transfected with mGM-CSF; used at 30 U/ml or greater]; and Dr. T. Sudo [supernatant from CHO cells transfected with the expression vector, pHSmGM-CSF (22), and *E.Coli* expressed material].

B. Blood Preparation: Blood was obtained by cardiac puncture or from the carotid artery. The blood was diluted in, or allowed to drip into, RPMI-1640 with 100 U/ml heparin [about 2 ml/mouse]. Blood cells were pelleted at 1000 rpm at 4°, resuspended in RPMI 1640, and sedimented again. The pellet was suspended in 1 ml RPMI 1640 per mouse and mixed with an equal volume of 1.66% ammonium chloride in distilled water to lyse the red cells. After 2 min at room temperature, the suspension was spun at 1000 rpm at 4°. The pellet, which still contained red cells, was resuspended again in 0.5 ml RPMI and 0.5 ml $NH_4Cl$ for 2 min, diluted in RPMI, and sedimented again. After 2 more washes, most platelets and red cells had been depleted and a population of blood leukocytes had been obtained.

C. Aggregates of proliferating dendritic cells from blood supplemented with GM-CSF Blood leukocytes, usually from CxD2 F1 mice, were cultured in 16 mm tissue culture wells [24 well dishes, Costar, #25820] in medium (1 ml per well) supplemented with GM-CSF at 30 U/ml and at $1.5 \times 10^6$ cells/well. The medium was RPMI 1640 supplemented with 5% fetal calf serum [JRH Biosciences, Lenexa, Kans.], 50 uM 2-ME, 20 ug/ml gentamicin, and recombinant mouse GM-CSF. After overnight culture, many monocytes adhered and the nonadherent cells were transferred to new 16 mm wells. The adherent cells did not develop dendritic cell colonies, but during the next week, the nonadherent populations exhibited three changes. First, most of the lymphocytes and granulocytes died or could be removed by washing. Second, the surface of the well became covered with a monolayer of tightly adherent cells that included macrophages and fibroblasts. Third, affixed to scattered sites on the monolayer, there developed small aggregates of cells. The cultures were fed with GM-CSF (30 u/ml) at day 6–7 and then ever 3 days by aspirating 0.5–0.75 ml of the medium and adding back an equal volume of fresh medium with GM-CSF. The aggregates continued to expand in number and size. At about day 10, the cells were ready to be subcultured. Any residual loose cells could be rinsed off prior to dislodging the aggregates into fresh medium and GM-CSF. About 0.8–1 million dislodged cells per original well were divided into 3 subculture wells.

Most of the aggregates disassembled during this first subculture, while the bulk of the adherent monolayer remained attached to the original well. Upon transfer, most of the cells in the dislodged aggregates adhered as single cells to the new culture well but over a period of 2–3 days, aggregates reappeared. The aggregates again were affixed to adherent stromal cells, but these adherent cells were much less numerous than the dense monolayer in the original culture. Over the next 4–7 days, aggregates filled the wells. These colonies were often larger than those of the original wells and were covered with many sheet-like processes typical of dendritic cells. It was more difficult to count cells at this point, since many of the aggregates contained a core of tightly associated cells. However, the number of single cells that could be recovered per well expanded about 2 fold between days 10 and 17 of culture.

If the cultures were allowed to overgrow, some cells with the morphology of dendritic cells were released. More typically, the cells were not allowed to overgrow and the aggregates were dislodged and subcultured again at about 20 days. Prior to subculture, the aggregates could be purified from free cells by ig sedimentation. Such separations were more easily performed with longer periods of culture, i.e., it was easier to isolate intact aggregates at 3 vs. 2 vs. 1 week of culture. With additional subculturing, the number of aggregates that were produced per well was progressively reduced. However colonies of growing cells, as confirmed by 3H-TdR labeling and autoradiography [below], could be generated in subcultures for 1–2 months. Following subculturing at 2–3 weeks, typical single dendritic cells were now released into the medium. By direct observation with video recording, these released cells had the active motility of dendritic cells, continually extending and retracting large veils or sheet-like processes. In the presence of continued GM-CSF, one observed both free dendritic cells as well as expanding colonies. In the absence of GM-CSF, only free dendritic cells were released and the aggregates essentially fell apart and did not reform in the medium and colonies of aggregates did not develop. The yields of free dendritic cells per subculture ranged from $0.3$–$2.5 \times 10^5$.

In summary, from a starting blood mononuclear culture of $1.5 \times 10^6$ cells, where dendritic cells were difficult to detect, we on average obtained 5–10 subcultures each with at least $3$–$10 \times 10^4$ released dendritic cells at 3 weeks, as well as many aggregates capable of further proliferation. Therefore aggregates of growing cells were developing in mouse blood supplemented with GM-CSF, and these aggregates were covered with dendritic cells many of which could be released spontaneously into the medium.

D. Phenotype of the cell aggregates and dendritic cells released therefrom

Cytospin preparations were made in a Shandon cytocentrifuge using $3$–$10 \times 10^4$ cells. The slides were stored with desiccant prior to fixation in acetone and staining with mAb followed by peroxidase mouse anti-rat Ig [Boehringer Mannheim Biochemicals, #605–545] or rabbit anti-hamster Ig [Accurate Chemical & Scientific Corp, # JZY-036–003]. The preparations were stained with Giemsa and mounted in Permount for bright field analysis. For cytofluorography [FACScan, Becton Dickinson], aliquots of cells were stained with primary rat or hamster mAb followed by FITC mouse anti-rat Ig [Boehringer, #605–540] or biotin rabbit anti-hamster Ig [Accurate, JZY-066-003] and FITC-avidin.

Cytospin preparations of 2–3 week cultures were examined with a panel of mAb and an immunoperoxidase method. The released cells, and many of the cells that could be dislodged from the periphery of the aggregate, were similar in their stellate shape and phenotype. Most of the cells stained strongly with mAb to MHC class II, the CD45 leukocyte common antigen, CR3 receptor CD11b, and heat stable antigen (HSA), and CD44. Staining with mAbs to the Fc receptor [2.4G2] and macrophage F4/80 antigen (MAC) was weak or undetectable in >95% of the cells. The cultures contained only rare B cells [B220 mAb, RA-3], T cells [thy-1 mAb, B5-5], or granulocytes [GRAN, mAb RB6]. Some cells at the periphery of the aggregate, and many of the cells that were released from the aggregates, were stained with two markers that are largely restricted to dendritic cells. The interdigitating cell antigen [mAb NLDC 145 (13), IDC], which also binds to thymic epithelium, stained many but not all of the dendritic profiles. Virtually all of the dendritic profiles stained with mAbs 2A1 and M342 stain granules in the perinuclear region of mature dendritic cells, B lymphocytes, as well as interdigitating cells in sections through the T areas of lymphoid organs. Macrophages from many sites [blood monocytes; peritoneal cavity macrophages; macrophages in sections of lymph node, thymus, spleen] do not contain 2A1 or M342-reactive granules.

Cytofluorography was used to gain semi-quantitative information on the expression of antigens at the cell surface. A panel of mAb were applied to two populations: cells that could be dislodged from the aggregates by Pasteur pipetting, and cells that were released spontaneously when the aggregates were subcultured for 1 day. These "dislodged" and "released" populations were identical in their dendritic shape and in phenotype but for some exceptions that are considered below. The phenotype of the released cells is shown in FIG. 2, and the few differences between aggregated and released cells are in FIG. 3. Virtually all the dendritic cells developing in and from the aggregates expressed high levels of the leukocyte common [CD45, mAb M1/9.3] and heat stable [mAbs M1/69 and J11d] antigens, as well as high levels of CD44 and CD11b [mAb M1/70]. Low levels of the following antigens were detected on the cell surface: the dendritic cell antigen 33D1, the macrophage marker F4/80, the Fcγ receptor antigen 2.4G2, the p55 IL-2 receptor CD25 antigen 3C7, and the CD11c integrin N418 [FIG. 2]. These antigens were noted on all cells by FACS even though many of the antigens like F4/80 and 2.4G2 were weak or absent in the cytoplasm with an immunoperoxidase method. Several antigens were absent: RB6 granulocyte, RA3 B cell, B5-5 thy-1, GK 1.5 CD4, and SER-4 marginal zone macrophage [FIG. 2].

Expression of class I and II MHC products by the dendritic cells in these cultures was very high but nonetheless bimodal [FIG. 2 and FIG. 3]. Most of the dendritic cells that were dislodged from the aggregates had somewhat lower levels of MHC class I and II, while dendritic cells that were released from the aggregates had very high levels of MHC products. The other marker that was different in the released and loosely attached dendritic cells was NLDC 145 which was higher in the released population. [FIG. 3, top panels]. We conclude that the phenotype of the cells that arise from the proliferating aggregates is very much like that seen in cultured dendritic cells from skin, spleen, and thymus (24, 28) with the exception that the M1/70 CD11b marker is more abundant.

E. 3H-TdR autoradiography to verify growth of dendritic cell precursors

After 2 and 3 weeks in liquid culture, the wells contained numerous expanding aggregates of cells, and in some cases were already releasing nonadherent dendritic cells in large numbers. Cultures were labeled with 3H-thymidine to identify and phenotype the proliferating cells and their progeny. For pulse labeling, 3H-TdR was added to the cultures [6 Ci/mM, 1 uCi/ml final]. 2 h later, the medium was replaced with 3H-TdR free medium, and the cultures were separated into nonadherent released cells and residual adherent aggregates for examination on cytospin preparations [Shandon Inc, Pittsburgh Pa., #59900102]. The cytospin cells were stained for specific antigens with mAb and immunoperoxidase as above. Also, the slides were dipped in photographic emulsion [Kodak autoradiography emulsion type NTB2 #165–4433] for exposure [5 days] prior to development, staining with Giemsa, and mounting in Permount. For pulse chase experiments, a lower dose of 3H-TdR was used to maintain cell viability, but the cells were handled similarly otherwise. The pulse was applied at 0.1 uCi/ml for 2 h or for 16 h, the latter to provide higher initial labeling indices. The cells were washed and chased for 1–3 days prior to harvesting and analysis as above with immunoperoxidase, autoradiography, and Giemsa staining.

The 2 and 3 week cultures were exposed to 3H-TdR and examined for proliferative activity. The labeled cells were washed, spun onto slides, and the cytospins stained with mAb and an immunoperoxidase method prior to dipping and exposure to photographic emulsion. Important markers were mAbs 2A1 and NLDC-145 which recognize intracellular granules and a cell surface antigen in mature dendritic cells respectively.

When cultures were labeled with a 2 h pulse of 3H-TdR, it was apparent that the labeling index in the aggregates was very high, at least 10–15% of the profiles in the aggregates being in S phase. In contrast, if 3H-TdR was applied to cultures that were releasing typical nonadherent dendritic cells, the released fraction contained only rare labeled profiles. If GM-CSF was removed, 3H-TdR labeling ceased within a day. Virtually all the 3H-TdR labeled cells in the aggregate failed to label with mAb to markers found on mature dendritic cells i.e., 2A1 and NLDC145. The level of staining with anti-MHC class II mAb was less on the cells in S-phase than in the released dendritic cell populations [not shown].

Pulse chase experiments were then done to establish that labeled cells in the aggregate were giving rise to typical dendritic cells. Cultures were first exposed to a low dose of 3H-TdR, either for 2 h or for 16 h, the latter to label a larger percentage of the cells in the aggregates. The wells were washed free of radiolabel, and then the aggregates were dislodged and separated from free cells by 1 g sedimentation. The aggregates were transferred to fresh medium without radiolabel, and over the next 1–3 days of culture, many dendritic cells were released into the medium. When the "chased" cultures were examined, several findings were apparent. The labeling index remained high, i.e., most of the progeny of cells that were proliferating in the aggregates were not being lost from the cultures. Second, the grain counts were diluted several fold from those apparent in the original pulse. Third, cells expressing the markers of mature dendritic cells [NLDC145, the 2A1 granular antigen, high levels of MHC class II] were now radiolabeled. Therefore the cellular aggregates that GM-CSF was inducing in cultured mouse blood were actively proliferating and releasing nonproliferating progeny with many of the typical cytologic and antigenic features of mature dendritic cells including the 2A1 granular antigen, the NLDC145 marker, and high levels of MHC class II.

F. Accessory cell function for T cell proliferative responses

MLR stimulating activity was monitored in the GM-CSF treated blood cultures. Cells from the blood cultures were exposed to 1500 rads [137Cs] and applied in graded doses to $3 \times 10^5$ purified syngeneic or allogeneic T cells in 96 well, flat-bottomed microtest wells. The T cells were nylon wool nonadherent, spleen and lymph node suspensions that were treated with anti-Ia plus Jlld mAbs and complement to remove residual APC. 3H-TdR uptake was measured at 72–86 h [6 Ci/mM, 4 uCi/ml final].

Initially there was little or no MLR stimulating activity [FIG. 4, *]. Some stimulating activity was noted at day 1 of culture [FIG. 4, O]. An examination of cytospin preparations revealed that these 1 day nonadherent blood cells had a low [<0.3%] but clear subset of Ia-rich, dendritic profiles. By day 7, when the proliferating aggregates were first evident on the monolayer, the stimulating activity of the dislodged aggregates had increased further, but was still 100 times less in specific activity than typical dendritic cells [FIG. 4, compare Δ and ●]even though most of the cells at day 7 and subsequent time points were MHC class II positive. By day 14, at which time typical nonadherent dendritic cells were just beginning to be released from the aggregates, the nonadherent population had considerable MLR stimulating activity, [FIG. 4, ▽]. After 3 weeks, typical mature dendritic cells had become abundant, and these indeed stimulated comparably to their splenic counterparts [FIG. 4, compare ◇ and ●]. Other cells in the culture, such as those dislodged from the aggregates, were about 10 fold less active than dendritic cells (FIG. 4, ◆]. We conclude that the aggregates of proliferating dendritic cells have some MLR stimulating activity but that it is the mature released cells that are fully potent, some 100–300 times more active on a per cell basis than the populations in the starting culture at 1–7 days. During day 7–20 of culture, total cell numbers also expanded at least 5–10 fold.

G. Homing activity of dendritic cells in vivo

A second specialized feature of dendritic cells is their capacity to home to the T areas of peripheral lymphoid tissues (8,10). Dendritic cells or other cell types were labeled at $2–10 \times 10^6$/ml with carboxyfluorescein for 10 min on ice [Molecular Probes C-1157; 30 uM final concentration in Hanks balanced salt solution (HBSS) with 5% FCS], washed in RPMI 1640, and injected in a volume of 50 ul RPMI-1640 into the foot pads. One day later, the draining popliteal lymph nodes were removed, frozen in OCT medium, and sectioned [10μ] in a cryostat. To sample the entire node, we took duplicate specimens at regular intervals. The sections were applied to multiwell slides [Carlson Scientific microslides #111006], stored at −20° C., dried in a desiccator 30' prior to use [or left at room temp overnight], fixed in acetone, and stained with a peroxidase conjugated rabbit anti-FITC antibody [Dakopatts, P404]. To verify that the dendritic cells in the lymph node were in the T-dependent areas as described (8), we added appropriate mAb to B cell, T cells, macrophages, or dendritic cells and visualized the latter with alkaline phosphatase conjugated mouse anti-rat Ig [Boehringer Mannheim, #605–5357] plus a chromogen kit [Biomeda Corp, Foster City Calif. #S04]. We then blocked endogenous peroxidase with "Endo Blocker" [Biomeda Corp, #M69] followed by the peroxidase anti-FITC as above.

Blood leukocytes, even when given at a dose of $10^6$ cells per footpad, failed to home to the lymphoid organ. When we tested dendritic cells that had been generated with GM-CSF from blood, homing to the T area was observed with injections of 200,000 cells. The selective localization to the T areas was confirmed by double labeling the specimens with mAb that stain B cells or T cells. Therefore dendritic cells produced in culture have the key functional features of this lineage: homing to the T-dependent regions and strong accessory activity.

H. Requirements for generating dendritic cell colonies from blood

The surface phenotype of the blood cell that gives rise to the dendritic cell colonies was assessed by treating the starting population with antibodies and complement. Treatment with either 33D1 anti-dendritic cell, anti-MHC class II, or anti thy-1 did not eliminate the colony forming unit [not shown]. Instead, removal of thy-$1^+$ or Ia$^+$ cells enriched colony numbers several fold. CSF's other than GM-CSF were also tested, either at the start of the 1–3 week culture, or upon transfer of 2–3 week old aggregates to form veiled cells. None of the CSF's tested, i.e., IL-3, M-CSF, G-CSF, SCF, supported the formation of colonies or mature dendritic cells. Therefore the growing dendritic colonies are very much dependent upon GM-CSF.

In an effort to identify proliferating precursors to the dendritic cell system, we set up cultures from several tissues that lacked mature dendritic cells and supplemented these with different growth factors particularly the CSF's [M-CSF, G-CSF, IL-3, GM-CSF, IL-1, and SCF]. Dendritic cell precursors were not observed from neonatal epidermis, which contains mainly Ia$^-$ Langerhans cells (29). To avoid overgrowth of granulocytes in bulk bone marrow cultures which may make the identification of typical cell colonies or large numbers of dendritic cells difficult, it is preferred to remove the nonadherent, proliferating granulocytes on days 2 and 4. Blood, which has few typical dendritic cells in the mouse (30), proved to be very effective for obtaining dendritic cell precursors. Growing cell aggregates appeared after about 6 days in culture, and these were often covered with profiles having the unusual and motile processes of dendritic cells. With time, typical nonadherent dendritic cells were released. The latter had the morphology and movement of dendritic cells as previously described in cultured mouse spleen, mouse skin, lymph from several species, and human blood (25–27). Therefore to identify proliferating dendritic cells, it seems critical to begin with an appropriate starting population, preferably blood, and to supplement the culture with GM-CSF.

Without wishing to be bound by any theory, we think that the initial aggregates that appeared in the cultures represented clones, since very small groups of 4–6 cells were observed early on e.g., day 5. We tried to prove that the aggregates were clonal by mixing blood cells from strains that were distinguished with markers to polymorphic antigens like CD44 and MHC class II. However we could not complete the experiments since we found that mouse strains differed in the number and speed with which colonies developed. BALB/C and DBA [and F1 strains derived therefrom] were the most active; B6 and B10 were several times less active; and strains like CBA/J, C3H/He, and A/J were poor sources of proliferating, dendritic cell aggregates.

The precursors to the aggregates of proliferating dendritic cells were not typical monocytes or dendritic cells, because the number of aggregates that developed could be increased substantially if one depleted monocytes by adherence or Ia-positive cells with antibody and complement. Without wishing to be bound by theory, we tentatively conclude that blood contains an Ia-negative precursor that forms a proliferating aggregate. In the aggregate, dendritic cells mature and are released as nonproliferating progeny.

The formation of aggregates of dendritic cells required exogenous GM-CSF. If the aggregates were placed in macrophage or granulocyte-restricted CSF's [M-CSF, G-CSF], proliferation ceased and neither macrophages nor granulocytes were formed. Because the cultures contained macrophages and some stromal cells, in addition to the dendritic cell aggregates, it was possible that other cytokines were being produced that were critical to the formation of dendritic cells. It appears however that the cells in the aggregates have lost responsiveness to M- and G-CSF, and that dendritic cells represent a distinct myeloid pathway of development. Perhaps, without wishing to be bound by theory, the pathway originates from a common precursor in which the dendritic cell lineage is an offshoot that no longer responds to macrophage and granulocyte restricted CSF's.

Labeling with 3H-thymidine, using pulse and pulse-chase protocols, was important in establishing the precursor-product relationships that were taking place in these liquid cultures. In a 2 h pulse, virtually every labeled cell lacked two typical markers of mature dendritic cells, i.e., the NLDC-145 interdigitating cell surface antigen (13) and the recently identified 2A1/M342 granular cytoplasmic antigens (34). These mAb do not stain most macrophage populations that we have examined either as isolated cells [blood, spleen, peritoneal macrophages] or in sections [thymic cortex, spleen red pulp, lymph node medulla]. In pulse chase protocols, large numbers of labeled progeny were released from the aggregates, and these released cells were nonadherent, motile, and strongly stimulatory in the MLR. After combined autoradiography and immunoperoxidase labeling, the labeled progeny carried the granular antigens, the NLDC-145 antigen, and very high levels of MHC class II. Each of these cytologic and antigenic. markers are largely restricted to dendritic cells.

Without wishing to be bound by theory, we believe that maturation to typical nonproliferating dendritic cells occurred within the aggregate. The aggregates were covered with cells with the sheetlike or veiled processes of dendritic cells. Cells with markers of mature dendritic cell markers [high MHC class II, 2A1 positive granules, NLDC antigen] were also observed at the periphery of the cell aggregates. However, it was difficult to isolate the aggregate intact, i.e., without dislodging these more mature cells. The mechanism whereby dendritic cells matured and left the aggregate was not clear. Maturation was enhanced in older cultures [>2 weeks] or by removing adherent stroma cells. Both proliferation and maturation was blocked if the cultures contained too many fibroblasts.

The functional maturation that occurred in the proliferating aggregate is striking. The dendritic cells that were generated in culture were potent MLR stimulators. 100 dendritic cells induced a much stronger primary MLR than 100,000 blood leukocytes. The increase in stimulating activity per Ia-positive cell was at least 2 logs between the time that the aggregates first appeared and the time that typical dendritic cells were released in large numbers. Over this time period, cell recovery increased 5–10 fold. Also the dendritic cell progeny homed in a precise way to the T cell area of lymph node, another functional property that was not detectable in blood cells [data not shown].

Example 2

Generation of Large Numbers of Dendritic Cells From Mouse Bone Marrow Cultures Supplemented With GM-CSF Materials A. Mice: Female BALB/C, male DBA/2, and female C57BL/6 mice, 7 wks old, were purchased from Japan SLC [Hamamatsu, Shizuoka, Japan]. BALB/C×DBA/2 F1, of both sexes 7–10 wks old, were from Japan SLC and the Trudeau Institute, Saranac Lake, N.Y. Reagents: The culture medium was RPMI-1640 [Nissui, Tokyo, Japan; GIBCO, Grand Island, N.Y.] supplemented with 5% FCS, 50 µM 2-Mercaptoethanol, and 20 µg/ml gentamicin. Murine rGM-CSF [$10^8$U/mg protein] was kindly provided by Kirin Brewery Co [Maebashi, Gumma, Japan]. A panel of rat and hamster mAbs to mouse leukocyte antigens is described elsewhere (23, 24). FITC- and peroxidase-conjugated mouse anti-rat IgG were purchased from Boehringer Mannheim [Indianapolis, Ind.] and FITC- and peroxidase-conjugated goat anti-hamster Ig [γ and L-chain] were from Jackson Immunoresearch Lab [Westgrove, Pa.] and Caltag [San Francisco, Calif.] respectively.

B. Bone marrow cultures: After removing all muscle tissues with gauze from the mouse femurs and tibias, the bones were placed in a 60 mm dish with 70% alcohol for 1 min, washed twice with PBS, and transferred into a fresh dish with RPMI-1640. Both ends of the bones were cut with scissors in the dish, and then the marrow was flushed out using 2 ml of RPMI-1640 with a syringe and 25 G needle. The tissue was suspended, passed through nylon mesh to remove small pieces of bone and debris, and red cells were lysed with ammonium chloride. After washing, lymphocytes and Ia-positive cells were killed with a cocktail of mAbs and rabbit complement for 60 min at 37° C. The mAbs were GK 1.5 anti-CD4, HO 2.2 anti-CD8, B21-2 anti-Ia, and RA3-3A1/6.1 anti-B220/CD45R all obtained from the ATCC [TIB 207, 150, 229, and 146 respectively]. $7.5-10 \times 10^5$ cells were placed in 24 well plates [Nunc, Naperville, Ill.] in 1 ml of medium supplemented with 500–1000 U/ml rGM-CSF. The cultures were usually fed every 2 d for about 2 to 10 days, by gently swirling the plates, aspirating ¾ of the medium, and adding back fresh medium with GM-CSF. An object of these washes was to remove nonadherent granulocytes without dislodging clusters of developing dendritic cells that were loosely attached to firmly adherent macrophages.

To enrich for growing dendritic cells, we utilized a procedure similar to that described for the mouse blood cell cultures of Example 1. Briefly, the aggregates of attached cells were dislodged with Pasteur pipettes and applied to 6 ml columns of 50% FCS-RPMI 1640. Residual granulocytes in the cultures, often in aggregates as well, were easily dissociated at this step. Upon 1g sedimentation of the dislodged cells, clusters moved to the bottom of the tube and single granulocytes were left at the top. The aggregates were subcultured at $2-3 \times 10^5$/ml in fresh medium with GM-CSF, typically for 1 day in 16 mm wells. After overnight culture, large numbers of typical dendritic cells were released. Adherent macrophages also expanded in these cultures, but most remained firmly adherent to the culture surface.

C. Cytological Comparison of Dendritic Cell Precursors and Ia-negative. Bone Marrow Nonlymphocytes To compare the released [dendritic-cell enriched; top] and adherent [macrophage-enriched; bottom] fractions of 7 day bone marrow cultures, Ia-negative, bone marrow nonlymphocytes were cultured in GM-CSF. At days 2 and 4, nonadherent cells were gently washed away and at day 6, the loosely attached cell aggregates were isolated by 1 g sedimentation. After a day in culture, the cells that were released from the aggregates were cytospun onto glass slides and stained with different mAbs plus peroxidase anti-Ig as well as Giemsa and nonspecific esterase. The firmly adherent cells in the original cultures were dislodged with EDTA and also cytospun. Many dendritic profiles are in the released fraction [a hand lens is useful to detect cell shape and contaminating granulocytes, in the Giemsa stain], while the adherent cells are for the most part typical vacuolated macrophages. Strong MHC class II expression occurs on all released cells but for a few typical granulocytes. Only a subset of the firmly adherent cells express class II. Most released cells express the 2A1 endocytic vacuole antigen, while the adherent cells are 2A1 weak or negative.

D. Cell surface and intracellular antigens: Cell surface staining utilized cytofluorography [FACScan; Becton Dickinson, Mountain View Calif.]. Staining with primary rat or hamster mAbs was followed by FITC-conjugated mouse anti-rat or goat anti-hamster Ig's as described in Example 1D. A panel of mAbs to cell surface (23, 24) and to intracellular antigens (33, 34) was tested on cytospin preparations. We studied both adherent and nonadherent populations, the former being dislodged in the presence of 10 mM EDTA [the adherent cells were rinsed twice with PBS and once with EDTA-PBS, and then incubated with EDTA-PBS for 20 min at 37° C.]. The cytospins were fixed in acetone and stained with mAbs followed by peroxidase conjugated anti-rat or anti-hamster Ig. The peroxidase was visualized with diaminobenzidine, and the nuclei counterstained with Giemsa.

E. Cytologic assays: Giemsa stains were performed on cytospin preparations as was the case for the nonspecific esterase [α-naphthyl acetate as substrate] stain using standard methods (35) except that the cytospin preps were fixed with 2% glutaraldehyde in Hanks medium instead of buffered acetone formalin. Phase contrast observations, usually of living cells, were made with inverted microscopes [Nikon Diaphot] at a final magnification of 100 and 400×. Transmission electron microscopy (36) and $^3$H-thymidine autoradiography were performed on developing dendritic cells as described in Example 1E.

F. Mixed leukocyte reactions: Cells from the bone marrow cultures were exposed to 15 Gy of X-ray irradiation and applied in graded doses to $3 \times 10^5$ syngeneic or allogeneic T cells in 96 well flat bottomed culture plates for 4 d. The T cells were prepared by passing spleen and lymph node suspensions through nylon wool and then depleting residual APCs with anti-Ia plus J11d mAbs plus complement. 3H-thymidine uptake was measured at 80–94 h after a pulse of 4 uCi/ml [222 GBq/mmol; American Radiolabeled Chemicals, Inc, St.Louis, Mo.].

G. Aggregates of proliferating dendritic cells from mouse bone marrow supplemented with GM-CSF.

Prior to culture, we treated the marrow suspensions with a cocktail of mAbs to B cells, T cells, and MHC class II antigens plus complement. This pretreatment of bone marrow cells which reduces the number of B cells and granulocytes, is necessary to identify growing dendritic cells in bone marrow because B cells and granulocyte are also GM-CSF responsive and proliferate and mask the presence of dendritic cell precursors.

Accordingly, at d2 and d4 of culture, we gently swirled the plates to remove loosely adherent cells which proved to be granulocytes typical in morphology and expression of the RB6 antigen [see below]. With these steps, we recognized by day 4 cellular aggregates attached to a layer of adherent cells. Some of the profiles in the aggregates had the veil or sheet-like processes of dendritic cells. The aggregates could be dislodged by gentle pipetting and separated by 1 g sedimentation. Within 3 h of replating, many spiny adherent cells emigrated from the clusters and had the appearance of fresh splenic adherent cells (13). After another day of culture, these adherent cells came off the surface and many typical dendritic cells were seen floating in the culture medium. Optimal yields of dendritic cells were obtained when the aggregates were harvested on day 6 and then cultured overnight. The capacity of bone marrow to generate dendritic cells is striking, $>5 \times 10^6$ from the 4 major hind limb bones in a week.

Attached to the surface of the culture wells were cells with the cytologic features of macrophages, and these also expanded in numbers during the first week of culture. These cells could be dislodged by pipetting after incubation at 37° C. in the presence of 10 mM EDTA.

If the cultures were maintained in M-CSF, large numbers of macrophages grew out and were firmly attached to the plastic surface. However, no dendritic cells or dendritic cell aggregates were apparent. If a mixture of M-CSF and GM-CSF was applied, then colonies of adherent macrophages as well as aggregates of growing granulocytes and dendritic cells were noted.

H. Development of potent MLR stimulator cells in bone marrow cultures

It is known that suspensions of mouse bone marrow are not active as MLR stimulators (38) and do not contain detectable dendritic cells (30). Given the cytologic observations above, we cultured Ia-negative, bone marrow non-lymphocytes for 6d and checked MLR stimulating activity at daily intervals. As long as the cultures were supplemented with GM-CSF, strong MLR stimulating activity developed [FIG. 5]. The increase was progressive and by day 6, as few as 100 of the marrow cells induced MLRs with stimulation indices of 20 or more.

To correlate the development of MLR stimulating activity with the appearance of dendritic cells in these heterogenous cultures, we first separated the cultures into nonadherent and loosely adherent fractions [FIG. 6A]. The nonadherent cells, which were mainly granulocytes in the first 4 days, were obtained by gently swirling the plates and harvesting the cells. The loosely adherent cells, which contained the aggregates of presumptive dendritic cell precursors and dendritic cells at day 4 and later times, were dislodged by pipetting over the surface of firmly adherent stromal cells. At d2 and at d4, the most potent stimulating activity was in the adherent fraction. By d6, the nonadherent fraction was very active. If one tested firmly adherent macrophages, there was no MLR stimulating activity [FIG. 6B, open squares].

As mentioned above, in the presence of GM-CSF the cultures developed aggregates of growing cells that release typical dendritic cells between d4–8 of culture. These aggregates could be isolated by gentle pipetting over the monolayer followed by 1 g sedimentation. When the aggregates were returned to culture, populations enriched in dendritic cells were released, and these released cells proved to have the very strong MLR stimulating activity that is characteristic of dendritic cells [FIG. 6B].

I. Cell surface markers—cytofluorography

By cytofluorography, two populations of cells were readily distinguished in the nonadherent or easily dislodged cells. One population had a low forward light scatter, high levels of the RB6 antigen, and low levels of MHC class II. The other population was larger and had the reciprocal phenotype. The aggregated cells were enriched relative to unfractionated cultures in MHC class II positive cells [FIG. 8, compare left and middle), and the level of MHC class II on individual cells increased when the aggregates were cultured overnight to release highly enriched populations of dendritic cells [FIG. 8, compare middle and right]. More MHC class II rich, RB6 antigen negative cells were seen in day 6 verses day 4 cultures [FIG. 8]. None of the cells reacted with the mAbs to the B220 antigen of B cells or the SER-4 antigen of macrophages [not shown].

More detailed FACS studies were performed on cells that had been released from the aggregates. The granulocytes were gated out on the basis of lower forward light scattering. The larger, dendritic cells had uniformly high levels of MHC class I and II as well as CD44 and CD11b [Mac-1; M1/70]. Intermediate level staining was noted for the heat stable antigen [HSA; M1/69], CD45 [M1/9.3], and CD18 [2E6]. Lower level staining was evident for the low affinity IL-2 receptor [CD25, 7D4], interdigitating cell antigen [NLDC-145], Fcγ receptor [2.4G2], dendritic cell antigen [33D1], macrophage antigen [F4/80], and CD11c p150/90 β2-integrin [N418]. Several antigens were not detectable including phagocyte [SER-4 marginal zone macrophage, RB6 granulocyte] and lymphocyte [RA3–6.1 B lymphocyte; thy-1, CD3,4,8 T lymphocyte] markers. This phenotype is similar in many respects to that seen in splenic and epidermal dendritic cells (24, 27, 28). The one exception is the high level in the marrow-derived cells of CD11b, an integrin that helps mediate emigration of myeloid cells from the vasculature.

J. Cytospin preparations

Cytospins were prepared to further compare the released dendritic cells with the firmly adherent stromal population. By Giemsa stain, the cells that had released from the aggregates had the typical stellate shape of dendritic cells, while the adherent cells were for the most part vacuolated macrophages. Many of the dendritic cells had a perinuclear spot of nonspecific esterase stain, while the more adherent populations had abundant cytoplasmic esterase.

The released cells stained strongly for MHC class II products, except for the contaminants with typical granulocyte nuclei. The strongly adherent cells contained a subpopulation of class II positive cells. Recently antigens have been described that are primarily localized in intracellular vacuoles of dendritic cells and B cells but not mononuclear phagocytes. The antibodies are termed M342 (34) and 2A1. Many of the dendritic cells had strong 2A1 stain, and a smaller number expressed M342. The adherent cells had a few profiles with weak 2A1.

The development of Ia-positive cells, and cells expressing granular intracellular antigens, was quantitated on cytospins. [FIG. 10]. MHC class II antigens were expressed first, followed by the 2A1 and M342 granular antigens. [FIG. 10]. By day 8, the majority of the cells were dendritic and had high levels of MHC class II products and 2A1 antigen. If granulocytes were not removed from the cultures, the yield of nonadherent cells was much larger but the highest percentage of MHC class II positive cells that we detected was 30%, and it was difficult to identify and isolate the aggregates that were the site of dendritic cell growth.

When the cytospins were stained for other myeloid antigens, the released cells stained weakly and sometimes not at all above background with monoclonals to the Fcγ receptor [2.4G2] and macrophage restricted antigen [F4/80]. Most of the firmly adherent cells in contrast stained strongly for both antigens. This suggests that while low levels of 2.4G2 and F4/80 are found on the surface of the released dendritic cells, synthesis and expression are probably being downregulated much as occurs when epidermal dendritic cells are placed in culture (27).

On day 4, some 30–50,000 Ia-positive cells were floating in the cultures, while on both day 6 and on day 8, another 50–100,000 Ia-positive cells were harvested. The quantitative data indicated that each well produced some 200,000 or more Ia-positive cells in a week. Since we obtain about 20–30 wells of the starting Ia-negative marrow cells from two tibia and two femurs, the total yield of Ia-positive cells is $5 \times 10^6$ or more, exceeding the total estimated number of Langerhans cells in the skin of a mouse (27).

K. 3H-thymidine pulse chase experiments

To further document the proliferation and differentiation of dendritic cells in these cultures, clusters of cells were isolated on day 4, exposed to a 12 h pulse of $^3$H-thymidine, and examined by autoradiography immediately or after 1, 2 and 3 days of chase in $^3$H-thymidine free medium. The majority of cells in the aggregate were labeled initially, and almost all cells released from the aggregates were labeled. During the chase, increasing percentages of the released progeny expressed the 2A1 granule antigen of mature dendritic cells.

L. Electron microscopy

The released cells had many large veils or lamellipodia extending from several directions of the cell body. The cytoplasm had many mitochondria, few electron dense granules and lysosomes, but several electron lucent vesicles some with the cytologic features of multivesicular bodies. The numerous cell processes extending from the dendritic cells were evident in the semi-thin sections of our preparations.

A bone marrow-derived dendritic cell at d5 of culture shows many cytoplasmic veils. A close up of the perinuclear region shows profiles of smooth reticulum and vacuoles. There are few lysosomal or phagocytic structures.

Example 3

Mouse Dendritic Cell Progenitors Phagocytose Particulates Sensitizing Mice to Mycobacterial Antigens In Vivo Material and Methods A. Mice: BALB/C×DBA/2 F1, C57BL/6×DBA/2 F1, and BALB/C male and female mice were purchased from the Trudeau Institute [Saranac Lake, N.Y.] and Japan SLC [Hamamatsu] and used at 6–10 weeks of age.

B. Bone marrow cultures: As described in Example 2 above, bone marrow was flushed from the femus and tibias, depleted of red cells with 0.83% ammonium chloride, and cultured in 24 well plates [Nunc, Napaville, Ill. and Corning #25820, Corning N.Y.] at $10^6$ cells/well in 1 ml of RPMI-1640 supplemented with 5% fetal calf serum, 20 ug/ml gentamicin, and 1000 U/ml of recombinant murine GM-CSF [Kiren Brewery, Maebashi, Gumma, Japan; $9.7 \times 10^7$ U/mg]. At d2, 0.75 ml of medium and the nonadherent cells were removed, and replaced with fresh medium. This was repeated at d4–5, thereby removing most of the developing granulocytes and leaving behind clusters of proliferating dendritic cells adherent to a stroma that included scattered macrophages. The culture medium was then supplemented with particulates of BCG mycobacteria [described in greater detail below], and phagocytosis was allowed to proceed for 20–24 h usually on d5–6. At this point the cultures were rinsed free of loose cells and particles, and the cells analyzed immediately for particle uptake. Alternatively cells in the washed cultures were dislodged and $3–4 \times 10^6$ cells transferred to a 60 mm Petri dish for a 1 or 2 day "chase" period in particle-free, fresh, GM-CSF supplemented medium. Class II-rich, mature dendritic cells developed during the chase as described in Example 2, and these were isolated by cell sorting [below]. To compare the phagocytic activity of developing and mature dendritic cells, particles were also administered to 7–8 d bone marrow cultures that are rich in single nonproliferating mature dendritic cells.

C. Particulates: BCG mycobacteria [Trudeau Institute, $1.5–2.5 \times 10^8$ CFU/ml; Kyowa Pharmaceutical Industries, Tokyo] were administered at approximately $10^7$ live BCG per 16 mm diameter well. Uptake was assessed following an "acid fast" stain using an auramine-rhodamine procedure that is more sensitive than Ziehl Neelsen and facilitates organism counts. Colloidal carbon [Pellikan Ink, Hannover, Germany] was added at 1:2000 dilution. The carbon was identified as a black granular stain in specimens stained with Diff-Quik$^R$ [Baxter Healthcare Corp, Miami, Fla.]. Suspensions of 2u latex particles [0.5% v/v; Seradyn, Indianapolis, Ind.] were applied to the cultures at 50 ul/well, a dose which covers the surface of the culture well with beads.

D. Isolation of mature dendritic cells by cell sorting:

As noted before in Example 2, the dendritic cells that are produced in GM-CSF stimulated bone marrow cultures express very high levels of surface MHC class II products [monoclonals B21-2, TIB 227 and M5/114, TIB 120 from the ATCC] as well as moderate levels of a dendritic cell-restricted antigen recognized by monoclonal NLDC-145. Immediately after the pulse with BCG, or after an additional 2 days of "chase" culture, the cells were stained with biotin B21-2 and FITC-streptavidin [Tago, Burlingame, Calif.]. Class II-rich cells then were sorted [FACStar Plus, Becton Dickinson, Mountainview, Calif.] and cytospun onto glass slides [Shandon Inst. Sewicky, Pa.]. The sorted cells were stained with Diff Quick® which outlines the stellate shape of dendritic cells in cytospins and allows enumeration of profiles containing perinuclear depots of internalized colloidal carbon or latex spheres. To visualize BCG, the cytospins were fixed in absolute acetone for 10 min at room temperature and stained with M5/114 anti-class II, NLDC-145 anti-dendritic cell, or RA3-6B2 anti-B220 or anti-B cell [the latter as a control] followed by POX conjugated mouse anti-rat Ig [Boehringer Mannheim, Indianapolis, Ind.] and diaminobenzidine tetraHCl [Polyscience Inc, Warrington, Pa.]. The preparations were then double labeled for acid-fast bacilli with auramine rhodamine. Virtually all the cells in the preparation were rich in NLDC-145 and MHC class II products. The number of BCG bacilli in at least 400 cells were enumerated.

E. Electron microscopy: To prove that cell-associated BCG were all internalized, the dendritic cells produced in pulse chase protocols [above] were fixed in 2.5% glutaraldehyde and processed for EM as described in Example 2.

F. Antigen presentation in vitro: Mice were primed with complete Freunds' adjuvant [CFA, SIGMA, St.Louis, Mo.; 25 ul in the fore and rear paws] or as a control, mycobacteria-free incomplete Freunds' [ICFA]. 7–14 d later, the draining lymph nodes were dissociated into a single cell suspension and depleted of APCs with mAbs to MHC class II, B220, and heat stable antigens [M5/114 anti-Ia, RA3-6B2 anti-B220, and J11d anti-HSA; TIB 120, 146, and 183 from the ATCC respectively] and rabbit complement. $3 \times 10^5$ of these APC-depleted, primed T cells were cultured in 96 well flat-bottomed microtest wells [Corning #25860] in RPMI-1640 medium supplemented with 0.5% mouse serum and 50 uM 2-mercaptoethanol. Graded doses of BCG-pulsed, bone marrow or spleen APCs were added. 1 uCi of 3H-thymidine [NEN, Boston, Mass.; 20 Ci/mmol; 4 uCi/ml] uptake was added to monitor DNA synthesis at 72–88 h. Data shown are means of triplicates in which standard errors were <15% of the mean.

G. Antigen presentation in vivo: APCs that had been pulsed with antigen in vitro were administered in vivo to unprimed C×D2 F1 mice. To prime T cells in draining lymph node, $2 \times 10^5$ dendritic cells were injected into the paws, and lymph node cells were prepared 5 d later. To prime T cells in spleen, $10^6$ cells were injected i.v., and splenocytes were prepared 5 or 10 d later. To measure T cell priming, bulk lymph node or spleen cells were cultured as above and challenged with graded doses of protein antigens, either purified protein derivative [PPD, from Statenserum Institute, Copenhagen, Denmark, or from Dr. Ichiro Toida, Research Institute for BCG in Japan, Kiyose, Tokyo] or bovine serum albumin [Sigma] and 3H-thymidine measured at 72–88 h. To characterize the proliferating cells, the populations were treated with antibodies and complement prior to measuring 3H-thymidine uptake.

H. Phagocytosis of latex particles within clusters of developing dendritic cells: pulse and pulse chase protocols When mouse bone marrow or blood is stimulated with GM-CSF, proliferating cell aggregates appear, and these give rise to large numbers of typical immunostimulatory dendritic cells. In bone marrow, which was used for the experiments described below, the proliferating aggregates are best identified by washing away the majority of nonadherent granulocytes that are also induced by GM-CSF in the cultures. At d5–6, the time point when the aggregates were first sizable [5–10 cells wide], we applied different particles over a 20–22 h period.

Following administration of 2 u latex spheres, heavy labeling was noted in scattered macrophages on the monolayer. In addition, some clear labeling occurred within the developing dendritic cell aggregates [FIG. 12A]. Aggregates that had been exposed to particles were recultured an additional 2 days. During this time, large numbers of cells were released into suspension. These primarily were mature dendritic cells with characteristic stellate shapes and high levels of MHC class II and NLDC-145 antigens. When the released cells were examined by light microscopy, many contained latex spheres and often around a clear perinuclear zone or centrosphere [FIG. 12B]. We also studied colloidal carbon uptake in a similar manner. When aggregates were pulsed with colloid and mature dendritic cells allowed to form during a chase period, some of the released cells had a centrosphere with small but clear cut carbon deposits [FIG. 12C]. In contrast, when latex or carbon was offered to mature dendritic cells, little uptake occurred [FIG. 12D].

I. BCG mycobacteria uptake by developing dendritic cells—acid fast stains

Live BCG mycobacteria were administered as the phagocytic meal over a 20–22 h period using the protocol for administering latex particles described above. Cell-associated bacilli were visualized by a sensitive fluorescent acid-fast stain. Following the 20 h pulse, the developing dendritic cell aggregates contained many organisms. To isolate the more mature dendritic cells from the cultures, the cells were resuspended and sorted those cells with high levels of MHC class II products. Immediately after the BCG pulse, about 20% of the sorted cells contained acid fast bacilli [Table 1]. The majority of MHC class II-weak cells were not studied further because of excessive stickiness during cell sorting.

Companion cell cultures were then studied after 2 days of a chase culture. Because many mature dendritic cells formed during the chase period, the number of Ia-rich progeny had increased four fold [Table 1].

TABLE 1

Frequency of dendritic cells with phagocytosed BCG organisms in GM-CSF stimulated mouse bone marrow cultures

| Exp't # | BCG exposure | # cells counted | % phagocytic | #BCG/DC |
|---|---|---|---|---|
| 1 | d5–6 pulse | 469 | 18.1 | 2.6 |
|  |  | 498 | 18.5 | 2.5 |
| 2 | d5–6 pulse | 444 | 22.5 | 3.0 |
|  |  | 463 | 22.2 | 2.9 |
|  | pulse, 2d chase | 564 | 57.1 | 3.8 |
|  |  | 579 | 57.0 | 3.2 |
| 3 | d5–6 pulse | 440 | 21.8 | 2.1 |
|  |  | 623 | 22.8 | 2.9 |
|  | pulse, 2d chase | 197 | 50.3 | 2.9 |
|  |  | 511 | 58.7 | 4. |

Quantitative data of dendritic cells containing BCG. Mouse bone marrow cultures were stimulated in 16 mm wells for 5 d with GM-CSF, washed, and exposed to BCG organisms for 20 h. The cultures were washed again and either examined immediately, or pooled and transferred to a 60 mm dish for an additional 2 d chase culture. The dendritic cells in the cultures were selected as Ia-rich cells using a fluorescent activated cell sorter and then cytospun onto glass slides for staining for acid fast bacilli. During the chase period, the percentage of Ia-rich cells in the cultures increased 2–2.5 fold, and the total number of cells increased 2 fold, resulting in a 4–5 fold increase in the number of Ia-rich cells.

The percentage of dendritic cells containing BCG also rose to 50% [Table 1, FIG. 13]. Double labeling experiments verified that cells with acid fast bacilli expressed MHC class II and the dendritic cell-restricted NLDC 145 antigen FIG. 13. Because the total number of MHC class II and NLDC-145 positive cells had increased 4-fold in just 2 d, it is likely that these BCG-laden dendritic cells were derived from less mature but phagocytic progenitors in the aggregates.

J. Electron microscopy of BCG pulsed APCs

The perinuclear location of the cell-associated particles by light microscopy indicated that organisms had been internalized. The matter was verified by electron microscopy. About 50% of the dendritic cell profiles contained internalized BCG, although the number of organisms per profile was small, usually one but only up to four, FIGS. 14 A, B. Each organism seemed to occupy its own vacuole. It appeared that a phagosomal membrane closely approximated most bacilli, FIGS. 14 C,D.

K. Presentation in vitro of mycobacterial antigens to primed T cells

To test the presenting function of dendritic cells that had been pulsed or pulse-chased with BCG organisms, we first prepared antigen-responsive T cells from the draining lymph nodes of mice that had been injected with CFA [complete Freund's adjuvant, which contains heat-killed mycobacteria] or with incomplete Freund's adjuvant [IFA as control; see Methods]. When dendritic cells were added to IFA-primed T cells, a syngeneic mixed leukocyte reaction was observed. This was comparable whether or not the APCs had been exposed to BCG. [FIG. 15, right]. However, when dendritic cells had been pulsed with BCG and added to CFA-primed T cells, strong proliferative responses were induced [FIG. 15, left]. If dendritic cells were tested immediately after the one day pulse, or after an additional 2 day chase period, the chased population was much more potent. [FIG. 15, left; compare ♦ and ▲]. As few as 100 BCG pulse-chased, dendritic cells elicited sizable T cell responses in vitro [FIG. 15, left ♦]. The BCG pulse-chased populations also were 5–10 times more potent in inducing responsiveness to mycobacterial antigen than mature dendritic cells freshly exposed to either PPD or BCG. [FIG. 15 left, compare ● with ▼, ▼]. Therefore, it appeared that the extent of phagocytosis correlated with the efficacy of presentation, as the pulse chased populations were the most active APCs and contained the most intracellular BCG. [Table 1].

L. Presentation in vivo of mycobacterial antigens to unsensitized mice

Comparable populations of BCG-pulsed, and BCG-pulsed and chased, APCs were tested for the capacity to present mycobacterial antigens to unprimed mice. Following injection into the footpads, strong responsiveness to PPD was observed. [FIG. 16]. Again the dendritic cells were the most potent if tested after a 2 d chase [FIG. 16; compare ◇ and △], and this chase period greatly increased the total yield of dendritic cells.

To test if the increased antigen presenting function of BCG pulse-chased dendritic cells was related to the increased number of APCs carrying BCG, the primed populations were also tested for responsiveness to bovine serum albumin [BSA], since the dendritic cells had been grown in the presence of fetal calf serum. All the dendritic cell populations, regardless of the details of the exposure to BCG, primed mice similarly to BSA. [FIG. 16, filled symbols]. This indicates that each population was comparably efficient in immunizing to a soluble protein, whereas the dendritic cells that had phagocytosed BCG were more effective in eliciting responses to mycobacterial antigens.

The surface markers of the primed cells were tested by antibody and complement mediated lysis of the populations prior to measuring 3H-thymidine uptake [data not shown]. The proliferating cells were positive for thy-1, but negative for MHC class II, heat stable antigen, and B220. Anti-CD4 hybridoma culture supernatant blocked proliferation more than 85% i.e., the primed cells were helper-type T cells.

Priming was also observed when spleen T cells were tested after an intravenous infusion of BCG-pulsed and BCG-pulse chased dendritic cells [FIG. 17]. The cells were more responsive at 5 versus 10 days after injection [compare FIGS. 17A and C]. Again dendritic cells that had been cultured ["chased"] for 2 days after exposure to BCG were the most potent [FIG. 12 compare ♦ with ▼; but all populations primed the spleen cells similarly to BSA [FIG. 17B]. We conclude that dendritic cell progenitors capture and retain mycobacterial antigens in a manner that is highly immunogenic in vivo.

Example 4

Antigen Activated Dendritic Cells as Immunogens.

Dendritic cells prepared according to the method described in Example 1 are plated at a concentration of approximately $1 \times 10^5$ cells per well of a 24 well plastic culture plate. The cells are incubated in RPMI 1640 containing 5% fetal calf serum and GM-CSF (30 u/ml). Antigen is added to the dendritic cell cultures and the cultures are incubated with antigen for approximately 4 hours or for sufficient time to allow the dendritic cells to handle the antigen in an immunologically relevant form, or in a form that can be recognized by T cells. Such handling of the antigen by the dendritic cells involves the dendritic cells 1) acquiring, 2) processing, and 3) presenting the antigen to the T cells in a form which is recognized by the T cells. Following binding of the antigen to the dendritic cells the cells are collected from the culture and used to immunize syngeneic mice. The activated dendritic cells are injected subcutaneously into the mice in an amount sufficient to induce an immune response to the antigen.

Example 5

Dendritic Cell Modified Antigen

Dendritic cells prepared as described in Example 1 are pulsed with a protein antigen for a time sufficient to allow the dendritic cells to acquire, process and present the modified antigen on the surface of the dendritic cells. The dendritic cells are then collected from the culture for extraction of the modified antigen.

For extraction of the modified antigen, the dendritic cells are solubilized with detergent to extract the modified antigen bound to MHC molecules. The MHC molecules bound to modified antigen are purified by precipitation with antibodies which bind the MHC molecules such as MH2. The modified antigens are extracted from the precipitate for analysis.

Example 6

Preparation of Dendritic Cells from Human Blood

A. Patients

Seventeen experiments were performed with blood from human patients undergoing consolidation chemotherapy (15 with leukemias/lymphomas in full remission, 2 with solid tumors) followed by treatment with G-CSF. Three experiments were performed with blood from patients after chemotherapy (1 (acute myeloic) leukemia, 2 solid tumors) and GM-CSF treatment. The results of three experiments, two from the G-CSF treated group of patients, A and B, and one from the GM-CSF treated group of patients, C, are presented.

B. Rationale

Results of procedures described in Example 1 relating to mouse blood and Example 2 relating to bone marrow (*J. Exp. Med.* 175:1157–1167, 1992 and *J. Exp. Med.* 176:1693–1702, 1992), identified several features of dendritic cell growth and development: (a) dendritic cell progenitors do not express the MHC class II antigens that are typical of mature immunostimulatory progeny and of many other cell types (B cells, monocytes); (b) dendritic cell progenitors require GM-CSF and perhaps other cytokines that can be provided by the cells in culture or as supplements to proliferate and mature; (c) critical steps in dendritic cell growth and development take place in distinctive aggregates that are loosely adherent to standard tissue culture surfaces; (d) by monitoring the appearance of these aggregates, one can evaluate the numerous variables that are pertinent to the generation of dendritic cells, a trace but specialized type of antigen presenting cell that operates in a potent fashion to induce T cell immunity and tolerance in situ (Ann.Rev.Immunol. 9:271–296, 1991).

C. Protocol

1. Blood mononuclear cells were isolated by sedimentation in standard dense media, here Lymphoprep (Nycomed, Oslo).

2. The isolated mononuclear cells were depleted of cells that were not dendritic cell progenitors. These contaminants were coated with monoclonal antibodies to CD3 and HLA-DR antigens and depleted on petri dishes coated with affinity-purified, goat anti-mouse IgG ("panning").

3. $10^6$ cells in 1 ml of culture medium were plated in 16 mm diameter plastic culture wells (Costar, Rochester, N.Y.). The medium was RPMI-1640 supplemented with 50 uM 2-mercaptoethanol, 10 mM glutamine, 50 ug/ml gentamicin, 5% serum from cord blood (without heat inactivation) or 5% fetal calf serum (with inactivation), and 400 U/ml human recombinant GM-CSF. Every 2nd day thereafter and for a total of 16 days, the cultures were fed by removing 0.3 ml of the medium and replacing this with 0.5 ml of fresh medium supplemented with the cytokines.

Cells were cultured under the following conditions: 1) without presence of additional cytokines; 2) GM-CSF, 400 or 800 U/ml; 3) GM-CSF, 400 or 800 U/ml, plus IL-1α, 50 LAF units/ml for the last 24 h of culture; 4) GM-CSF, 400 or 800 U/ml, plus TNFα 50 U/ml; 5) GM-CSF, 400 or 800 U/ml, plus TNF-α, 50 U/ml, plus IL-1α, 50 LAF units/ml for the last 24 h of culture; 6) GM-CSF, 400 or 800 U/ml, plus IL-3, 100 U/ml; 7) GM-CSF, 400 or 800 U/ml, plus IL-3, 100 U/ml, plus IL-1α, 50 LAF units/ml for the last 24 h.

In experiment C, non-dendritic cells which sank in dense metrizamide were also tested.

4. Characteristic proliferating dendritic cell aggregates (hereafter termed "balls") appeared by the 5th day, as evident upon examination with an inverted phase contrast microscope. These balls expanded in size over the course of a week (day 5–11). Some balls appeared in the original wells (steps 3 and 4), but typically these did not enlarge to the same extent as the nonadherent wells (step 4). The wells must be subcultured, e.g., 1 well split into 2–3 wells, as cell density increases.

5. Two alternative approaches were used to isolate the mature dendritic cells from the growing cultures. One method consisted of removing cells that were nonadherent and separate the balls from nonballs by 1 g sedimentation. Dendritic cells were then released in large numbers from the balls over an additional 1–2 days of culture, and mature dendritic cells were isolated from the nonballs by floatation on dense metrizamide as described (Freudenthal and Steinman, Proc. Natl. Acad. Sci. USA 87:7698–7702, 1990). The second method is simpler but essentially terminates the growth phase of the procedure. According to the second procedure, the nonadherent cells were harvested when the balls were very large. The cells were left on ice for 20 minutes, resuspended vigorously with a pipette to disaggregate the balls, and the mature dendritic cells were floated on metrizamide columns.

6. To demonstrate the immunostimulatory activity of the dendritic cell progeny, graded doses of irradiated cells (30 to 30,000 in serial 3 fold dilutions) were added to accessory cell-depleted T cells (200,000 for the mixed leukocyte reaction assay, MLR; 150,000 for the oxidative mitogenesis assay, OXMI). The T cell response was measured with a 16 h pulse of 3H-thymidine on the 5th (MLR) or 2nd day (OXMI). T cell-stimulation experiments (oxidative mitogenesis and mixed leukocyte reaction) were performed in the presence of 1 microgram/ml indomethacin. Data from three MLR experiments are presented in FIGS. 18A, B, and C.

D. Results

1. GM-CSF is an essential cytokine. G-CSF, M-CSF, IL-3, or no cytokine do not permit the development of dendritic cell balls. GM-CSF at 400–800 U/ml is optimal, irregardless of whether donors had been treated with either GM-CSF or G-CSF to expand the number of myeloid progenitor cells in blood. Addition of TNFα at 10–50 U/ml usually but not always increased dendritic cell yields up to two-fold (cf. Caux et al., (1990) Tumor necrosis factor alpha strongly potentiates interleukin-3 and granulocyte-macrophage colony-stimulating factor-induced proliferation of human hematopoietic CD34+ progenitor cells, Blood 2292–2298). As evident from the representative experiments described in FIGS. 18A, B and C, TNFA supplementation also substantially improves the function of the dendritic cell progeny. rhu IL-1α (50 LAF units/ml) in some experiments proves a further increase in function, when added during the last 24 h of the culture. Experiments with tissue from patients with solid tumors or leukemias/lymphomas gave comparable results with regard to the generation of dendritic cells.

2. Starting from 60 ml of blood, and after culturing in the presence of GM-CSF only, the yield of typical mature immunostimulatory dendritic cells was 6–12×$10^6$ cells, representing 40–80% of the total cells. This yield is at least 20 times greater than the yield of mature dendritic cells in 60 ml of fresh blood which would be at most 5% (3–6×$10^5$) of this (Proc. Natl. Acad.Sci. 87:7698–7702, 1990).

3. The phenotype of the dendritic cells generated by this method included the fact that the cells were strongly positive for HLA-DR, MHC class II products but negative for CD1a, CD14, and B cell markers.

4. The development of granulocytes in the cultures reduces the purity of the dendritic cells. Typically, these granulocyte balls are more adherent and are left behind at the day 2 transfer step of the protocol. If these adherent granulocyte colonies reappear, simply transfer the growing dendritic cells may be transferred to another well.

Example 7

Other sources of dendritic cell progenitors have been tested according to the method described in Example 6:

a) For two patients, a small sample of bone marrow was also provided. When the above procedure was applied, the dendritic cell balls and mature immunostimulatory dendritic cells were formed in large numbers.

b) Blood from 7 normal donors has been evaluated using the method described in Example 6. The number of balls proved to be much less (10–20/well of 2×$10^6$ cells), but the use of normal blood is obviously simpler and has the advantage that granulocyte colonies do not form as noted before (comment 5) in comparing mouse blood and marrow, J.Exp. Med. 175:1157–1167, 1992 vs. J.Exp. Med. 176:1693–1702, 1992).

c) Fetal or umbilical cord blood was also tested, because it too contains more progenitor cells than adult blood. Since the number of CD34+ progenitors is still very small (about 1%), we tested the simpler method above in which CD34+ cells are not purified initially. DC balls are readily induced, except that red blood cells which are toxic were depleted. By adding the anti-erythroid monoclonal VIE-G4 (provided by Dr. W. Knapp, Vienna) to the panning step (step 2), and using an additional floatation on Lymphoprep (step 1) after panning. The yields of dendritic cells from cord blood are roughly comparable to that described in the method (1–5× $10^6$ dendritic cells, representing 20–40% of the total cells from 40 ml cord blood without a metrizamide floatation step). The balls are more adherent, and the dendritic cells express CD1a, in contrast to adult blood.

Example 8

Generation of Large Numbers of Dendritic Cells From Human Blood Cultures Supplemented with GM-CSF and IL-4

Materials

A. Culture medium: was RPMI 1640 supplemented with 200 mM L-glutamine, 50 mM 2-ME, 20 mg/ml gentamicin, and either 5–10% FCS [56° C., 0.5 h; Seromed, Biochrom KG, Berlin, Germany), or, in some experiments with 5% cord blood serum.

B. Recombinant human cytokines: GM-CSF (3.1×$10^6$ U/mg) was kindly provided by Dr. E. Liehl (Sandoz Research Institute, Vienna, Austria), TNFa (6×$10^7$ U/mg) by Dr. G. R. Adolf (Ernst Boehringer Institut fur Arzneimittelforschung, Vienna, Austria), and IL-1a [3×$10^8$ U (D10 assay)/mg] by Dr. P. Lomedico (Hoffmann La Roche Inc., Nutley, N.J., USA). IL-4 was commercially obtained material (1×$10^7$U/mg) (Genzyme Co., Boston, Mass.) or supernatant from IL-4 gene transfected COS cells (3×$10^4$ U/ml) kindly provided by Dr. G. Le Gros (Ciba-Geigy Ltd., Basel, Switzerland). M-CSF (1.9×$10^6$ U/mg) was a gift of Dr. S. Clark, Genetics Institute, Cambridge, Mass. IL-3 and G-CSF were purchased from Genzyme Co.

C. Monoclonal Antibodies: We used the following mouse mAb's (referenced in Lenz, et al., (1993) J. Clin. Invest. 92:2587 unless defined here): W6/32, anti-HLA-A,B,C (HB95 from the ATCC); L243, anti-HLA-DR (Becton-Dickinson [BD], Mountain View, Calif.); 9.3F10, anti-HLA-DR+DQ (HB180 from ATCC); RFD1, anti-HLA-DQ-related (gift of L. W. Poulter, London, England); B7/21, anti-HLA-DP (BD); UCHL-1, anti-CD45RO (Dako Corp., Glostrup, Denmark); 4G10, anti-CD45RA; 3C10 and LeuM3 (BD), anti-CD14; EBM11, anti-CD68 (Dako); LeuM1, anti-CD15 (BD); LeuM9, anti-CD33 (BD); HPCA- 1, anti-CD34 (BD); Leu11b, anti-CD16 (BD); 2A3, anti-CD25 (BD); IV.3 (C. L. Anderson, Columbus, Ohio.) and CIKM5 (G. Pilkington, Melbourne, Australia), anti-FcgRII/CD32; 15–1, anti-FceRI (J.-P. Kinet, Rockville, Md., Wang, et al, (1992) *J. Exp. Med.*, 175:1353; OKT-6, anti-CD1a (Ortho Pharmaceuticals, Raritan, N.J.); Leu4 (BD) and OKT-3 (Ortho), anti-CD3; Leu3a+b, anti-CD4 (BD); Leu1, anti-CD5 (BD); Leu2a, anti-CD8 (BD); Leu12, anti-CD19 (BD); Leu16, anti-CD20 (BD); VIB-E3, anti-CD24 (W. Knapp, Vienna, Austria); G28-5, anti-CD40 (J. A. Ledbetter, Seattle, Wash.); TB133, anti-LFA-1/CD11a and CLB54, anti-CD18 (both from S. T. Pals, Amsterdam, The Netherlands); LeuM5, anti-CD11c (BD); 7F7, anti-ICAM-1/CD54 (M. P. Dierich, Innsbruck, Austria); AICD58, anti-LFA-3/CD58 (Immunotech, Marseille, France); BB1, anti-B7/BB1/CD80 (E. A. Clark, Seattle, Wash.); Lag, anti-Birbeck-granule-associated (M. Kashihara-Sawami, Kyoto, Japan Kashihara, et al., (1986) *J. Invest. Dermatol.*, 87:602); VIE-G4, anti-glycophorin (O. Majdic, Vienna, Austria); Ki-67, proliferation-associated antigen (Dako, Gerdes, et al., (1984) *J. Immunol.*, 133:1710).

D. Culture of DC from cord blood: Cord blood was collected according to institutional guidelines during normal full-term deliveries. PBMC (peripheral blood mononuclear cells) were isolated by flotation on Lymphoprep (Nycomed, Oslo, Norway), washed, incubated once in saturating concentrations of anti-glycophorin mAb, anti HLA-DR and anti CD3, washed, panned (10 min. on ice, then 20 min. at RT) twice onto bacterial petridishes coated with goat anti-mouse Ig (H+L) Ab (Jackson Lab., Avondale, Pa.). The nonadherent fractions were then plated in 24-well dishes (Costar, Cambridge, Mass., USA) and cultured as described in detail in Results.

E. Culture of DC from blood of cancer patients: Peripheral blood was obtained with informed consent from cancer patients in complete remission during hematopoietic recovery following high-dose consolidation chemotherapy and administration of G-CSF [300 μg rG-CSF (Neupogen, Hoffmann-La-Roche Ltd.) s.c. /d] (15 patients with leukemias/lymphomas, 2 with solid tumors) or GM-CSF [400 μg (Leukomax, Sandoz Ges m.b.H) s.c./d] (1 patient with leukemia, 2 with solid tumors]. PBMC were prepared by sedimentation in Lymphoprep, coated with anti HLA-DR+anti CD3 mAb's, washed, and panned twice as described above. Non-adherent, depleted fractions were then processed according to the protocol described in detail in Results.

F. Culture of DC from blood of healthy adults: PBMC were obtained from either 40 to 100 ml heparinized fresh whole blood or leukocyte-enriched buffy coats (Freudenthal, P. S. and R. M. Steinman (1990) *Proc. Natl. Acad. Sci.* USA 87:698, and processed as described in detail in Results.

G. Phenotypic analysis: Phenotypic analysis was performed exactly as described previously in Romani, et al., (1989) *J. Invest. Dermatol.*, 93:600 by immunolabeling and flow cytometry analysis, and by immunoperoxidase/-fluorescence on cells cytospun or attached by poly-L-lysine to glass slides.

H. T cell stimulation assays: Allogeneic 1 MLR (mixed luihexyte reaction) and oxidative mitogenesis were performed exactly as described in Romani, et al., (1989) *J. Invest. Dermatol.*, 93:600.

I. Cord blood mononuclear cells as a source for DC progenitors: Three different situations to generate DCs from proliferating progenitors or precursors in blood were evaluated. Our goals were to define requisite criteria and cytokines for proliferating DCs, but at the same time to avoid the need to enrich for CD34+ progenitor populations which are so few in number. We began with cord blood, since a prior report had shown that $0.5-1\times10^6$ enriched [>95%]CD34+ cord blood cells could give rise to $1-2.5\times10^7$ DCs if cultured for 14 days in a combination of GM-CSF and TNF (Caux, et al., (1992) *Nature*, 360:258). A limitation to this previous protocol was that cord blood only contains 0.9–2.6% CD34+ cells (Mayani, et al., (1993) *Blood*,81:3252). Therefore we modified the technique described above used with adult mouse blood (Example 1), in which un-fractionated cells, or MHC class II negative cells, were cultured in GM-CSF. We found that the varying, yet substantial percentage of nucleated erythroid cells in human cord blood was toxic and that these could be removed by panning with anti-glycophorin A mAb. We began, then with erythroid-depleted cord blood cells with a low buoyant density [<1.077 g/ml] and plated these at $1-2\times10^6$/ml in 1 ml of standard medium supplemented with GM-CSF [400–800 U/ml]+/– TNF [50 U/ml]. The wells were fed every other day by aspirating 0.3 ml medium and adding back 0.5 ml medium with cytokines.

The subsequent events were similar to those described previously with mouse blood. First, small adherent aggregates appeared after 4–7 d [FIG. 19A and FIG. 19B]. Many of the peripheral cells displayed a veiled or dendritic appearance, and these adhered loosely to a nest of spindle-shaped cells. Nonadherent cells could be removed by carefully rinsing in warm medium, but this was not essential. The adherent aggregates enlarged over the next 7–10 d, indicating proliferative activity [FIG. 19C]. Then typical "veiled" DCs [FIG. 19D–FIG. 19E] were released. These DC aggregates only developed if GM-CSF was added to the medium. TNF-α although not essential, increased aggregate size and DC yield 50–100%. It was advantageous to remove the TNF-α during the last 1–2 d of culture to permit the release of single, mature DCs.

The released DCs were identified by three sets of criteria. First, the cells by inverted phase contrast microscopy showed characteristic thin motile cytoplasmic processes or veils [FIG. 19D–FIG. 19E]. By EM, the typical ultrastructure of DCs was noted [see below, FIG. 24]. Only one Langerhans cell granule (=Birbeck granule) was found in 100 cell profiles. Second, the DCs had the standard phenotype i.e., HLA-DR rich but negative for markers of other cells e.g., CD3/14/19/20. Like epidermal Langerhans cells, CD1a was detected but only 1–2% of the cells reacted with an antigen associated with Langerhans cell granules [anti-Lag] (Kashihara, et al., (1986) *J. Invest. Dermatol.*, 87:602), and these interestingly were in the center of rare residual aggregates. Third, the cord blood derived DCs were potent stimulators of resting T cells in the primary MLR [FIG. 20A] as well as oxidative mitogenesis [not shown]. The inclusion of TNF in the culture medium increased the immunostimulatory function of the DCs [FIG. 20A].

The above protocol has proven reproducible in 21 standardized experiments and generates $1-5\times10^6$ DCs from 40 ml of cord blood at a purity of 20–50% (Table II). Purity can be increased to >80% by flotation on metrizamide (Freudenthal, P. S. and R. M. Steinman, (1990) *Proc. Natl. Acad. Sci. USA*, 87:7698) columns. We conclude (a) it is not necessary to enrich for CD34+ precursors to generate typical DCs from cord blood, and (b) the criteria that proved useful in identifying aggregates of proliferating progenitors in mouse blood are also applicable to human cells.

J. DC progenitors in the blood of cancer patients during hematopoietic recovery from chemotherapy: We next studied blood mononuclear cells from cancer patients in full remission [leukemias/lymphomas and solid tumors] following high-dose chemotherapy and either G-CSF [17 patients] or GM-CSF [3 patients] treatment. It is known that in the hematopoietic recovery of such patients, progenitors are mobilized into the blood in substantial numbers [0.5–6.0% CD34+ cells] (Eaves, C. J. (1993) *Blood*, 82:1957; Pettengell, et al., (1993) *Blood*, 82:3770). Instead of enriching for CD34+ cells, we simply removed CD3+ and DR+ cells by panning, and then plated 1–2×10$^6$cells in 1 ml medium with 5–10% FCS or 5% cord serum plus 400–800 U/ml GM-CSF. The nonadherent cells were transferred at d2 (or in some experiments at d1) and cultured for 16 d feeding every other day.

Growing DC aggregates appeared on day 3–5 and expanded in size until day 11 [not shown, but compare FIG. 21]. The aggregates developed peripheral veils, and initially were loosely attached to a stroma but later were nonadherent. The wells were subcultured e.g., 1 well split to 2–3 wells, when the cell density increased or if more tightly adherent, smooth, non-DC clusters appeared [contaminating macrophage and granulocyte progenitors]. When the DC aggregates became very large (d12–d16), it was easy to dissociate the cells and float the mature DCs on metrizamide columns.

The DCs that developed in this manner had a typical morphology by light and electron microscopy [not shown, but see FIGS. 21 and 24]. The phenotype was again MHC class II rich but null for CD3/14/19/20 [not shown]. MLR stimulatory function was potent [FIG. 20B]. In contrast to cord blood derived DCs, CD1a and Lag antigens were not seen (not shown).

GM-CSF proved essential for DC development. G-CSF, M-CSF and IL-3 were inactive. Exposure to 3000 rads of ionizing irradiation blocked DC development. Addition of TNF-α at 10–50 U/ml usually though not always increased DC yields up to 2 fold, and always improved the function of DCs [FIG. 20B]. Human rIL-1 [50 LAF unit/ml], when added during the last 24 h in some experiments, further increased function [FIG. 20B].

Starting from 40 ml blood, and using both GM-CSF and TNF-α, the yield (Table II) of mature DCs was 4–8×10$^6$ at 16 d with 60–80% purity. This is at least 20 times the yield of mature DCs in fresh normal blood (Freudenthal, P. S. and R. M. Steinman, (1990) *Proc. Natl. Acad. Sci. USA*, 87:7698; O'Doherty, et al. (1993) *J. Exp. Med.*, 178:1067).

TABLE II

DC Progenitors in Human Blood

| Type of Blood Donor | Enrichment of DC Progenitors | Time of Culture | DC Yields/ 40 ml Blood | DC Enrichment | Cytokines Added |
|---|---|---|---|---|---|
| Neonatal, cord blood | Remove glycophorin$^+$ erythroid cells | 10–20 d | 1-5 × 10$^6$ | 20–50% | GM-CSF TNFα |
| Adult blood, patients & chemotherapy & CSF therapy | Remove CD3$^+$ & HLA-DR$^+$ cells | 16 d | 4-8 × 10$^6$ | 60–80% | GM-CSF TNFα |
| Adult blood, normal | Bulk PBMC, adherent & loosely adherent | 5–7 d | 3-8 × 10$^6$ | 40–80% | GM-CSF IL-4 |

K. Proliferating DC aggregates from normal adult blood: When we applied the above methods to blood from healthy adults, we did observe some small, adherent, veiled aggregates between d8–16. In all 20 experiments, the aggregates then deteriorated and did not enlarge, leaving behind nonviable cells or less often a few macrophages. Because a stromal monolayer was not evident in the cultures, we next omitted the panning step with anti-CD3 and HLA-DR in case the panning antibodies removed required accessory cells. We simply plated 10$^6$ bulk mononuclear cells in 1 ml of medium with GM-CSF [800 U/ml] and TNF-α [50 U/ml], and after 1 day gently removed the nonadherent lymphocytes. We then observed the adherent cells every 12 h under the inverted microscope. To our surprise, many small adherent aggregates developed within 2 d, and most were covered with typical DC veils. However within 2 more days, the aggregated cells became round and gave rise to a monolayer of macrophages. These events took place whether GM-CSF, or GM-CSF plus TNF-α were added. However by d12–16 typical expanding DC aggregates appeared in some of the wells. These aggregates were loosely affixed to an adherent monolayer similar as previously observed in mouse blood (Inaba, et al., (1992) *J. Exp. Med.*, 175:1157) [not shown]. The DCs that were released were typical in morphology, phenotype [not shown], and T cell stimulatory function [FIG. 20C]. The yield was about 4% of the initial number of mononuclear cells plated, which is far greater than the 0.5–1% yield of DCs in fresh blood (Freudenthal, P. S. and R. M. Steinman, (1990) *Proc. Natl. Acad. Sci. USA*, 87:7698; O'Doherty, et al. (1993) *J. Exp. Med.*, 178:1067).

Not wishing to be bound by theory, we suspect from these findings that DC precursors were actually quite numerous in blood, but that the precursor still had the potential to give rise to macrophages. The latter is known to be the case for the colony forming units that GM-CSF induces in mouse (Inaba, et al., (1993) *Proc. Natl. Acad. Sci. USA*, 90:3038). Since IL-4 at 500–1000 U/ml blocks macrophage colony formation (Jansen, et al., (1989) *J. Exp. Med.*, 170:577), we added IL-4 to GM-CSF and repeated the experiments.

The combination of GM-CSF and IL-4 produced two striking findings. First the numerous, initial veiled aggregates [FIG. 21A$a$] did not transform into macrophages but rather increased rapidly in size over the next few days [FIG. 21B]. The aggregates became nonadherent, displayed typical veils all over the periphery, and began to release mature DCs [FIG. 21C]. Second, the single adherent cells [presumably monocytes] that were scattered in between the small adherent aggregates, also became nonadherent and developed processes similar to those of typical DCs [not shown]. Growing DC aggregates only formed in the presence of both GM-CSF and IL-4. The initial nonadherent fraction also developed some aggregates but these were obscured by the excess of lymphocytes.

After having made these observations in 20 experiments, we found it simpler to use larger 35 mm wells. The protocol was to plate 5–20×10$^6$plain bulk mononuclear cells in 3 ml of medium, to discard the nonadherent cells at 2 h with a very gentle rinse, and then to culture the adherent cells in medium supplemented with GM-CSF (800 U/mll and IL-4 [500 U/ml]. With the above gentle wash, the nonadherent cells did not develop DC aggregates, but with more vigorous washing, the aggregates mainly developed in the nonadherent fraction.

The presumptive DC aggregates were verified to be proliferating by two criteria: staining of ~10% of the cells with the Ki-67 mAb that identifies an antigen in cycling cells (Gerdes, et al., (1984) *J. Immunol.*, 133:1710) [FIG. 22D], and sensitivity to 3000 rads. In contrast the tightly adherent populations, which could develop single cells with the appearance of DCs [see above], were nonproliferating as evidenced by a lack of staining with anti-Ki 67 mAb [FIG. 22D] and a resistance to 3000 rads of irradiation.

The combination of GM-CSF and IL-4 reproducibly gives rise to large growing DC aggregates over a 5–7 d period. At that time, growth essentially ceased. The aggregates then could be disassembled by pipetting into DCs with characteristic morphology at the light [FIG. 21C] and EM level [FIG. 24], a typical surface phenotype [FIG. 23], and strong T cell stimulatory function [FIG. 20D–20F]. Human rIL-1 [50 LAF units/ml], when added during the last 24 h of culture, amplified the stimulatory function of DCs similar as observed with murine DCs isolated from spleen or epidermis (Heufler, et al., (1988) *J. Exp. Med.*, 167:700; Koide, et al., (1987) *J. Exp. Med.*, 165:515). Interestingly the blood-derived DCs expressed CD1a, CD4, and FceRI as is typical of epidermal Langerhans cells (Wang, et al., (1992) J. Exp. Med., 175:1353; Romani, N., P., Fritsch, and G. Schuler. (1991). "Identification and phenotype of epidermal Langerhans cells." In Epdermal Langerhans Cells. G. Schuler, editor. CRC Press, Boca Raton. 49–86; Bieber, et al., (1992) *J. Exp. Med.*, 175:1285). Birbeck granules were not detectable by EM however, and only a rare cell in the center of a residual DC aggregate stained with anti-Lag mAb (Kashihara, et al., (1986) *J. Invest. Dermatol.*, 87:602) [FIG. 22C]. Anti-CD68 immunostaining revealed a perinuclear zone of reactivity in some of the DCs [FIG. 22A], a feature that differs from the strong diffuse granular staining of macrophages [FIG. 22B].

The yield of mature, immunostimulatory DCs (Table II) was 6–15% of the mononuclear cells plated. This is many times greater than the number of DCs that can be identified in unstimulated blood [0.3–1%] (Freudenthal, P. S. and R. M. steinman, (1990) *Proc. Natl. Acad. Sci. USA*, 87:7698; O'Doherty, et al. (1993) *J. Exp. Med.*, 178:1067). The above protocol and yield [3–8×10$^6$ DCs/40 ml of blood] has proven reproducible in over 25 experiments with blood from healthy males and females [25–60 yrs], using either fresh venapuncture or buffy coat preparations.

DC Progenitors in Human Blood—Identification:

These findings of necessity appear methodological in nature but in fact outline a pathway whereby the distinct DC lineage can be induced to proliferate and mature from precursors that are relatively plentiful in human blood. The methodological caste of our results reflects the difficulty inherent in identifying precursors and progeny in this distinctive immunostimulatory pathway. DCs are not yet known to express a lineage-specific surface antigen, as is the case with lymphocytes, e.g., CD3, CD19, CD20. A lack of lineage specific markers is also typical of the individual human myeloid lineages e.g., monocytes, neutrophils, basophils, eosinophils. However, these other myeloid lineages have distinctive tinctorial properties and distinctive CSF's e.g., M-CSF and G-CSF. DCs in contrast are only known to respond to the multilineage cytokine GM-CSF (Witmer-Pack, et al., (1987) *J. Exp. Med.*, 166:1484; Heufler, et al., (1988) *J. Exp. Med.*, 167:700; Koch, et al., (1990) *J. Exp. Med.*, 171:159), and their peculiar morphology, phenotype and function is best outlined with a composite of approaches (Steinman, et al. *Annu. Rev. Immunol*, 9:271.

Given these inherent difficulties, we searched for criteria that were similar to those that had been used to identify immature DC progenitors [e.g., MHC class II negative] in mouse blood (Inaba, et al., (1992) *J. Exp. Med.*, 175:1157) and bone marrow (Inaba, et al., (1992) *J. Exp. Med.*, 176:1693). Mouse DCs proliferate within a characteristic aggregate that attaches loosely to an underlying stroma and is covered with large sheet-like processes or veils [compare FIGS. 19, 21]. By defining conditions that give rise to such aggregates, at first containing a few cells but growing to >10 cells in diameter, we could establish that proliferating DC progenitors are readily detectable in the blood of all healthy adults, and that one could use these progenitors to generate relatively large numbers of typical immunostimulatory DCs within 7 days, i.e. 3–8 million of such cells/40 ml of blood.

Like cells derived from mouse blood, the critical finding regarding human blood, including blood from normal individuals, is the requirement for GM-CSF. Cells from normal human blood in the presence of GM-CSF alone were capable of supporting dendritic cell precursors but formed significantly fewer large aggregates compared to cells from mouse blood. However, human blood contained significantly larger numbers of macrophages. IL-4, a known inhibitor of macrophage colony formation (Jansen, et al., (1989) *J. Exp. Med.*, 170:577), allowed extensive DC growth and maturation to ensue [FIG. 21].

DC Progenitors in Human Blood—Cytokine Requirements:

To study the properties of DC progenitors in blood, it is not necessary to enrich for CD34+ multilineage progenitors which are so rare (<0.1%) in normal blood (Ema, et al., (1990) *Blood*, 75:1941). The need for exogenous cytokines may vary from one experimental situation to another depending on their endogenous production (e.g. TNF) by cells in the culture. However, it is to date essential to add GM-CSF. Exogenous TNF-α is useful to increase DC numbers and function, as described by Caux et al. (1992) *Nature*, 360:258), but primarily when one uses cord blood or blood from patients who are receiving CSF therapy to compensate for chemotherapy. The function of TNF may be to diminish granulocyte production Santiago-Schwarz, et al. (1993) *Blood*, 82:3019; Caux, et al., (1993) *J. Exp. Med.*, 177:1815), and to enhance responsiveness of an early progenitor to GM-CSF as by inducing a chain of the GM-CSF receptor (Santiago-Schwartz, et al. (1993), *Blood*, 82:3019; Caux, et al., (1993) *J. Exp. Med.*, 177:1815). With normal adult blood, IL-4 is the desired exogenous cytokine that is to be applied in combination with GM-CSF. Without being bound by theory, we suspect that IL-4 acts by suppressing the monocyte differentiation potential of the DC progenitor (Jansen, et al., (1989) *J. Exp. Med.*, 170:577).

GM-CSF is essential to grow DCs from all sources used. Additional cytokines required for optimal DC growth from the various sources are, however, strikingly different (TNF α versus IL-4). We suspect that this is due to the fact that the main DC progenitors involved differ. In cord blood the DC aggregates likely derive from CD34+ cells as preliminary experiments (N. Romani, unpublished) have shown that depletion of CD34+ cells from the initial inoculum virtually abolishes the formation of DC aggregates. This also readily explains the need to add TNF α which is known to induce responsiveness to GM-CSF of CD34+ cells (Santiago-Schwartz, et al., *Blood*, 82:3019; Caux, et al., (1993) *J. Exp. Med.*, 177:1815). Ongoing experiments indicate that IL-4 does not seem to enhance DC development from precursors that arise in cord blood mononuclear cells supplemented with GM-CSF and TNF-α [D. Brang, unpublished]. We do not yet know, however, whether IL-4 is produced endogenously in such cultures. Endogenous IL-4 might suppress—similar to exogenously added IL-4 in adult blood cultures—the monocyte differentiation potential of more mature DC progenitors that derive from CD34+ multilineage progenitors in response to GM-CSF and TNF α. DC developmental pathways in cultures of blood derived from cancer patients during hematopoietic recovery are presumably similar to cord blood. Besides CD34+ cells it is, however, likely that more committed precursors are also involved as the percentage of CD34+ cells in the CD3/HLA-DR depleted mononuclear cell fraction did not strictly correlate with DC yields. In normal adult blood in response to GM-CSF and TNF α only after a prolonged culture period (2 weeks) some DC aggregates emerged likely from early, rare DC progenitors similar to those in cord blood or blood of cancer patients during hematopoietic recovery. The main DC progenitor(s) in normal adult blood, however, appear(s) to be more frequent as only 2 days of culture are needed before many DC aggregates appear [FIG. 21]. Prior work in mouse (Inaba, et al., (1993) *Proc. Natl. Acd. Sci. USA*, 90:3038) and man (Reid., et al., (1992) *J. Immunol*, 149:2681) has described that the multilineage colonies that are induced by GM-CSF in semisolid agar cultures contain all 3 types of myeloid progeny, i.e. granulocytes, macrophages, and dendritic cells. The principal DC progenitor in normal human peripheral blood seems more differentiated since granulocytes do not develop. This committed progenitor is GM-CSF responsive, and likely bipotential, developing into macrophages rather than DCs unless its monocyte differentiation potential is suppressed by IL-4.

REFERENCES

1. Steinman, R. M. 1991. The dendritic cell system and its role in immunogenicity. *Ann. Rev. Immunol.* 9:271.
2. Witmer-Pack, M. D., W. Olivier, J. Valinsky, G. Schuler, and R. M. Steinman. 1987. Granulocyte/macrophage colony-stimulating factor is essential for the viability and function of cultured murine epidermal Langerhans cells. *J. Exp. Med.* 166:1484.
3. Heufler, C., F. Koch, and G. Schuler. 1987. Granulocyte-macrophage colony-stimulating factor and interleukin-1 mediate the maturation of murine epidermal Langerhans cells into potent immunostimulatory dendritic cells. *J. Exp. Med.* 167:700.
4. Romani, N., S. Koide, M. Crowley, M. Witmer-Pack, A. M. Livingstone, C. G. Fathman, K. Inaba, and R. M. Steinman. 1989. Presentation of exogenous protein antigens by dendritic cells to T cell clones: intact protein is presented best by immature, epidermal Langerhans cells. *J. Exp. Med.* 169:1169.
5. Inaba, K., N. Romani, and R. M. Steinman. 1989. An antigen-independent contact mechanism as an early step in T-cell-proliferative responses to dendritic cells. *J. Exp. Med.* 170:527.
6. Pure', E., K. Inaba, M. T. Crowley, L. Tardelli, M. D. Witmer-Pack, G. Ruberti, G. Fathman, and R. M. Steinman. 1990. Antigen processing by epidermal Langerhans cells correlates with the level of biosynthesis of major histocompatibility complex class II molecules and expression of invariant chain. *J. Exp. Med.* 172:1459.
7. Kampgen, E., N. Koch, F. Koch, P. Stoger, C. Heufler, G. Schuler, and N. Romani. 1991. Class II major histocompatibility complex molecules of murine dendritic cells: synthesis, sialylation of invariant chain, and antigen processing capacity are downregulated upon culture. *Proc. Natl. Acad. Sci. USA* 88:3014.
8. Austyn, J. M., J. W. Kupiec-Weglinski, D. F. Hankins, and P. J. Morris. 1988. Migration patterns of dendritic cells in the mouse. Homing to T cell-dependent areas of spleen, and binding within marginal zone. *J. Exp. Med.* 167:646.
9. Larsen, C. P., P. J. Morris, and J. M. Austyn. 1990. Migration of dendritic leukocytes from cardiac allografts into host spleens: a novel pathway for initiation of rejection. *J. Exp. Med.* 171:307.
10. Austyn, J. M., and C. P. Larsen. 1990. Migration patterns of dendritic leukocytes. *Transpl.* 49:1.
11. Veldman, J. E., and E. Kaiserling. 1980. Interdigitating cells. In The Reticuloendothelial System,Morphology. I. Carr, and W. T. Daems, editors. Plenum Publishing Corp., New York. 381–416.
12. Witmer, M. D., and R. M. Steinman. 1984. The anatomy of peripheral lymphoid organs with emphasis on accessory cells: light microscopic, immunocytochemical studies of mouse spleen, lymph node and Peyer's patch. *Am. J. Anat.* 170:465.
13. Kraal, G., M. Breel, M. Janse, and G. Bruin. 1986. Langerhans cells, veiled cells, and interdigitating cells in the mouse recognized by a monoclonal antibody. *J. Ex. Med.* 163:981.
14. Inaba, K., J. P. Metlay, M. T. Crowley, and R. M. Steinman. 1990. Dendritic cells pulsed with protein antigens in vitro can prime antigen-specific, MHC-restricted T cells in situ. *J. Exp. Med.* 172:631.
15. Steinman, R. M., D. S. Lustig, and Z. A. Cohn. 1974. Identification of a novel cell type in peripheral lymphoid organs of mice. III. Functional properties in vivo. *J. Exp. Med.* 139:1431.
16. Pugh, C. W., G. G. MacPherson, and H. W. Steer. 1983. characterization of nonlymphoid cells derived from rat peripheral lymph. *J. Exp. Med.* 157:1758.
17. Fossum, S. 1989. The life history of dendritic leukocytes [DL]. In Current Topics in Pathology. O. H. Ivessen, editor. Springer-Verlag, Berlin. 101–124.
18. Katz, S. I., K. Tamaki, and D. H. Sachs. 1979. Epidermal Langerhans cells are derived from cells originating in bone marrow. *Nature* 282:324.
19. Hart, D. N. J., and J. W. Fabre. 1981. Demonstration and characterization of Ia-positive dendritic cells in the interstitial connective tissues of rat heart and other tissues, but not brain. *J. Exp. Med.* 154:347.
20. Bowers, W. E., and M. R. Berkowitz. 1986. Differentiation of dendritic cells in cultures of rat bone marrow cells. *J. Exp. Med.* 163:872.
21. Reid, C. D. L., P. R. Fryer, C. Clifford, A. Kirk, J. Tikerpae, and S. C. Knight. 1990. Identification of hematopoietic progenitors of macrophages and dendritic Langerhans cells [DL-CFU] in human bone marrow and peripheral blood. *Blood* 76:1139.
22. Kajigaya, S., T. Suda, J. Suda, M. Saito, Y. Miura, M. Iizuk, S. Kobayashi, N. Minato, and T. Sudo. 1986. A recombinant murine granulocyte/macrophage (GM) colony-stimulating factor derived from an inducer T cell line (IH5.5). Functional restriction to GM progenitor cells. *J. Exp. Med.* 164:1102.
23. Agger, R., M. T. Crowley, and M. D. Witmer-Pack. 1990. The surface of dendritic cells in the mouse as studied with monoclonal antibodies. *Int. Rev. Immunol.* 6:89.
24. Crowley, M., K. Inaba, M. Witmer-Pack, and R. M. Steinman. 1989. The cell surface of mouse dendritic cells: FACS analyses of dendritic cells from different tissues including thymus. *Cell. Immunol.* 118:108.
25. Freudenthal, P. S., and R. M. Steinman. 1990. The distinct surface of human blood dendritic cells, as observed after an improved isolation method. *Proc. Natl. Acad. Sci. USA* 87:7698.
26. Drexhage, H. A., H. Mullink, J. de Groot, J. Clarke, and B. M. Balfour. 1979. A study of cells present in peripheral lymph of pigs with special reference to a type of cell resembling the Langerhans cells. *Cell. Tiss. Res.* 202:407.
27. Schuler, G., and R. M. Steinman. 1985. Murine epidermal Langerhans cells mature into potent immunostimulatory dendritic cells in vitro. *J. Exp. Med.* 161:526.

28. Romani, N., M. Witmer-Pack, M. Crowley, S. Koide, G. Schuler, K. Inaba, and R. M. Steinman. 1991. Langerhans cells as immature dendritic cells. CRC Press, Boston. 191–216.
29. Romani, N., G. Schuler, and P. Fritsch. 1986. Ontogeny of Ia-positive and Thy-1 positive leukocytes of murine epidermis. J. Invest. Dermatol. 86:129.
30. Nussenzweig, M. C., R. M. Steinman, M. D. Witmer, and B. Gutchinov. 1982. A monoclonal antibody specific for mouse dendritic cells. Proc. Natl. Acad. Sci. USA 79:161.
31. Inaba, K., J. P. Metlay, M. T. Crowley, M, Witmer-Pack, and R. M. Steinman. 1990. Dendritic cells as antigen presenting cells in vivo. Int. Rev. Immunol. 6:197.
32. Barclay, A. N., and G. Mayrhofer. 1981. Bone marrow origin of Ia-positive cells in the medulla of rat thymus. J. Exp. Med. 153:1666.
33. Rabinowitz, S. S., and S. Gordon. 1991. Macrosialin, a macrophage-restricted membrane sialoprotein differentially glycosylated in response to inflammatory stimuli. J. Exp. Med. 174:827.
34. Agger, R., M. Witmer-Pack, N. Romani, H. Stossel, W. J. Swiggard, J. P. Metlay, E. Storozynsky, P. Freimuth, and R. M. Steinman. 1992. Two populations of splenic dendritic cells detected with M342, a new monoclonal to an intracellular antigen of interdigitating dendritic cells and some B lymphocytes. J. Leuk. Biol. 52:34.
35. Kaplow, L. S. 1981. Cytochemical identification of mononuclear phagocytes, in "Manual of macrophage methodology" eds H. B. Herscowitz, H. T. Holden, J. A. Bellanti, and A. Ghaffer. Marcel Dekker,Inc., New York. 199–207.
36. Stossel, H., F. Koch, E. Kampgen, P. Stoger, A. Lenz, C. Heufler, N. Romani, and G. Schuler. 1990. Disappearance of certain acidic organelles [endosomes and Langerhans cell granules] accompanies loss of antigen processing capacity upon culture of epidermal Langerhans cells. J. Exp. Med. 172:1471.
37. Steinman, R. M., and Z. A. Cohn. 1973. Identification of a novel cell type in peripheral lymphoid organs of mice. I. Morphology, quantitation, tissue distribution. J. Exp. Med. 137:1142.
38. Steinman, R. M., and M. D. Witmer. 1978. Lymphoid dendritic cells are potent stimulators of the primary mixed leukocyte reaction in mice. Proc. Natl. Acad. Sci. USA 75:5132.
39. Scheicher, C., M. Mehlig, R. Zecher, and K. Reske. 1992. Dendritic cells from mouse bone marrow: in vitro differentiation by low doses of recombinant granulocyte-macrophage-CSF. J. Immunol. Methods In Press:
40. Crowley, M. T., K. Inaba, M. D. Witmer-Pack, S. Gezelter, and R. M. Steinman. 1990. Use of the fluorescence activated cell sorter to enrich dendritic cells from mouse spleen. J. Immunol. Methods 133:55.
41. Naito, K., K. Inaba, Y. Hirayama, M. Inaba-Miyama, T. Sudo, and S. Muramatsu. 1989. Macrophage factors which enhance the mixed leukocyte reaction initiated by dendritic cells. J. Immunol. 142:1834.
42. Steinman, R. M., G. Kaplan, M. D. Witmer, and Z. A. Cohn. 1979. Identification of a novel cell-type in peripheral lymphoid organs of mice. V. Purification of spleen dendritic cells, new surface markers, and maintenance in vitro. J. Exp. Med. 149:1.
43. Goud, T. J. L. M., C. Schotte, and R. van Furth. 1975. Identification and characterization of the monoblast in mononuclear phagocyte colonies grown in vitro. J. Exp. Med. 142:1180.
44. Inaba, K., Steinman, R. M., Witmer-Pack, M., K. Aya, M. Inaba, T. Sudo, S. Wolpe, and G. Schuler. 1992. Identification of proliferating dendritic cell precursors in mouse blood. J. Exp. Med. 175:1157.
45. Britz, J. S., P. W. Askenase, W. Ptak, R. M. Steinman, and R. K. Gershon. 1982. Specialized antigen-presenting cells: Splenic dendritic cells, and peritoneal exudate cells induced by mycobacteria, activate effector T cells that are resistant to suppression. J. Exp. Med. 155:1344.
46. Lechler, R. I. and J. R. Batchelor. 1982. Restoration of immunogenicity to passenger cell-depleted kidney allografts by the addition of donor strain dendritic cells. J. Exp. Med. 155:31.
47. Boog, C. J. P., W. M. Kast, H. Th. M. Timmers, J. Boes, L. P. De Waal, and C. J. M. Melief. 1985. Abolition of specific immune response defect by immunization with dendritic cells. Nature 318:59.
48. Faustman, D. L., R. M. Steinman, H. M. Gebel, V. Hauptfeld, J. M. Davie, and P. E. Lacy. 1984. Prevention of rejection of murine islet allografts by pretreatment with anti-dendritic cell antibody. Proc. Natl. Acad. Sci. USA 81:3864.
49. Iwai, H., S.-I. Kuma, M. M. Inaba, R. A. Good, T. Yamashita, T. Kumazawa, and S. Ikehara. 1989. Acceptance of murine thyroid allografts by pretreatment of anti-Ia antibody or anti-dendritic cell antibody in vitro. Transpl. 47:45.
50. Havenith, C. E. G., A. J. Breedijk, M. G. H. Betjes, W. Calame, R. H. J. Beelen, and E. C. M. Hoefsmit. 1992. T cell priming in situ by intratracheally instilled antigen-pulsed dendritic cells. Am. J. Resp. Cell & Molec. Biol. Submitted.
51. Liu, L. M. and G. G. MacPherson. 1993. Antigen acquisition by dendritic cells: Intestinal dendritic cells acquire antigen administered orally and can prime naive T cells "in vivo". J. Exp. Med. In Press:
52. Holt, P. G., M. A. Schon-Hegrad, and J. Oliver. 1987. MHC class II antigen-bearing dendritic cells in pulmonary tissues of the rat. Regulation of antigen presentation activity by endogenous macrophage populations. J. Ep. Med. 167:262.
53. Bujdoso, R., J. Hopkins, B. M. Dutia, P. Young, and I. McConnell. 1989. Characterization of sheep afferent lymph dendritic cells and their role in antigen carriage. J. Exp. Med. 170:1285.
54. Crowley, M., K. Inaba, and R. M. Steinman. 1990. Dendritic cells are the principal cells in mouse spleen bearing immunogenic fragments of foreign proteins. J. Exp. Med. 172:383.
55. Schimonkevitz, R., J. Kappler, P. Marrack, and H. Grey. 1983. Antigen recognition by H-2-restricted T cells. I. Cell-free antigen processing. J. Exp. Med. 158:303.
56. Ziegler, H. K. and E. R. Unanue. 1982. Decrease in macrophage antigen catabolism caused by ammonia and chloroquine is associated with inhibition of antigen presentation T cells. Proc. Natl. Acad. Sci. USA 79:175.
57. Pancholi, P., A. Mirza, V. Schauf, R. M. Steinman, and N. Bhardwaj. 1993. Presentation of mycobacterial antigens by human dendritic cells: lack of transfer from infected macrophages. Infection and Immunity submitted:
58. Inaba, K., M. Inaba, N. Romani, H. Aya, M. Deguchi, S. Ikehara, S. Muramatsu, and R. M. Steinman. 1992. Generation of large numbers of dendritic cells from mouse bone marrow cultures supplemented with granulocyte-macrophage colony stimulating factor. J. Exp. Med. 176:1693.
59. 1993. Manual of methods for general bacteriology. In P. Gerhardt, R. G. E. Murray, R. E. Cogtillo, E. W. Nester, W. A. Wood, N. R. Krieg, and G. B. Philips, editors.

60. Cohn, Z. A. 1963. The fate of bacteria within phagocytic cells. I. The degradation of isotopically labeled bacteria by polymorphonuclear leucocytes and macrophages. *J. Exp. Med.* 117:27.
61. Steinman, R. M. and Z. A. Cohn. 1972. The interaction of particulate horseradish peroxidase (HRP) -anti HRP immune complexes in mouse peritoneal macrophages in vitro. *J. Cell Biol.* 55:616.
62. Ehrenreich, B. A. and Z. A. Cohn. 1967. The uptake and digestion of iodinated human serum albumin by macrophages in vitro. *J. Exp. Med.* 126:941.
63. Steinman, R. M. and Z. A. Cohn. 1972. The interaction of soluble horseradish peroxidase in mouse peritoneal macrophages in vitro. *J. Cell Biol.* 55:186.
64. Cohn, Z. A. and B. A. Ehrenreich. 1969. The uptake, storage and intracellular hydrolysis of carbohydrates by macrophages. *J. Exp. Med.* 129:201.
65. Ehrenreich, B. A. and Z. A. Cohn. 1969. The fate of peptides pinocytosed by macrophages in vitro. *J. Exp. Med.* 129:227.
66. Hunt, D. F., H. Michel, T. A. Dickinson, J. Shabanowitz, A. L. Cox, K. Sakaguchi, E. Appella, H. M. Grey, and A. Sette. 1992. Peptides presented to the immune system by the murine class II major histocompatibility complex molecule I-Ad. *Science* 256:1817.
67. Rudensky, A. Y., P. Preston-Hurlburt, S.-C. Hong, A. Barlow, and C. A. Janeway Jr. 1991. Sequence analysis of peptides bound to MHC class II molecules. *Nature* 353:622.
68. Jensen, P. E. 1988. Protein synthesis in antigen processing. *J. Immunol.* 141:2545.
69. Harding, C. V. and E. R. Unanue. 1990. Quantitation of antigen-presenting cell MHC class II/peptide complexes necessary for T-cell stimulation. *Nature* 346:574.
70. Demotz, S., H. M. Grey, and A. Sette. 1990. The minimal number of class II MHC-antigen complexes needed for T cell activation. *Science* 249:1028.
71. Bhardwaj, N., J. W. Young, A. J. Nisanian, J. Baggers, and R. M. Steinman. 1992. Small amounts of superantigen on dendritic cells are sufficient to initiate T cell responses. Submitted
72. Breel, M., R. E. Mebius, and G. Kraal. 1987. Dendritic cells of the mouse recognized by two monoclonal antibodies. *Eur. J. Immunol.* 17:1555.
73. Fossum, S. and B. Rolstad. 1986. The roles of interdigitating cells and natural killer cells in the rapid rejection of allogeneic lymphocytes. *Eur. J. Immunol.* 16:440.
74. Reis e Sousa, C., P. D. Stahl, and J. M. Austyn. 1993. Phagocytosis of antigens by langerhans cells in vitro. *J. Exp. Med.* In Press.
75. Harding, C. V., R. W. Roof, and E. R. Unanue. 1990. Turnover of Ia-peptide complexes is facilitated in viable antigen-presenting cells:Biosynthetic turnover of Ia vs. peptide exchange. *Proc. Natl. Acad. Sci. USA* 86:4230.
76. Brodsky, F. M. and L. E. Guagliardi. 1991. The cell biology of antigen processing and presentation. *Ann. Rev. Immunol.* 9:707.
77. Nonacs, R., C. Humborg, J. P. Tam, and R. M. Steinman. 1992. Mechanisms of mouse spleen dendritic cell function in the generation of influenza-specific, cytolytic T lymphocytes. *J. Exp. Med.* 176:519.
78. Freiden, Thomas R., T. Sterling, A. Pablos-Mendez, J. Kilburn, G. Cauthen and S.W. Dooley, 1993. The emergence of drug-resistant tuberculosis in New York City. No Eng. *J. of Med.* 328:521.

While we have hereinbefore described a number of embodiments of this invention, it is apparent that the basic constructions can be altered to provide other embodiments which utilize the methods and compositions of this invention. Therefore, it will be appreciated that the scope of this invention is defined by the claims appended hereto rather than by the specific embodiments which have been presented hereinbefore by way of example.

We claim:

1. A method of treating autoimmune disease comprising administering to a patient in need of treatment a therapeutically effective amount of a composition comprising antigen-activated dendritic cells, wherein dendritic cells are produced from proliferating cell cultures by a method comprising providing a tissue source comprising dendritic cell precursors;

culturing the tissue source on a substrate and in culture medium to expand the number of dendritic cell precursors by allowing the dendritic cell precursors to proliferate; wherein said culture medium comprises GM-CSF and at least one other factor which inhibits the proliferation or maturation of non-dendritic cell precursors thereby increasing the proportion of dendritic cell precursors in the culture; and continuing to culture the dendritic cell precursors for a period of time sufficient to allow them to mature into mature dendritic cells;

wherein the dendritic cells are pulsed with self-protein, and wherein the dendritic cells process the self-protein to produce modified self-protein antigen, which is expressed by the dendritic cells.

2. The method of claim 1, wherein the autoimmune disease is selected from the group consisting of multiple sclerosis, myasthenia gravis, atopic dermatitis, and juvenile diabetes.

3. The method of claim 1 wherein, the autoimmune disease is selected from the group consisting of multiple sclerosis and juvenile diabetes.

4. The method of claim 1, wherein said factor inhibits macrophage proliferation or maturation.

5. The method of claim 1, wherein said tissue source is human blood.

6. The method of claim 1, wherein said factor is selected from the group consisting of IL4 and IL-13.

7. The method of claim 6, wherein said factor is IL-4.

8. The method of claim 7, wherein IL-4 is present in the culture medium in the range of 500–1000 U/ml.

9. The method of claim 1, wherein the culture medium further comprises TNF-α.

10. The method according to claim 1, wherein fetal calf serum is present in the culture medium in an amount of about 1 to 15%.

11. The method according to claim 1, wherein the fetal calf serum is present in the culture medium in an amount of about 10%.

12. The method according to claim 5, wherein GM-CSF is present in the medium at a concentration of about 1–1000 U/ml.

13. The method according to claim 12, wherein the GM-CSF is present in the medium at a concentration of about 400–800 U/ml.

14. The method according to claim 13, wherein the GM-CSF is present at a concentration of about 800 U/ml.

15. The method according to claim 1, wherein at least one factor selected from the group consisting of TNF-α, G-CSF, IL-1 and IL-3 is present in the culture medium.

* * * * *